(12) United States Patent
Laten

(10) Patent No.: US 6,559,359 B1
(45) Date of Patent: May 6, 2003

(54) PLANT RETROVIRAL POLYNUCLEOTIDES AND METHODS FOR USE THEREOF

(75) Inventor: Howard Mark Laten, Arlington Heights, IL (US)

(73) Assignee: Loyola University of Chicago, Chicago, IL (US)

( * ) Notice: Subject to any disclaimer, the term of this patent is extended or adjusted under 35 U.S.C. 154(b) by 0 days.

(21) Appl. No.: 09/254,776

(22) PCT Filed: Aug. 25, 1997

(86) PCT No.: PCT/US97/14802

§ 371 (c)(1),
(2), (4) Date: May 3, 1999

(87) PCT Pub. No.: WO98/09505

PCT Pub. Date: Mar. 12, 1998

Related U.S. Application Data

(60) Provisional application No. 60/025,853, filed on Sep. 9, 1996.

(51) Int. Cl.[7] .............................. A01H 4/00; A01H 1/00; C12N 15/82; C12N 5/04; C07H 21/04
(52) U.S. Cl. .................. 800/298; 435/69.1; 435/320.1; 435/325; 435/468; 435/410; 435/419; 536/23.1; 536/23.4; 536/23.72; 536/24.1; 800/295
(58) Field of Search ............................. 536/23.1, 23.4, 536/23.72, 24.1; 435/69.1, 320.1, 325, 468, 410, 419; 800/295, 298

(56) References Cited

U.S. PATENT DOCUMENTS 5,527,695 A    6/1996   Hodges et al.

FOREIGN PATENT DOCUMENTS

WO    WO 90/11367    * 10/1990

OTHER PUBLICATIONS

Eller et al., Nucleic Acids Res., vol. 17, No. 9, pp. 3591–3592, 1989.*
Laten et al., Gene, vol. 134, pp. 153–159, 1993.*
Bi et al., Plant Mol. Biol., vol. 30, pp. 1315–1319, 1989.*
Altenbach et al., "Enhancement of the methionine content of seed proteins by the expression of a chimeric gene encoding a methionine–rich protein in transgenic plants", *Plant Mol. Biol.*, 13:513.
Bi et al., "Sequence analysis of a cDNA containing the gag and prot regions of the soybean retrovirus–like element, SIRE–1", *Plant Mol. Biol.*, 30:1315–1319(1996).
Brisson, N. et al., "Expression of a bacterial gene in plants by using a viral vector", *Nature*, 310:511–514(1994).
Britten et al., "Active gypsy/Ty3 Retrotransposons or Retroviruses in *Caenorhabditis elegans*", *Proc. Natl. Acad. Sci.*, 92:599(1995).
Bureau et al., "Transduction of a Cellular Gene By a Plant Retroelement", *Cell*, 77:479(1994).
Casacuberta et al., "Sequence variability within the tobacco retrotransposon Tnt1 population", *EMBO J.* 14:2670–2678(1995).
Chambers et al., "Heptad Repeat Sequences are Located Adjacent to Hydrophobic Regions in Several Types of Virus Fusion Glycoproteins", *J. Gen. Virol.*, 71:3075(1995).
Chan et al., "*Core Structure of gp41 From the HIV Envelope Glycoprotein*", *Cell*, 89: 263–273(1997).
Chen et al., "Resistance to soybean mosaic virus conferred by two independent dominant genes in PI 486355", *J. Hered.* 84: 25(1993).
Choi et al., "The long terminal repeats of a murine retrovirus encode a trans–activator for cellular genes", *J. Biol. Chem.*, 269: 19691–19694(1994).
Day et al., "Expression of an antisense viral gene in transgenic tobacco confers resistance to the DNA virus tomato golden mosaic virus", *Proc. Natl., Acad. Sci. U.S.A.* 88:6721–2725(1991).
Di et al., "Production of transgenic soybean lines expressing the bean pod mottle virus coat protein precursor gene", *Plant Cell. Reports*, 15:746–750(1996).
Eickbush, T.H., in *The Evolutionary Biology of Viruses*, S.S. Morse, Ed. Ravens Press, New York, 1994, pp. 437–484.
Eller et al., "Nucleotide Sequence of Full Length Human Embryonic Myosin Heavy Chain cDNA", *Nucleic Acids Research*, 17:3591–3592(1989).
Fass et al., "Retrovirus Envelope Domain at 1.7 Angstrom Resolution", *Nature Struct. Biol.*, 3:465–469(1996).
Felder et al., "*Tas*, a Retrotransposon from the Parasitic Nematode *Ascaris lumbricoides*", *Gene*, 149:219(1994).
Finnegan, D.J., "Eukaryotic transposable elements and genome evolution", *Trends Genet.*, 5:103–107(1989).
Flavell et al., Extreme heterogeneity of Ty1–copia group retrotransposons in plants, *Mol.Gen.Genet*, 231:233–242(1992).
Fontenot et al., "Structure and Self Assembly of a Retrovirus (FeLV) Proline Rich Neutralization Domain", *J. Biomo. Struct Dynam.*, 11:821–836(1994).
Friesen et al., "Gene Organization and Transcription of TED, a Lepidoteran Retrotransposon Integrated within Baculovirus Genome", *Mol. Cell. Biol.*, 10:3067–3077(1990).
Gallaher et al., "A General Model for the Surface Glycoproteins of HIV and Other Retroviruses", *AIDS Res. Hum. Retroviruses*, 11:191–202(1995).
Golemboski et al., "Plants Transformed with a Tobacco Mosaic Virus Nonstructural Gene Sequence are Resistant to the Virus", *Proc. Natl. Acad. Sci., U.S.A.* 87:6311–6315(1990).

(List continued on next page.)

*Primary Examiner*—David Guzo
(74) *Attorney, Agent, or Firm*—Marshall, Gerstein & Borun

(57) ABSTRACT

Retroviral and retroviral-like polynucleotides, and vectors, proteins, and antibodies derived therefrom, that are useful for the introduction of genetic information into soybeans and other plant species.

58 Claims, 46 Drawing Sheets

OTHER PUBLICATIONS

Grandbastien, M.–A., "Activation of Plant Retrotransposons Under Stress Conditions", *Trends in Plant Science*, 3:181–187(1998).

Grandbastien, M.–A., "Retroelements in higher plants", *Trends Genet.*, 8: 103–108(1992).

Grandbastien et al., "Tnt1, a mobile retroviral–like transposable element of tobacco isolated by plant cell genetics", *Nature*, 337:376–380(1989).

Hirochika, H., "Activation of tobacco retrotransposons during tissue culture", *EMBO J.*, 12: 2521–2528(1993).

Hoffman et al., "A modified storage protein is synthesized, processed, and degraded in the seeds of transgenic plants", *Plant Mol. Biol.*, 11: 717(1988).

Hunter et al., "Retrovirus Envelope Glycoporteins" *Microbiol. Immunol.* 157:187–253(1990).

Katz et al., "What is the role of the Cys–His motif in retroviral nucleocapsid (NC) proteins?", *Bioessay II*, 176–181(1989).

Kim et al., "Reteoviruses in Invertebrates: The gypsy Retrotransposon is Apparently an Infectious Retrovirus of *Drosophila melanogaster*", *Proc. Natl. Acad. Sci. USA*, 91:1285(1994).

Laten, H.M. et al., "SIRE–1, a copia/Ty1–like retroelement from soybean, encodes a retroviral envelope–like protein", *Proc. Natl. Acad. Sci. USA*, 95:6897–6902 (1998).

Laten, H.M. et al., "SIRE–1, a long interspersed repetitive DNA element from soybean with weak sequence similarity to retrotransposons: initial characterization and partial sequence", *Gene*, 134:153–159(1993).

Laten, H.M., "Phylogenetic Evidence for Ty1–copia–like Endogenous Retroviruses in Plant Genomes", *Genetica*, 107:87–93(1999).

Luzzi et al., "A gene for resistance to the soybean root–knot nematode in soybean", *J. Hered.*, 85: 484(1994).

McDonald, J.F., "Evolution and consequences of transposable elements" *Curr. Opin. Genet. Devel.*, 3:855–864(1990).

Mellentin–Michelotti et al., "The 5' enhancer of the mouse mammary tumor virus long terminal repeat contains a functional AP–2 element", *J. Biol. Chem.*, 269: 31983–31990(1994).

Miller, A.D., "Retroviral Vectors", *Current Topics in Microbiology and Immunology*, 158:2–24(1992).

Patience et al., "Our Retroviral Heritage", *Trends Genet.*, 13:116–120(1997).

Peterson–Burch et al., "Retroviruses in Plants?", *Trends in Genetics*,16:151–152(2000).

Potrykus, I., "Gene Transfer to Plants: Assessment of Published Approaches and Results", *Annu. Rev. Plant Physiol. Mol. Biol.*, 42:205–225 (1991).

Pouteau et al., "Microbial elicitors of plant defense responses activate transcription of a retrotransposon", *Plant J.*, 5:535–542(1994).

SanMiguel et al., "Nested Retrotransposons in the Intergenic Regions of the Maize Genome", *Science*, 274:765(1996).

Smith et al., "Viral Vectors in Gene Therapy", *Annu. Rev. Microbiol.*, 49:807–838 (1995).

Tanda et al., "The Drosophila tom Retrotransposon Encodes an Envelope Protein", *Mol. Cell. Biol.*, 14:5392–5401(1994).

Varmus et al., "Retroviruses", In *Mobile DNA*, D.E. Berg and M.M. Howe, eds, (ASM, Washington, D.C.) pp. 53–108(1989).

Voytas et al., "copia–like retrotransposons are ubiquitous among plants", *Proc. Natl. Acad. Sci. U.S.A.*, 89:7124–7128(1992).

White et al., "Retrotransposons in the flanking regions of normal plant genes: A role for copia–like elements in the evolution of gene structure and expression", *Proc. Nad. Acad. Sci. U.S.A.*, 91:11792–11796(1994).

* cited by examiner

5' TNTTNGATCG(G/T)GTNCA(A/G)TGCTG 3'

FIGURE 1

| | | | | |
|---|---|---|---|---|
| <u>TATTGGATCG</u> | <u>GGTGCAGTGC</u> | <u>TG</u>TTTTTGGC | AGGAACAAAT | 40 |
| TATGTCATGG | TTGTTCTGCC | AGCAGATTTA | TGATTAAATC | 80 |
| CAAGTCCTCT | CTGGTTTCCA | ACATTCTTCC | CAAGCTGTAG | 120 |
| CACCTCATCA | AGCAAATTTG | AGCCTTTATT | CAGCATCTTT | 160 |
| ATTGATTTTG | TCATGTTTTC | CAGTTTAGAG | TTCAGAAAAC | 200 |
| CAATTTCTCC | TTTAAGTTCA | GAGATTTCCT | CTTCATGTGC | 240 |
| CTCCTTCTCA | GCCTCCAGAT | TTGCAATGAC | CTTCTTTAGT | 280 |
| TGTGCTTCTT | GCTGAAGAAT | CTTCTCACTT | TTGATGCATA | 320 |
| GTTCTCTATA | GGATATAGCA | AGCTCATCAA | AAGTGATTTC | 360 |
| ACTATCTGTA | TCACTTGAAT | CTTCAGCAGA | TTCAAATCTC | 400 |
| CCAGTGAGTG | CATTCACATC | TCTGTCAGAA | TCACTTCTTG | 440 |
| TTCACTCTCT | GTATCATCAG | ACCGACATAC | AGAAAGTCCT | 480 |
| TTCCTCTGCT | TCTTGAGATG | AGTGGGACAT | TCAGCTTTGA | 520 |
| TGTGTCCATA | GCCTTCACAC | CCATGGCATT | GAATTCCTTT | 560 |
| GCTGTGACTG | GGCTTTTCAT | CTGACCTTTT | CTGGTATTCA | 600 |
| CTACCTTTCC | TGATGTCGAA | AGGGATGTTC | CGGACATGTG | 640 |
| GTTTCTGCCT | CCTGTCCATT | CTGTTCAGCA | CTTTGTTGAA | 680 |
| CTGTTTTCCA | AGGAGCACAA | CTGCGTTAGT | CAGACCTTCA | 720 |
| TCAGTATCCA | GGTCATACTC | ATCTTCTTCT | CCTT<u>CAGCAC</u> | 760 |
| <u>TGCACCCGAT</u> | <u>CCAATA</u> | | | 776 |

FIGURE 2

| GM776 (NT) | ELEMENT (NT) | % IDENTITY | Q | RANDOMIZED MEAN Q | RANDOMIZED S.D. | RANDOMIZED P |
|---|---|---|---|---|---|---|
| 150-465 | TAL (735-1045) | 50.3 | 127.2 | 111.8 | 2.9 | 0.0000003 |
| 360-670 | TAL (1210-1510) | 51.0 | 122.3 | 109.2 | 3.2 | 0.00009 |
| 144-382 | TYL (4404-4640) | 51.2 | 106.3 | 93.1 | 3.5 | 0.0003 |

| | |
|---|---|
| F1 (M13/pUC reverse) | 5'-CCCAGTCACGACGTTGTAAAACG-3' |
| F2 (208-226) | 5'-TCCTTTAAGTTCAGAGATT-3' |
| R1 (M13/pUC reverse) | 5'-AGCGGATAACAATTTCACACAGG-3' |

B

Sense strand

| | |
|---|---|
| R1 (M13/pUC reverse) | 5'-CCCAGTCACGACGTTGTAAAACG-3' |
| R2 (320-349) | 5'-GTAATGGTCAACCAGACCACAGTT-3' |
| R3 (455-471) | 5'-GACGAATTGGCACTTGG-3' |
| R4 (708-725) | 5'-TTTGCACTGCCTTGGGAG-3' |
| R5 (983-999) | 5'-CCAAGGAGCACAACTGC-3' |
| R6 (1018-1037) | 5'-GCTGAACAGAATGGACAGGA-3' |
| R7 missing | |

Complementary strand

| | |
|---|---|
| F1 (M13/pUC reverse) | 5'-AGCGGATAACAATTTCACACAGG-3' |
| F2 (2304-2321) | 5'-AAAGATATAACAAGATTTA-3' |
| F3 (2077-2097) | 5'-CCCGATCTTATTCCTTGACA-3' |
| F4 (1747-1766) | 5'-CTTGCCACAGTAGTGACA-3' |
| F5 (1566-1583) | 5'-TCTTCCCAAGCTGTAGCA-3' |
| F6 (1462-1481) | 5'-TCCTTTAAGTTCAGAGATT-3' |

```
TCCGGTCCCT GGCTTGGTAG CCCCCAGATG TAGGTGAGGT      40
TGCACCGAAC TGGGTTAACA ATTCTCTTGT GTTAGTTACT      80
TGTTTAATCT GTTCATACAG TCAAACATAA TCTGCATGTT     120
CTGAAGCGTG ATGTCGTGAC ATCCGGTACG ACATCTGTCA     160
TTGGTATCAG AATTTCAATT GGTATCAGAG CAGGCACTCG     200
AATTCACTGA GTGAGATCTA GGGAGATAAA TTCTGATGAA     240
CATGGAGAAA GAAGGAGGAC CAGTGAACAG ACCACCAATT     280
CTGGATGGAA CCAACTATGA ATACTGGAAA GCAAGGATGG     320
TGGCCTTCCT CAAATCACTG GATAGCAGAA CCTGGAAAGC     360
TGTCATCAAA GACTGGGAAC ATCCCAAGAT GCTGGACACA     400
GAAGGAAAGC CCACTGATGG ATTGAAGCCA GAAGAAGACT     440
GGACTAAAGA AGAAGACGAA TTGGCACTTG GAAACTCCAA     480
AGCTTTGAAT GCTCTATTCA ATGGAGTTGA CAAGAATATC     520
TTCAGACTGA TCAACACATG CACAGTGGCC AAGGATGCAT     560
GGGAGATCCT GAAAACCACT CATGAAGGAA CCTCCAAAGT     600
GAAGATGTCC AGATTGCAAC TATTGGCCAC AAAATTCGAA     640
AATCTGAAGA TGAAGGAGGA AGAGTGTATT CATGACTTTC     680
ACATGAACAT TCTTGAAATT GCCAATGCTT GCACTGCCTT     720
GGGAGAAAGA ATGACTGATG AAAAGCTGGT GAGAAAGATC     760
CTCAGATCCT TGCCTAAGAG ATTTGACATG AAAGTCACTG     800
CAATAGAGGA GGCCCAAGAC ATTTGCAACC TGAGAGTAGA     840
```

FIGURE 6 A

```
TGAACTCATT GGTTCCCTTC AAACCTTTGA GCTAGGACTC    880
TCGGATAGGA CTGAAAAGAA GAGCAAGAAT CTGGCGTTCG    920
TGTCCAATGA TGAAGGAGAA GAAGATGAGT ATGACCTGGA    960
TACAGATGAA GGTCTGACTA ATGCAGTTGT GCTCCTTGGA   1000
AAACAGTTCA ACAAAGTGCT GAACAGAATG GACAGGAGGC   1040
AGAAACCACA TGTCCGGAAC ATCCCTTTCG ACATCAGGAA   1080
AGGTAGTGAA TACCAGAAAA GGTCAGATGA AAAGCCCAGT   1120
CACAGCAAAG GATTTCAATG CCATGGGTGT GAAGGCTATG   1160
GACACATCAA AGCTGAATGT CCCACTCATC TCAAGAAGCA   1200
GAGGAAAGGA CTTTCTGTAT GTCGGTCTGA TGATACAGAG   1240
AGTGAACAAG AAAGTGATTC TGACAGAGAT GTGAATGCAC   1280
TCACTGGGAG ATTTGAATCT GCTGAAGATT CAAGTGATAC   1320
AGACAGTGAA ATCACTTTTG ATGAGCTTGC TACATCCTAT   1360
AGAGAACTAT GCATCAAAAG TGAGAAGATT CTTCAGCAAG   1400
AAGCACAACT GAAGAAGGTC ATTGCAAATC TGGAGGCTGA   1440
GAAGGAGGCA CATGAAGAGG AGATCTCTGA GCTTAAAGGA   1480
GAAGTTGGTT TTCTGAACTC TAAACTGGAA AACATGACAA   1520
AATCAATAAA GATGCTGAAT AAAGGCTCAG ATATGCTTGA   1560
TGAGGTGCTA CAGCTTGGGA AGAATGTTGG AAACCAGAGA   1600
GGACTTGGGT TTAATCATAA ATCTGCTGGC AGAATAACCA   1640
TGACAGAATT TGTTCCTGCC AAAATCAGCA CTGGAGCCAC   1680
```

FIGURE 6 B

```
GATGTCACAA CATCGGTCTC GACATCATGG AACGCAGCAG    1720
AAAAAGAGTA AAAGAAAGAA GTGGAGGTGT CACTACTGTG    1760
GCAAGTATGG TCACATAAAG CCCTTTTGCT ATCATCTACA    1800
TGGCCATCCA CATCATGGAA CTCAAAGTAG CAGCAGCAGA    1840
AGGAAGATGA TGTGGGTTCC AAAACACAAG ATTGTCAGTC    1880
TTGTTGTTCA TACTTCACTT AGAGCATCAG CTAAGGAAGA    1920
TTGGTACCTA GATAGCGGCT GTTCCAGACA CATGACAGGA    1960
GTCAAAGAAT TTCTGGTGAA CATTGAACCC TGCTCCACTA    2000
GCTATGTGAC ATTTGGAGAT GGCTCTAAAG GAAAGATCAC    2040
TGGAATGGGA AAGCTAGTCC ATGATGGACT TCGTTATGTC    2080
AAGGAATAAG ATCGGGCTGC ACAATGCACA AGGCAAGATA    2120
AAATGTCAAA TGAAGAATTG AAGCTGCAGG ATCCATGATG    2160
TCGGATACAA TGTCCAGGAC ATCCTGCCCG AAAATACTGG    2200
AGTTGCTGCA CAATGCACAA GGCAAGATAA AGAAGTGAA    2240
GCTGCAGGAT CCACGATGTC GGATACGATG TCCAGGACAT    2280
CTGGCCCGAA AATACTGGAC ACATAAATCT GTTATATCTT    2320
TAACAGATTA TTGTGCAGTT AGCAACAGGT TAGACGATCT    2360
ATCTTTAGGA ACGAACTCTT CTAGTTCCGG AATTCGAGCT    2400
CGGTACCCGG GGATCCT                             2417
```

FIGURE 6 C

```
SIRE-1A   C H G C E G Y G H I K A E C
SIRE-1B   C H Y C G K Y G H I K P F C
DEL       C Y S C G Q P G H F K A N C
COPIA     C H H C G R E G H I K K D C
TAL-2     C W Y C K K E G H V K K D C
TNT1      C Y N C V K P G H F K R D C
HIV-1B    C W K C G K P G H I M T N C
TST1      C D H C K K Y W H T R E T C
CAMV      C W I C N I E G H Y A N E C

SIRE-1B   C H Y C G K Y G H I K P F C
SIRE-1A   C H G C E G Y G H I K A E C
DEL       C Y S C G Q P G H F K A N C
COPIA     C H H C G R E G H I K K D C
TAL-2     C W Y C K K E G H V K K D C
TNT1      C Y N C V K P G H F K R D C
TST1      C D H C K K Y W H T R E T C
HIV-1B    C W K C G K P G H I M T N C
```

FIGURE 9

| | | | | | | | | | |
|---|---|---|---|---|---|---|---|---|---|
| SIRE-1 | L | D | S | G | C | S | R | H | M | T |
| TAL-2 | L | D | S | G | C | T | S | H | M | S |
| TNT1 | V | D | T | A | A | S | H | H | A | T |
| COPIA | L | D | S | G | A | S | D | H | L | T |
| TST1 | I | D | S | R | A | S | D | H | M | T |
| DEL | I | D | T | G | S | T | H | S | F | I |
| CaMV | V | D | T | G | A | S | L | C | I | A |
| HIV-1 | L | D | T | G | R | D | D | T | V | L |

FIGURE 10 tRNA¹⁻met  3' -ACCAUAGUCUCGGUCCAAAGCU..
              |||||||||||  |    ||||
PBS      180  TGGTATCAGAGCAGGCACTCGA   201

FIGURE 11

```
SIRE-1    161 TTG..GTATC.AGAATTTCA    177
              |||  ||||| | | |||||
TsT1      266 TTGCAGTATCTAAACTTTCA    285
```

FIGURE 12

```
GCTCGCGGCC GCGAGCTCTA ATACGACTCA CTATAGGGCG      40
TCGACTCGAT CTTGTTGATG ATAAAGTTAT CACACTGGAG      80
CATGTTGACA CTGAGGAACA AATAGCAGAT ATTTTCACAA     120
AGGCATTGGA TGCAAATCAG TTTGAAAAAC TGAGGGGCAA     160
GCTGGGCATT TGTCTGCTAG AGGATTTATA GCAATTACTT     200
TTATCTGAAC GTGCTTAAAC GTTAATAGCG CGTTCTCTAC     240
TGGGCCAAAA CAAATTCGAC CGTTGCTTCA CACGTCCCTC     280
TACATTCCTC ATTCAAACTC ATATTTTCGT GGTAATCTCG     320
TTTTCAGCAT TCCCCAACAG CTCTCAGAGA TTTACGAAAC     360
CATTCCAAAG GCTCTGCTTC TCCATGGCTA CCTCACCAAA     400
AGATACTTCA TCTCCTGGTT CACCCTCTGT ACCATCATCT     440
CCATCATCCA CCAAAGCACC ATCAAACCAG GAACAACCTG     480
AATTCCATAT CCAACCCATA CAAATGATTC CTGGTCTAGC     520
CCCTGTTCCT GAGAAACTGG TCCCCATAAG ACAACAGGGA     560
GTGAAGATTT CTGAAAACCC TAGCATTGCA ACAAGTCCTA     600
GGGAATTGAC ACGGGAGATG GATAAGAAGA TCCGCAGTAT     640
TGTGAGTAGT ATTCTGAAAA ATGCTTCTGT CCCTGATGCT     680
GATAAAGATG TTCCAACATC TTCCACCCCA AATGCTGAAG     720
TCCTCTCTTC ATCCAGTAAA GAGGAATCAA CAGAGGAAGA     760
GGAACAAGCC ACAGAGGAGA CCCCTGCACC AAGGGCACCA     800
GAACCTGCTC CAGGTGACCT CATTGACCTA GAAGAAGTAG     840
```

FIGURE 13 A

```
AATCTGATGA GGAACCCATT GCCAACAAGT TGGCACCTGG    880
CATTGCAGAA AGATTACAAA GCAGAAGGG AAAAACCCCC     920
ATTACTAGGT CTGGACGAAT CAAAACTATG GCACAGAAGA    960
AGAGCACACC AATCACTCCT ACCACATCCA GATGGAGCAA   1000
AGTTGCAATC CCTTCCAAGA AGAGGAAAGA ATTTTCCTCA   1040
TCTGATTCTG ATGATGATGT CGAACTAGAT GTTCCCGACA   1080
TCAAGAGGGC CAAGAAATCT GGGAAAAAGG TGCCTGGAAA   1120
TGTCCCTGAT GCACCATTGG ACAACATTTC ATTCCACTCC   1160
ATTGGCAATG TTGAAAGGTG GAAATTTGTA TATCAACGCA   1200
GACTTGCCTT AGAAAGAGAA CTGGGAAGAG ATGCCTTGGA   1240
TTGCAAGGAG ATCATGGACC TCATCAAGGG CTGCTGGACT   1280
GCTGAAAACA GTCACCAAGT TGGGAGATGT TATGAAAGCC   1320
TAGTCAGGGA ATTCATTGTC AACATTCCCT CTGACATAAC   1360
AAACAGAAAG AGTGATGAGT ATCAGAAAGT GTTTGTCAGA   1400
GGAAAATGTG TTAGATTCTC CCCTGCTGTA ATCAACAAAT   1440
ACCTGGGCAG ACCTACTGAA GGAGTGGTGG ATATTGCTGT   1480
TTCTGAGCAT CAAATTGCCA AGGAAATCAC TGCCAAACAA   1520
GTCCAGCATT GGCCAAAGAA AGGGAAGCTT TCTGCAGGGA   1560
AGCTAAGTGT GAAGTATGCA ATCCTGCACA GGATTGGCGC   1600
TGCAAACTGG GTACCCACCA ATCATACTTC CACAGTTGCC   1640
ACAGGTTTGG GTAAATTTCT GTATGCTGTT GGAACCAAGT   1680
```

FIGURE 13 B

```
CCAAATTTAA TTTTGGAAAG TATATTTTTG ATCAAACTGT    1720
TAAGCATTCA GAATCATTTG CTGTCAAATT ACCCATTGCC    1760
TTCCCAACTG TATTGTGTGG CATTATGTTG AGTCAACATC    1800
CCAATATTTT AAACAACATT GACTCTGTGA TGAAGAAAGA    1840
ATCGGCTCTG TCCCTGCATT ACAAACTGTT TGAGGGGACA    1880
CATGTCCCAG ACATTGTCTC GACATCAGGG AAAGCTGCTG    1920
CTTCAGGTGC TGTATCCAAG GGATGCTTTG ATTGCTGAAC    1960
TCAAGGACAC ATGCAAGGTG CTGGAAGCAA CCATCAAAGC    2000
CACCACAGAG AAGAAAATGG AGCTGGAACG CCTGATCAAA    2040
AGACTCTCAG ACAGTGGCAT TGATGATGGT GAAGCAGCTG    2080
AGGAAGAAGA AGAAGCCGCT GAGGAAGAGA AAGATGCAGC    2120
AGAAGATACA GAATCAGATG ATGATGATTC TGATGCCACC    2160
CCATGACCAT CAGACCTTTA TTTTTGCTTT TTACTCTTAC    2200
TAGCTATAGG GCATGTCCCT TTGAACAATT GATTGCTATT    2240
GGTCTGTAAT ATTTGCATGC ATTCTACTTT TGTCAAATTC    2280
TGTCTAAAAA GGGGATATAT ATTATGCATG ATTTTGAGTA    2320
GTAGATACTA TGTTGCAATA GTATATTATG CATAATTTAT    2360
GATTTTGAGT AGTAGGATAC GATGTATGCA TGATTCATGA    2400
TTTTGAGGGG GAGTTGTAAG TATATGATTT TGAGGGGGAG    2240
TAGTATCTGA TGATGCTGAT AGAAGATGGC ATGGAGACAG    2280
GGGGAGCAGA AAGCTGATGT CACGTGAGAT GTCTTGACAT    2520
```

FIGURE 13 C

```
CCTGGAAACG ACTTGCAACT TGCAGAATTT TGCTGTCGCC    2560
CCTACAGATA CCGCTGTGCT TGATTACTCT GATAATGAAA    2600
GTTGCTGATC CCACTTGCAT AACTGCTCGT ACCTGCTCAG    2640
GAAGTGTCTA AGTATGTTTT AGACAAAATT TGCCAAAGGG    2680
GGAGATTGTT AGTGCTTAGC TTTACTGAGT TTTAAAAGAT    2720
TGGCTAAAAT TTTGTTAAAA CATAAGCACT TAGACAATGA    2760
AGGAAAGCTG GAGTTGCTGC ACAGGATGTC CAACGTTATG    2800
TCAAGGAATC AGATTGGGCT CCACAATGCA CAAGGCAAGA    2840
TAAAAGGTCA AATGAAGAAT TGAAGCTGCA GGATCCACGA    2880
TGTCGGATAC AATGTCCAGG ACATCCTGCC CGAAAATACT    2920
GGACACATAA ATCTGTTATA TCTTTAACAG ATTAATGTGC    2960
AGTTAGCAAC AGATTTGGCG ATCTATCTTT AGGAACGAAT    3000
TAAAAGATAA TTAAAGTTCG AATTACAAAC TTGAATAGTT    3040
CGTTCAGGGA TTAAAGATTA AAGATAAAAA CTAAAAGATC    3080
AAACTGTATC TTTTAGATCT TTAAGTGCAG ATTTTTCAGG    3120
AGAATGATAG ATCTTATCCA GCGCAAGATG TTGCAGCCCA    3160
GATACGCACA CTGCTATATA AACATGAAGG CTGCACGAGT    3200
TTTCTACCAA GTCCGGGATT GAAGAGTTAT TTTGTGAGTT    3240
TTGGGACTTG AGTGTTTTGT GAGCCACCTT GATGTTACCC    3260
TAACATCAAG TGTTGGACCT GAGTGTGTAG AGTTGATCTC    3300
TATTGTTCAG AGAGCAATCT CTGGTGTGTC TTTGATTTAT    3360
```

FIGURE 13 D

```
TTGTAAACAC GGGAGAGTGA TTGAGAGGGA GTGAGAGGGG    3400
TTCTCATATC TAAGAGTGGC TCTTAGGTAG AGGTTGCACG    3440
GGTAGTGGTT AGGTGAGAAG GTTGTAAACA GTGGCTGTTA    3480
GATCTTCGAA CTAACACTAT TTTAGTGGAT TTCCTCCCTG    3520
GCTTGGTAGC CCCCAGATGT AGGTGAGGTT GCACCGAACT    3560
GGGTTAACAA TTCTCTTGTG TTATTTACTT GTTTAATCTG    3600
TTCATACTGT CAAATATAAT CTGCATGTTC TGAAGCGTGA    3640
TGTCGTGACA TCCGGTACGA CATCTGTCAT TGGTATCAGA    3680
ATTTCATGCT GCAAATATTT ACAATAGACC TCCTCAACCT    3720
CAACAGCAAA ATCAACCACA GCAGAACAAT TATGACCTCT    3760
CCAGCAACAG ATACAACCCT GGATGGAGGA ATCACCCTAA    3800
CCTCAGATGG TCCAGCCCTC AGCAACAACA ACAGCAGCCT    3840
GCTCCTTCCT TCCAAAATGC TGTTGGCCCA AGCAGACCAT    3880
ACATTCCTCC ACCAATCCAA CAACAGCAAC AACCCCAGAA    3920
ACAGCCAACA GTTGAGGCCC TCCACAACTT CCTTCGAAGA    3960
ACTTGTGAGG CAAATGACTA TGCAGAACAT GCAGTTTCAG    4000
CAAGAGACTA GAGCCTCCAT TCAGAGCTTA ACCAATCAGA    4040
TGGGACAATT GGCTACCCAA TTGAATCAAC AACAGTCCCA    4080
GAATTCTGAC AAGTTGCCTT CTCAAGCTGT CCAAAATCCC    4120
AAAAATGTCA GTGCCATTTC ATTGAGGTCG GGAAAGCAGT    4160
GTCAAGGACC TCAACCCGTA GCACCTTCCT CATCTGCAAA    4200
TGAACCTGCC AAACTTCACT CTAC                    4224
```

```
  1  TLIARSLLGQ  NKFDRCFTRP  STELIOTHIE  VVISFSAEPN  SSQRFTKPFQ
 51  RLCFSMATSP  KDTSSPGSPS  VPSSPSSTKA  PSNQEQPEFH  IQPIQMIPGL
101  APVPEKLVPI  RQQGVKISEN  PSIATSPREL  TREMDKKIRS  IVSSILKNAS
151  VPDADKDVPT  SSTPNAEVLS  SSSKEESTEE  EEQATEETPA  PRAPEPAPGD
201  LIDLEEVESD  EEPIANKLAP  GIAERLQSRK  GKTPITRSGR  IKTMAQKKST
251  PITPTTSRWS  KVAIPSKKRK  EFSSSDSDDD  VELDVPDIKR  AKKSGKKVPG
301  NVPDAPLDNI  SFHSIGNVER  WKFVYQRRLA  LERELGRDAL  DCKEIMDLIK
351  GCWTAENSHQ  VGRCYESLVR  EFIVNIPSDI  TNRKSDEYQK  VFVRGKCVRF
401  SPAVINKYLG  RPTEGVVDIA  VSEHQIAKEI  TAQVQHWPKK  GKLSAGKLSV
451  KYAILHRIGA  ANWVPTNHTS  TVATGLGKFL  YAVGTKSKFN  FGKYIFDQTV
501  KHSESFAVKL  PIAEPPVLCG  IMLTOHPNIL  NNIDSVMKKE  SALSLHYKLF
551  EGTHVPDIVS  TSGKAAASGA  VSKGCFDC*
```

FIGURE 16

```
ORF1     1 .SRPPAL.IRLTIGRRLDLVDDKVITLEHVDTEEQIADIFTKALDANQFE 48
            .|::  .|:.  ::|    :..|:::.||.|.||||||:|.|..|
copia 1345 HKRAKHIDIKYHFAR..EQVQNNVICLEYIPTENQLADIFTKPLPAARFV 1392

49 KLRGKLGICLLEDL*
      ||:|||  |||:|
 1393 ELRDKLG..LLQDDQSNAE*
```

Sense strand
| | | |
|---|---|---|
| F1 (M13/pUC forward) | | 5'-CCCAGTCACGACGTTGTAAAACG-3' |
| F2 (aka pucf2) | 227-246 | 5'-AGCGCGTTCTCTACTGGGCC-3' |
| F3 (aka pucf3a) | 448-467 | 5'-CCACCAAAGCACCATCAAAC-3' |
| F4 (aka pucf4) | 950-969 | 5'-GGCACAGAAGAAGAGCACAC-3' |
| F5 (aka pucf5) | 1242-1261 | 5'-TGCAAGGAGATCATGGACCT-3' |
| F6 (aka pucf6) | 1586-1605 | 5'-CACAGGATTGGCGCTGCAAA-3' |
| F7 (aka AM01) | 3515-3543 | 5'-TCCCTGGCTTGGTAGCCCCCAGATGTAGG-3' |
| F8 (aka 3flankA) | 3936-3956 | 5'-GGCCCTCCACAACTTCCTTCG-3' |

Complementary strand
| | | |
|---|---|---|
| R1 (M13/pUC reverse) | | 5'-AGCGGATAACAATTTCACACAGG-3' |
| R2 (aka 3flankB) | 4196-4177 | 5'-CAGATGAGGAAGGTGCTACG-3' |
| R3 (aka AM02) | 3563-3534 | 5'-CCCAGTTCGGTGCAACCTCACCTACATCTG-3' |
| R4 (aka LTR2a) | 3268-3249 | 5'-GGTGGCTCACAAAACACTCA-3' |
| R5 (aka LTR3) | 2927-2908 | 5'-TGTGTCCAGTATTTTCGGGC-3' |
| R6 (aka LTR4) | 2453-2434 | 5'-TCATCAGATACTACTCCCCC-3' |
| R7 (aka pucfcom3) | 602-581 | 5'-CCTAGGACTTGTTGCAATGCTA-3' |
| R8 (aka pucfcom2) | 292-273 | 5'-ATGAGGAATGTAGAGGGACG-3' |

FIGURE 20

Tertiary structure class: none

Sequence of 2:
TLIARSLLGQNKFDRCFTRPSTFLIQTHIFVVISFSAFPNSGQRFTKPFQRLCFSMATSPKDTSSPGSPSVP
SSPSSTKAPSNQEQPEFHIQPIQMIPGLAPVPEKLVPIRQQGVKISENPSLATSPRELTREMDKKIRSIVGS
ILRNASVPDADKDVPISSTPNAEVLSSSSKEESTEEEQATEETPAPRAPEPAPGDLIDLEEVESDEEPLAN
KLAPGIAERLQSRKGKTPITRSGRIKTMAQKSTPITPTTSRWKSKVAIPSKKRKEFSSSDSDDDVELDVPDI
KRAKKSGKKVPGNVPDAPLDNISFHSIGNVERWKFVYQRRLALERELQRDALDCKEIMDLIKGCWTAENSHQ
VGRCYESLVREFIVNIPSDITNRKSDEYQKVFVRGKCVRFSPAVINKYLGRPTBGVVDIAVSEHQIAKEITA
KQVQHWPKKGKLSAGKLSVKYAILHRIGAANWVPTNHTSTVATGLGKPLYAVGIKSKFNFGKYIFDQIVKHIS
ESFAVKLPIAFPTVLCGIMLSQHPNILNNIDSVMKKSALSLIIYKLFEGTHVPDIVSTSGKAAASGAVSKGC
FDCTQGEMQGAGSNHQSHHRKRNGAGTPDQKTLRQWH Secondary structure prediction (H = helix, E = strand, - = no prediction):
--HHHHH---------EEEEEEEEEE----------------HHHHE------------
HH-------EEE-----HHHH----E----E------HHHHHHHHHHEEHH-----HH-
----HHHHHH------------E----HHHHH-HHHHHH------H-----------
HHHH-------E-----------HHHEEE----------H-----EEEEHHHHHHHHHHH---
----HHHHHHHHEE-------H---HHEHHEEERH-----------EEHHHHHHHSERH-------EEE-HH-
HHH-H-------EE--E-------E--HHHHHHHHHHHHHH-----EEE-----HEH-
HHHHHE----------HHHK-

```
GagR2 2202/2205    ....GTTGCTGCACAATGCACAAGGCAAGATAA
                      ||||||||||||||||||||||||||||||||
GagR1 2067 GACTTCGTTATGTCAAGGAATAAGATCGGGCTGCACAATGCACAAGGCAAGATAA
              ||||||||||||||||||||||||  ||||  |||||  |||||||||||||
LTR2  2789 TCCAACGTTATGTCAAGGAATCAGATTGGGCTCCACAATGCACAAGGCAAGATAA

GagR2 2231         ......AAGAAGTGAAGCTGCAGGATCCACGATGTCGGATACGATGTCCA
                         ||||||||||||||||||||||||||||||||| ||||||||||||
GagR1 2122 AATGTCAAATGAAGAATTGAAGCTGCAGGATCCATGATGTCGGATACAATGTCCA
              ||||||||  ||||||  ||||||||||||||||||||||||||| ||||||
LTR2  2844 AAGGTCAAATGAAGAATTGAAGCTGCAGGATCCACGATGTCGGATACAATGTCCA

GagR2 2275 AGACATCTGGCCCGAAAATACTGGA         GTT....2204   GagR1
              ||||||||||||||||||||||||         >---
GagR1 2177 GGACATCCTGCCCGAAAATACTGGA         CACATAAATCTGTTATATCTTTAACAGAT
              |||||| ||||||||| ||||||         ||||||||||||||||||||||||||||
LTR2  2899 GGACATCCTGCCCGAAAAATACTGGA--CACATAAATCTGTTATATCTTTAACAGAT

GagR2 2329 TATTGTGCAGTTAGCAACAGGTTAGACGATCTATCTTTAGGAACGAACTCTTCTAG
              || |||||||||||||||||||||| |||||| ||||||||||||||||  ---
LTR2  2953 TAATGTGCAGTTAGCAACAGATTGGCGATCTATCTTTAGGAACGAATTAAAAGAT
```

```
487  AGAGGAAAGGACTTTCTGTATGTCGGTCTGATGATACAGAGAGTGAACAA  438
     ||||||||||||||| ||||||| ||||||| ||||||||||||||||||
1200 AGAGGAAAGGACTTTGTGTATGTCGGTCTGATGATACAGAGAGTGAACAA  1249

437  G.AAGTGATTCTGACAGAGATGTGAATGCACTCACTGGGAGATTTGAAATC  389
      | |||||||||||||||| | |||||||||||||||||||||||||||
1250 GAAAGTGATTCTGACAGAGATGTGAATGCACTCACTGGGAGATTTGAAATC  1299

388  TGCTGAAGATTCAAGTGATACAGATAGTGAAATCACTTTTGATGAGCTTG  339
     |||||||||||||||||||||| ||||||||||||||| |||||||||||
1300 TGCTGAAGATTCAAGTGATACAGACAGTGAAATCACTTTTGATGAGCTTG  1349

338  CTATATCCTATAGAGAACTATGCATCAAAAGTGAGAAGATTCTTCAGCAA  289
     || | |||||||||||||||||||||||||||||||||||||||||||||
1350 CTACATCCTATAGAGAACTATGCATCAAAAGTGAGAAGATTCTTCAGCAA  1399

288  GAAGCACAACTAAAGAAGTCATTGCAAATCTGGAGGCTGAGAAGGAGGC  239
     ||||||||||||| |||||||||||||||||||| |||||||||||||||
1400 GAAGCACAACTGAAGAAGTCATTGCAAATCTGGAGGCTGAGAAGGAGGC  144
```

FIGURE 22 B

```
238  ACATGAAGAGGAAATCTCTGAACTTAAGGAGAAATTGGTTTTCTGAACT  189
     ||||||||||||||||||| |||||||||||||||||||||||||||||
1450 ACATGAAGAGGAGATCTCTGAGCTTAAAGGAGAAGTTGGTTTTCTGAACT 1499

188  CTAAACTGGAAAACATGACAAAATCAATAAAGATGCTGAATAAAGGCTCA  139
     |||||||||||  |||||| ||||||||||||||||||||||||||||
1500 CTAAACTGGAAAACATGACAAAATCAATAAAGATGCTGAATAAAGGCTCA 1549

138  GATTGCTTGATGAGGTGCTACAGCTTGGGAAGAATGTTGGAAACCAGAG   89
     ||| ||||||||||||||||||||||||||||||||||||||||||||
1550 GATATGCTTGATGAGGTGCTACAGCTTGGGAAGAATGTTGGAAACCAGAG 1599

88   AGGACTTGGATTTAATCATAAATCTGCTGGCAGAACAACCATGACATAAT  39
     ||||||||||| ||||||||||||||||||||||||||||||||||||
1600 AGGACTTGGGTTTAATCATAAATCTGCTGGCAGAATAACCATGACAGAAT 1649

38   TTGTTCCTGCCAAAAACAGCACTGCACCCGATCCAATA.........     1
     |||||||||||||||| ||||||||| ||  ||
1650 TTGTTCCTGCCAAAATCAGCACTGGAGCCACGATGTCACAACATCGGTCT 1699
```

FIGURE 22 C

```
  1 TLIARSLLGQNKFDRCFTRPSTFLIQTHIFVVISFSAFPNSSQRFTKPFQ
 51 RLCFSMATSPKDTSSPGSPSVPSSPSSTKAPSNQEQPEFHIQPIQMIPGQ
101 APVPEKLVPKRQQGVKISENPSIATSPRVDTEMDKKIRSIVSSILKNASV
151 PDADKDVPTSSTPNAEVLSSSSKEESTEEEEQATEETPAPRAPEPAPGDL
201 IDLEEVESDEEPIANKLAPGIAERLQSRKGRTPITRSGRIKTMAQKKSTP
251 ITPTTSRWSKVAIPSKKRKEFSSSDSDDDVELDVPDIKRAKKSGKKVPGN
301 VPDAPLDNISFHSIGNVERWKFVYQRRLALERELGRDALDCKEIMDLIKA
351 AGLLKTVTKLGDCYESLVREFIVNIPSDITNRKSDEYQKVFVRGKCVRFS
401 PAVINKYLGRPTEGVVDIAVSEHQIAKEITAKQVQHWPKKGKLSAGKLSV
451 KYAILHRIGAANWVPTNHTSTVATGLGKFLYAVGTKSKFNFGKYIFDQTV
501 KHSESFAVKLPIAFPTVLCGIMLSQHPNILNNIDSVMKRESALSLHYKLF
551 EGTHVPDIVSTSGKAAASGAVSKDALIAELKDTCKVLEATIKATTEKKME
601 LERLIKRLSDSGIDDGEAAEEEEAAEEEKDAAEDTESDDDDSDATP*
```

FIGURE 23

(4.3H) ——— ← *Gag*, 5' Flank, LTR
(4.1H) ——— ← *Env*, 5' Flank (2.7H) ——— ← 5' Flank, LTR, 3' Flank (2.2H) ———
(2.1H) ———

(1.5H) ——— ← *Env*, 5' Flank (1.1H) ——— ← 3' Flank
(1.0H) ———

FIGURE 25

A. PUC Forward    5'-CCC AGT CAC GAC GTT GTA AAA CG-3'
B. PUC Reverse    5'-AGC GGA TAA CAA TTT CAC ACA GG-3'

C. EG4.1H-620     5'-CTC ATG AGT TCT CTG CAG CC-3'
D. EG4.1H-1081    5'-GAC AAT GTT GCA GAT ACA GCT AAA AGT GC-3'
E. EG4.1H-1617    5'-CCA GAT GGA TGT GAA GAG CG-3'
F. EG4.1H-2070    5'-TGG GAT GGA AAA TGC CAG C-3'
G. EG4.1H-2468    5'-AGA ACT GTG TGT CCC TAT CC-3'

H. EG4.1H-2734c   5'-CCT CAG TGT CAA CAT GCT CC-3'
I. EG4.1H-2327c   5'-ATC CCA TAG TCA CTG GTG CC-3'
J. EG4.1H-1788c   5'-CTC TGT TAG CCT TTC ATA CC-3'
K. EG4.1H-1253c   5'-CTT GAT CTT GTA GTG ACT CC-3'
L. EG4.1H-816c    5'-ATA CAG TGT GGT TGG AGT CC-3'
M. EG4.1H-520c    5'-GAA GTC TTA GAC TCA ACT CC-3'

FIGURE 30

```
  1  GATGAAGGAT TCAATGTAGA CTTCACAGAG TCAGAATGCT TGATGACAAA
 51  AGAGAAGAGA GAAGTCCTAA TGAAGGGCGG CAGATCAAAG GACAACTGTT
101  ACCTGTGGAC ACCTCAAGAA ACCAGTTACT CCTCCACATG TCTATTCTCC
151  AAAGAAGATG AAGTCAAAAT ATGGCATCAA AGATTTGGAC ATCTGCACTT
201  AGGAGGCATG AAGAAAATCA TTGACAAAGG TGCTGTTAGA GGCATTCCCA
251  ATCTGAAAAT AGAAGAAGGC AGAATCTGTG GTGAATGTCA GATTGGAAAG
301  CAAGTCAAGA TGTCCAACCA GAAGCTTCAA CATCAGACCA CTTCCAGGGT
351  GCTGGAACTA CTTCACATGG ACTTGATGGG GCCTATGCAA GTTGAAAGCC
401  TTGGAAGAAA AAGGTATGCC TATGTTGTTG TGGATGATTT CTCCAGATTT
451  ACCTGGGTCA ACTTTATCAG AGAGAAATCA GACACCTTTG AAGTATTCAA
501  GGAGTTGAGT CTAAGACTTC AAAGAGAAAA AGACTGTGTC ATCAAGAGAA
551  TCAGGAGTGA CCATGGCAGA GAGTTTGAAA ACAGCAAGTT TACTGAATTC
601  TGCACATCTG AAGGCATCAC TCATGAGTTC TCTGCAGCCA TTACACCACA
651  ACAAAATGGC ATAGTTGAAA GGAAAAACAG GACCTTGCCA GAAGCTGCTA
701  GGGTCATGCT TCATGCCAAA GAACTTCCCT ATAATCTCTG GGCTGAAGCC
751  ATGAACACAG CATGCTACAT CCACAACAGA GTCACACTTA GAAGAGGGAC
801  TCCAACCACA CTGTATGAAA TCTGGAAAGG GAGGAAGCCA ACTGTCAAGC
851  ACTTCCACAT CTGTGGAAGT CCATGTTACA TTTTGGCAGA TAGAGAGCAA
901  AGGAGAAAGA TGGATCCCAA GAGTGATGCA GGGATATTCT GGGATACTC
```

FIGURE 31 A

```
 951  TACAAACAGC AGAGCATATA GAGTATTCAA TTCCAGAACC AGAACTGTGA
1001  TGGAATCCAT CAATGTGGTT GTTGATGATC TAACTCCAGC AAGAAAGAAG
1051  GATGTCGAAG AAGATGTCAG AACATCGGGA GACAATGTTG CAGATACAGC
1101  TAAAAGTGCA GAAAATGCAG AAAACTCTGA TTCTGCTACA GATGAACCAA
1151  ACATCAATCA ACCTGACAAG AGACCCTCCA TTAGAATCCA GAAGATGCAC
1201  CCCAAGGAGC TGATTATAGG AGATCCAAAC AGAGGAGTCA CTACAAGATC
1251  AAGGGAGATT GAGATTATCT CCAATTCATG TTTTGTCTCC AAAATTGAGC
1301  CCAAGAATGT GAAAGAGGCA CTGACTGATG AGTTCTGGAT CAATGCTATG
1351  CAAGAAGAAT TGGAGCAATT CAAAAGGAAT GAAGTTTGGG AGCTAGTTCC
1401  TAGGCCCGAG GGAACTAATG TGATTGGCAC CAAGTGGATC TTCAAGAACA
1451  AAACCAATGA AGAAGGTGTT ATAACCAGAA ACAAGGCCAG ACTTGTTGCT
1501  CAAGGCTACA CTCAGATTGA AGGTGTAGAC TTTGATGAAA CTTTTGCCCC
1551  TGGTGCTAAA CTTGAGTCCA TCAGACTGTT ACTTGGTGTA GCTTGCATCC
1601  TCAAATTCAA GCTGTACCAG ATGGATGTGA AGAGCGCATT TCTGAATGGA
1651  TACCTGAATG AAGAAGCCTA TGTGGAGCAG CCAAAGGGAT TGTAGATCC
1701  AACTCATCCA GATCATGTAT ACAGGCTCAA GAAGCTCTGC TATGGATTGA
1751  AGCAAGCTTC AAGAGCTTGG TATGAAAGGC TAACAGAGTT CCTTACTCAG
1801  CAAGGGTATA GGAAGGGGGG GATTGACAAG ACCCTTTTTG TTAAACAAGA
1851  TGCTGGAAAA TTGATGATAG CACAGATATA TGTTGATGAC ATTGTGTTTG
1901  GAGGGATGTT GAATGAGATG CTTCGACATT TTGTCCAACA GATGCAATTT
1951  GAATTTGAGA TGAGTTTTGT TGGAGAGCTG AATTATTTTT TGGGAATCCA
2001  AGTGAAGCAG ATGGAAGAAT CCATATTCCT TTCACAAAGC AAGTATGCAA
2051  AGAACATTGT CAAGAAGTTT GGGATGGAAA ATGCCAGCCA TAAAAGAACA
2101  CCTGCACCTA ATCAATTGAA GCTGTCAAAA GATGAAGCTG GCACCAGTGT
2151  TGATCAAAGT TTGTACAGAA GCATGATTGG GAGCTTAATA TATTTAACAG
2201  CTAGCAGACC TGACATCACC TATGCAGTAG GTGGTTGTGC AAGATATCAA
2251  GCCAATCCTA AGATAAGTCA CTTGAATCAA GTAAAGAGAA TTTTGAAATA
```

FIGURE 31 B

```
2301  TGTAAATGGC ACCAGTGACT ATGGGATTAT GTACTGTCAT TGTTCAGATT

2351  CAATGCTGGT TGGGTATTGT GATGCTGATT GGGCTGGAAG TGTAGATGAC

2401  AGAAAAAGCA CTTTTGGTGG ATGTTTTTAT TTGGGAACCA ATTTTATTTC

2451  ATGGTTCAGC AAGAAGCAGA ACTGTGTGTC CCTATCCACT GCAGAAGCAG

2501  AGTATATTGC AGCAGGAAGC AGCTGTTCAC AACTAGTTTG GATGAAGCAG

2551  ATGCTCAAGG AGTACAATGT CGAACAAGAT GTCATGACAT TGTACTGTGA

2601  CAACTTGAGT GCTATTAATA TTTCTAAAAA TCCTGTTCAA CACAGCAGAA

2651  CCAAGCACAT TGACATTAGA CATCACTATA TTAGAGATCT TGTTGATGAT

2701  AAAGTTATCA CACTGGAGCA TGTTGACACT GAGGAACAAA TAGCAGATAT

2751  TTTCACAAAG GCATTGGATG CAAATCAGTT TGAAAAACTG AGGGGCAAGC

2801  TGGGCATTTG TCTGCTAGAG GATTTA
```

FIGURE 31 C

```
  1  DEGFNVDFTE  SECLMTKEKR  EVLMKGGRSK  DNCYLWTPQE  TSYSSTCLFS
 51  KEDEVKIWHQ  RFGHLHLGGM  KKIIDKGAVR  GIPNLKIEEG  RICGECQIGK
101  QVKMSNQKLQ  HQTTSRVLEL  LHMDLMGPMQ  VESLGRKRYA  YVVVDDFSRF
151  TWVNFIREKS  DTFEVFKELS  LRLQREKDCV  IKRIRSDHGR  EFENSKFTEF
201  CTSEGITHEF  SAAITPQQNG  IVERKNRTLP  EAARVMLHAK  ELPYNLWAEA
251  MNTACYIHNR  VTLRRGTPTT  LYEIWKGRKP  TVKHFHICGS  PCYILADREQ
301  RRKMDPKSDA  GIFLGYSTNS  RAYRVFNSRT  RTVMESINVV  VDDLTPARKK
351  DVEEDVRTSG  DNVADTAKSA  ENAENSDSAT  DEPNINQPDK  RPSIRIQKMH
401  PKELIIGDPN  RGVTTRSREI  EIISNSCFVS  KIEPKNVKEA  LTDEFWINAM
451  QEELEQFKRN  EVWELVPRPE  GTNVIGTKWI  FKNKTNEEGV  ITRNKARLVA
501  QGYTQIEGVD  FDETFAPGAK  LESIRLLLGV  ACILKFKLYQ  MDVKSAFLNG
551  YLNEEAYVEQ  PKGFVDPTHP  DHVYRLKKLC  YGLKQASRAW  YERLTEFLTQ
601  QGYRKGGIDK  TLFVKQDAGK  LMIAQIYVDD  IVFGGMLNEM  LRHFVQQMQF
651  EFEMSFVGEL  NYFLGIQVKQ  MEESIFLSQS  KYAKNIVKKF  GMENASHKRT
701  PAPNQLKLSK  DEAGTSVDQS  LYRSMIGSLI  YLTASRPDIT  YAVGGCARYQ
751  ANPKISHLNQ  VKRILKYVNG  TSDYGIMYCH  CSDSMLVGYC  DADWAGSVDD
801  RKSTFGGCFY  LGTNFISWFS  KKQNCVSLST  AEAEYIAAGS  SCSQLVWMKQ
851  MLKEYNVEQD  VMTLYCDNLS  AINISKNPVQ  HSRTKHIDIR  HHYIRDLVDD
901  KVITLEHVDT  EEQIADIFTK  ALDANQFEKL  RGKLGICLLE  DL
```

FIGURE 32

```
SIRE-1    1  ............................DEGFNVDFTESE.CL  14
              : |:|   ||:  :  ::
Opie-2   86  ............................NMGYNCLFTNIDVSV 100

SIRE-1   15  MTKEKREVLMKGGRSKDNCYLWTPQETSYSSTCLFSKEDEVKIWHQRFGH  64
              : :    : :||       : :  : |       ||: |     :|| |::|
Opie-2  101  FRRCDGSLAFKGVLDGKLYLVDFAKEEAGLDACLIAKTSMGWLWHRRLAH 150

SIRE-1   65  LHLGGMKKIIDKGAVRGIPNLKIEEGRICGECQIGKQVKMSNQKLQHQTT 114
              : :   : |::    : | |: |: :| :| |: || ||||  |::     ||
Opie-2  151  VGMKNLHKLLKGEHVIGLTNVQFEKDRPCAACQAGKQVGGSHHTKNVMTT 200

SIRE-1  115  SRVLELLHMDLMGPMQVESLGRKRYAYVVVDDFSRFTWVNFIREKSDTFE 164
              ||  ||:||||:||:    |:|    :|:  |:||||||||||| |:  |||:| :
Opie-2  201  SRPLEMLHMDLFGPVAYLSIGGSKYGLVIVDDFSRFTWVFFLQEKSETQG 250

SIRE-1  165  VFKELSLRLQREKDCVIKRIRSDHGREFENSKFTEFCTSEGITHEFSAAI 214
              :|  :    | | |  :  :|:||||:| || |    ||    ||| |||||:
Opie-2  251  TLKRFLRRAQNEFELKVKKIRSDNGSEFKNLQVEEFLEEEGIKHEFSAPY 300

SIRE-1  215  TPQQNGIVERKNRTLPEAARVMLHAKELPYNLWAEAMNTACYIHNRVTLR 264
              ||||||:||||||||| : || ||       |  :|  ||:||||   ||| |:
Opie-2  301  TPQQNGVVERKNRTLIDMARTMLGEFKTPECFWTEAVNTACHAINRVYLH 350

SIRE-1  265  RGTPTTLYEIWKGRKPTVKHFHICGSPCYILADREQRRKMDPKSDAGIFL 314
              |    | ||::   |  ||| |    |::   || ||||   ::    |: ||     |::|
Opie-2  351  RILKNTSYELLTGNKPNVSYFRVFGSKCYILVKKGRNSKFAPKAVEGFLL 400

SIRE-1  315  GYSTNSRAYRVFNSRTRTVMESINVVVDDLTPARKKDV.......EEDVR 357
              ||  |  :||||||      |   |  :|| |:      : :|        |||:
Opie-2  401  GYDSNTKAYRVFNKSSGLVEVSGDVVFDETNGSPREQVVDCDDVDEEDIP 450

SIRE-1  358  TS............................GDNVADTAKSAENAE 374
              |                                   :: | :     : : :
Opie-2  451  TAAIRTMAIGEVRPQEQDEREQPSPSTMVHPPTQDDEQVHQQEVCDQGGA 500

SIRE-1  375  NSDSATDEPNINQPDKRPSIRIQKMH......................400
              | :|    |    ||: |
Opie-2  501  QDDHVLEEEAQPAPPTQVRAMIQRDH..................... 526
```

FIGURE 33

```
SIRE-1    1   ........................PKELIIGDPNRGVTTRSREIEIIS   24
                                      | : |:||  :|||||||  :::
Opie-2  527   ........................PVDQILGDISKGVTTRSRLVNFCE  550

SIRE-1   25   NSCFVSKIEPKNVKEALTDEFWINAMQEELEQFKRNEVWELVPRPEGTNV   74
              : :|||  |||   | ||| |   |: |||||: |||||| |||||   ||
Opie-2  551   HNSFVSSIEPFRVEEALLDPDWVLAMQEELNNFKRNEVWTLVPRPKQ.NV  599

SIRE-1   75   IGTKWIFKNKTNEEGVITRNKARLVAQGYTQIEGVDFDETFAPGAKLESI  124
              :||||:|:||  :|  ||:||||||||| || |: |:||:||||| |:||||
Opie-2  600   VGTKWVFRNKQDERGVVTRNKARLVAKGYAQVAGLDFEETFAPVARLESI  649

SIRE-1  125   RLLLGVACILKFKLYQMDVKSAFLNGYLNEEAYVEQPKGFVDPTHPDHVY  174
              |:||:  |    |:|||||||||||| : || ||||| || |   ||||:
Opie-2  650   RILLAYAAHHSFRLYQMDVKSAFLNGPIKEEVYVEQPPGFEDERYPDHVC  699

SIRE-1  175   RLKKLCYGLKQASRAWYERLTEFLTQQGYRKGGIDKTLFVKQDAGKLMIA  224
              :|  |  |||||| ||||| | :||   ::: |   | |||·|   |  |::
Opie-2  700   KLSKALYGLKQAPRAWYECLRDFLIANAFKVGKADPTLFTKTCDGDLFVC  749

SIRE-1  225   QIYVDDIVFGGMLNEMLRHFVQQMQFEFEMSFVGELNYFLGIQVKQMEES  274
              ||||||:||:     |  | |    ||||::|||||||||:||||: ::
Opie-2  750   QIYVDDIIFGSTNQKSCEEFSRVMTQKFEMSMMGELNYFLGFQVKQLKDG  799

SIRE-1  275   IFLSQSKYAKNIVKKFGMENASHKRTPAPNQLKLSKDEAGTSVDQSLYRS  324
              |:||  ||    :::|:|||  :|   :||   :    : :|  ||||  |||
Opie-2  800   TFISQTKYTQDLLKRFGMKDAKPAKTPMGTDGHTDLNKGGKSVDQKAYRS  849

SIRE-1  325   MIGSLIYLTASRPDITYAVGGCARYQANPKISHLNQVKRILKYVNGTSDY  374
              |||||:|| ||||||     |   |||:| :||  :||  |||||:|: :|   :
Opie-2  850   MIGSLLYLCASRPDIMLSVCMCARFQSDPKECHLVAVKRILRYLVATPCF  899

SIRE-1  375   GIMYCHC..........................................  381
              |: |
Opie-2  900   GLWYPKG..........................................  906
```

FIGURE 34

```
SIRE-1     1 ......SDSMLVGYCDADWAGSVDDRKSTFGGCFYLGTNFISWFSKKQNC 44
                   |    ||||:| |:||: ||||| | | :||  ::|| ||||  :
Opie-2   901 LWYPKGSTFDLVGYSDSDYAGCKVDRKSTSGTCQFLGRSLVSWNSKKQTS 950

SIRE-1    45 VSLSTAEAEYIAAGSSCSQLVWMKQMLKEYNVEQDVMTLYCDNLSAINIS 94
             | ||||||||:||| :| ||:||:| |:::  :   : | ||| ||| :
Opie-2   951 VALSTAEAEYVAAGQCCAQLLWMRQTLRDFGYNLSKVPLLCDNESAIRMA 1000

SIRE-1    95 KNPVQHSRTKHIDIRHHYIRDLVDDKVITLEHVDTEEQIADIFTKALDAN 144
             |||:||||||||||||:||  :    | : || ||:|:||||||:||
Opie-2  1001 ENPVEHSRTKHIDIRHHFLRDHQQKGDIEVFHVSTENQLADIFTKPLDEK 1050

SIRE-1   145 QFEKLRGKLGICLLEDLXNPXP 166
                | :||: | :     :|
Opie-2  1051 TFCRLRSELNVLDSRNLD.... 1068
```

FIGURE 35

PLANT RETROVIRAL POLYNUCLEOTIDES AND METHODS FOR USE THEREOF

CROSS-REFERENCE TO RELATED APPLICATIONS

This application claims the benefit of U.S. Provisional Application No. 60/025,853, filed Sep. 9, 1996.

FIELD OF INVENTION

The present invention relates generally to retroviruses, pro-retroviral polynucleotides including pro-retroviral DNA, pro-retroviral-like DNA and more specifically to recombinant vectors derived therefrom for use in delivering genetic information to susceptible target plant cells.

BACKGROUND OF INVENTION

Repetitive DNA sequences are a common feature of the genomes of higher eukaryotes. Repetitive DNA family members in animals and higher plants are tandemly repeated or interspersed with other sequences (Walbot and Goldberg, 1979; Flavell, 1980), and may constitute more than 50% of the genome (Walbot and Goldberg, 1979). Estimates of the proportion of repetitive DNA in the soybean genome range from 36% to 60% (Goldberg, 1978; Gurley et al., 1979).

High copy-number repeats on the order of $10^5$ per haploid genome comprise only 3% of the soybean genome, whereas moderately repetitive sequences with copy-numbers in the $10^3$ range occupy 30–40% of the genome (Goldberg, 1978). Electron micrographic examination of these moderately repetitive sequences demonstrate that they average about 2 kb in length; however, 4% of those observed exceed 11 kb (Pellegrini and Goldberg, 1979).

Most of the highly repetitive sequences in higher eukaryotic genomes are relatively short and are organized in tandem arrays. For example, the chromosomal region adjacent to the centromere in higher eukaryotes is composed of very long blocks of highly repetitive DNA, called satellite DNA, in which simple sequences are repeated thousands of times or more. Tandemly repeated elements found in the soybean genome also include the ribosomal RNA (rRNA)-encoding genes. The approximately 800 rDNA copies are organized as one or more clusters of tandemly repeated 8-kb or 9-kb units (Friedrich et al., 1979; Varsanyi-Breiner et al., 1979).

The genomes of most higher eukaryotes also contain highly repetitive sequences that are distributed evenly throughout the genome, interspersed with longer stretches of unique (or moderately repetitive) DNA. These interspersed repetitive DNA elements are variable in length, are recognizably related but not precisely conserved in sequence, and exhibit relatively small repeat frequencies (Lapitan, 1992).

The dispersal pattern of interspersed repetitive elements in higher eukaryotic genomes has led to the suggestion that they are, or once were, transposable elements known as transposons (Flavell, 1986; Lapitan, 1992). Transposons are genetic elements that can move from one chromosomal location to another, without necessarily altering the general architecture of the chromosomes involved. The existence of transposons has only found general acceptance within the last few decades. Genes were originally believed to have fixed chromosomal locations that only change as a result of chromosomal rearrangements resulting from illegitimate crossing-over between incompletely homologous short sections of DNA. Then, in the late 1940's, McClintock's pioneering experiments with maize showed that certain genetic elements regularly "jump", or transpose, to new locations in the genome (McClintock, 1984).

Transposable elements (TEs) reside in the genomes of virtually all organisms (Berg and Howe, 1989). TEs encode enzymes that bring about the insertion of an identical copy of themselves into a new DNA site. Transposition events involve both recombination and replication processes that frequently generate two daughter copies of the original transposable element; one remains at the parental site, while the other appears at the target site (Shapiro, 1983).

Two major classes of eukaryotic TEs have been identified, which are distinguished by their mode of transposition (Finnegan, 1989). Class I elements transpose via the creation of an RNA intermediate that is then re reverse-transcribed to create a DNA copy that integrates at the target site. This class includes several families of retroelements—retrotransposons and retroviruses—including the copia elements of *Drosophila melanogaster*, the gypsy/Ty3 family, the Ty1 element of yeast, and the mammalian immunodeficiency and Rous sarcoma (RSV) retroviruses. Each of these retroelement families are characterized in part by the presence of long terminal repeats (LTRs) at their borders (Finnegan, 1989); however, this class also includes non-LTR-containing elements like Cin4 from maize (Schwarz-Sommer and Saedler, 1988) and the mammalian L1 family (Hutchinson et al. 1989).

The copia elements in *D. melanogaster* possess long terminal direct repeats. There are more than 11 families of copia-like elements; the members of each are well-conserved and are located at 5 to 100 different sites in the Drosophila genome. These elements are about 5000 base pairs (bp) long, with long terminal repeats (LTRs) several hundred bp in length that vary in both sequence and length between families. At the termini of each element are short imperfect inverted repeats of about 10 bp.

Insertion of copia into a new chromosomal site is accompanied by replication of a 3–6 bp stretch of target DNA; the length, but not the sequence, of the direct repeats that consequently appear immediately before and after the element is the same for all members of the same family. Copia elements have one long open reading frame (ORF) that encodes proteins homologous to those of RNA tumor viruses: homologies to reverse transcriptase, integrase, and nucleic acid-binding proteins suggest that these proteins function to create an RNA intermediate for copia transposition.

Class II elements, like the *Drosophila melanogaster* P element (Engels, 1989; Rio, 1990) and the maize Ac/Ds element (Federoff, 1989), transpose directly to new sites without the formation of an RNA intermediate. P elements reside at multiple sites in the Drosophila genome and are 0.5 to 1.4 kb in length, bounded by perfect inverted repeats of 31 bp. They represent internally deleted versions of a larger element of about 3 kb called a P factor, which occurs in one or a few copies only in so-called "P strains" of Drosophila. Upon insertion into a new site in the genome, P elements create 8 bp duplications of the target sequence.

The Ac/Ds system in maize consists of Ds elements, which, like the P elements of Drosophila, are derived from a larger complete element called Ac. Ds elements exist in several different lengths, from 0.4 to 4 kb. Unlike P elements, Ds elements remain stationary within the chromosome unless an Ac element is also present. Ds elements contain perfect inverted repeats of 11 bp at their termini, flanked by 6–8 bp direct repeats of the target DNA. When a Ds (or Ac) element transposes, it leaves behind imperfect but recognizable duplications of the 6–8 bp target sequence.

As stated above, it appears likely that many interspersed repetitive DNA families are, or once were, transposons. In soybean, an interspersed repetitive DNA family whose structural characteristics clearly define it as a transposon family is the Tgm family. The Tgm family is related to the maize En/Spm transposons and consists of fewer than 50 members ranging in size from under 2 kb to greater than 12 kb (Rhodes and Vodkin, 1988).

Retroviruses are type I transposons consisting of an RNA genome that replicates through a DNA intermediate. Although the viral genome is RNA, the intermediate in replication is a double-stranded DNA copy of the viral genome called the provirus (Watson et al., 1987). The provirus resembles a cellular gene and must integrate into host chromosomes in order to serve as a template for transcription of new viral genomes (Varmus, 1982). New genomes are processed in the nucleus by unmodified cellular machinery.

The viral genome RNA looks like a cellular messenger RNA (mRNA), but does not serve as such following infection of a cell. Instead, an enzyme called reverse transcriptase (which is not present in the cell, but is instead carried by the virion) makes a DNA copy of the viral RNA genome, which then undergoes integration into cellular chromosomal DNA as a provirus. Integration of the viral DNA is precise with respect to the viral genome, but is semi-random with respect to the host cell genome, in that some sites are utilized more frequently than others (Shih et al., 1988). The integrated provirus serves as a template for production of new viral RNA genomes, which move to the cell membrane to assemble into virions. These bud from the cell membrane without killing the cell.

Retrovirus virions have icosahedral nucleocapsids surrounded by a proteinaceous envelope. The retroviral genome is diploid, and its general organization is well-known in the art. Typical retroviruses have three protein-encoding genes: gag (group-specific antigen) encodes a precursor polypeptide that is cleaved to yield the capsid proteins; pol is cleaved to yield reverse transcriptase and an enzyme involved in proviral integration; and env encodes the precursor to the envelope glycoprotein. A fourth type of retroviral gene, called tat, has been found at the 3' end of the HTLV-I and -II genomes, which serves as a transcriptional enhancer. A few retroviruses have additional genes, such as onc, that give them the ability to rapidly induce certain types of cancer.

Retroviral genomes contain LTR sequences at both their 5' and 3' ends (Weiss, 1984). These sequences include signals needed for replication, transcription, and post-transcriptional processing of viral RNA transcripts. The LTRs are perfect direct repeats created by the addition of sequences (called $U_5$ and $U_3$, derived from the opposite ends of the viral genome) to each end of the viral genome during the creation of the double-stranded DNA intermediate. The $U_5$ region appears to be essential for initiation of reverse transcription and in packaging of viral transcripts (Murphy and Goff, 1988). The $U_3$ region contains a number of cis-acting signals for viral replication, and sequences responsible for much or all of the transcriptional control over viral genes.

Retroviral genomes also contain a primer binding site (PBS) near the 5' end (Dahlberg et al., 1974). This sequence is complementary to the 3' end of a cellular tRNA. The tRNA is stolen from the host cell during replication and serves as a primer for reverse transcription of the RNA genome soon after infection.

Once the provirus is integrated into cellular chromosomal DNA, it is stable and replicates along with the host cell DNA. Proviruses are never excised from the site of integration, although they may be lost as a result of deletions. Retrovirus infections usually do not harm the cell, and infected cells continue to divide, with the integrated provirus serving as a template to direct viral RNA synthesis.

Like all viruses, retroviruses have a specific requirement for interaction with a target cell-surface receptor molecule for infection. In all cases known (and suspected), this molecule is a protein that interacts specifically with a specific virion env protein. The best-studied of virion envelope protein-cell surface receptor interaction is that of HIV with the CD4 receptor on human T-cells (Dalgleish et al., 1984). The env protein appears to bind to a small region on the receptor not involved in cell-cell recognition or any other known function. Another retrovirus whose cellular receptor has been identified is Moloney murine leukemia virus (MMLV), which interacts with a cell surface protein that resembles a membrane pore or channel protein. Although the mechanism of interaction of many retroviruses is not yet well understood, it does appear that retroviruses interact with a wide variety of receptor types (Weiss, 1982).

Retroviruses have been studied intensely over the past several decades, mainly because of their ability to cause tumors in animals and to transform cells in culture. The ability of retroviruses to transform cells is based on at least two mechanisms. The first is that certain viruses have incorporated activated proto-oncogenes that upon mutation have acquired the ability to transform cellular growth. The second mechanism of transformation results from insertional mutagenesis upon integration of the viral genome. Because the viral LTRs have promoter and enhancer activities, insertion of an LTR sequence in either orientation adjacent to a cellular gene may lead to inappropriate expression of that gene. If the cellular gene is involved in regulation of cell growth, over- or under-expression or insertional mutagenesis of that gene may lead to uncontrolled growth of the cell.

Retroviral integration is thus potentially mutagenic. Integration of retrotransposons within exonic coding regions may inactivate those genes, while integration within introns or flanking regions may create novel regulatory patterns with significant developmental and evolutionary implications (McDonald, 1990; Robins and Samuelson, 1993; Schwarz-Sommer and Saedler, 1987; Weil and Wessler, 1990; White et al., 1994). Enhancers and trans(e activating sequences have been found in retroviral and retrotransposon LTRs (Boeke, 1989; Cavarec, et al, 1994; Choi and Faller, 1994; Lohning and Ciriacy, 1994; Mellentin-Michelotti et al., 1994; Varmus and Brown, 1989), and retrotransposon insertions between coding regions and enhancers disrupt gene expression (Cal and Levine, 1995; Georgiev and Corces, 1995; Geyer and Corces, 1992; White et al., 1994).

Element mobilization not only modifies target gene activity, it restructures genomic architecture (King, 1992, Lim and Simmons, 1994; McDonald, 1993; Shapiro, 1992). In fact, one of the major genomic differences between related taxonomic groups appears to be the identity and distribution of repetitive elements, not single-copy coding sequences (McDonald, 1993; Shapiro, 1992). White et al. (1994) have demonstrated that the flanking regions of many maize genes are embedded in sequences containing traces of retrotransposon DNA. Moreover, Palmgren (1994) has found that the BstI retroelement from maize encodes two conserved domains found in plant membrane $H^+$-ATPases, suggesting that element acquisition of host sequences is not confined to vertebrate retroviruses.

McClintock (1984) has proposed that genetic variation, induced in part by transposable element-mediated insertional mutagenesis, is a directed response to conditions that create "genomic stress." Many TEs and retroviruses preferentially insert in transcriptionally active regions of the genome (Engels, 1989; Sandmeyer et al., 1990; Varmus and Brown, 1989). The Ty1 retrotransposon in yeast can be activated by growth in suboptimal temperatures (Paquin and Williamson, 1988) and by exposure to radiation (McEntee and Bradshaw, 1988). Similar observations have been made in Drosophila (McDonald et al., 1988; Strand and McDonald, 1985), maize (McClintock, 1984), and soybean (Sheridan and Palmer, 1977).

In plants, TEs are activated during the induction of tissue culture (Hirochika, 1993; Peschke and Phillips, 1991) and may contribute to somaclonal variation observed for a number of higher plant species including soybean (Amberger et al., 1992; Freytag et al., 1989; Graybosch et al., 1987; Roth et al., 1989). In maize, the activation of transposable elements is correlated with changes in the pattern of DNA methylation that occur during induction of cultures (Brettell and Dennis, 1991; Kaeppler and Phillips, 1993; Peschke et al., 1991), providing a well-characterized basis for gene activation.

In plants, most transposon-like sequences appear to be extinct (Grandbastien, 1992). Although a number of plant species harbor these sequences (Flavell et al., 1992; Grandbastien, 1992; Voytas et al., 1992), active transposition has only been demonstrated or directly implicated in tobacco (Grandbastien, et al., 1989; Pouteau et al., 1994) and maize (Johns et al., 1985). RNA transcripts and cDNAs from transposons have been recovered from tobacco (Pouteau, et al., 1994; Hirochika, 1993) and maize (Hu et al., 1995), and transposable element-related proteins have been detected in maize (Hu et al., 1995).

The stable introduction of foreign genes into plants represents one of the most significant developments in a continuum of advances in agricultural technology that includes modern plant breeding, hybrid seed production, farm mechanization, and the use of agrichemicals to provide nutrients and control pests. Genetic engineering has been applied to many species in efforts to improve production efficiency and environmental conservation. Genetic engineering complements plant breeding efforts by increasing the diversity of genes and germplasm available for incorporation into crops and shortening the time required for the production of new varieties and hybrids, while also providing opportunities to develop new agricultural products and manufacturing processes.

The first transgenic plants were tobacco plants transformed with a chimeric neomycin phosphotransferase gene carried on the Ti plasmid of *Agrobacterium tumefaciens* (Horsch et al., 1984). Agrobacterium-mediated Ti plasmid transfer has proved to be an efficient, versatile method of plant transformation. The range of plant species amenable to genetic engineering using Agrobacterium is fairly large. In those systems where Agrobacterium-mediated transformation is efficient, it is the method of choice because of the facile and defined nature of the gene transfer.

Few monocotyledonous plants appear to be natural hosts for Agrobacterium, however, although transgenic plants have been produced in asparagus and transformed tumors have been observed in yam. Many commercially valuable crop species, such as cereal grains (e.g., rice, maize, and wheat) are not efficiently transformed by Agrobacterium, despite extensive efforts made in this direction. This appears to be due to differences in the wound response; those species recalcitrant to Agrobacterium-mediated transformation probably do not express the required appropriate wound response (Potrykus, 1991).

Physical methods of gene delivery have been developed in order to transform plants not susceptible to Agrobacterium. These methods include biolistic projection ("particle gun"), microinjection, electroporation, and lipofection (Potrykus, 1991). Most physical transformation experiments have utilized plant protoplasts as the recipient cells; however, other regenerable explants have been utilized, including leaves, stems, and roots. Many plant species have been successfully transformed with physical techniques, but some, notably legumes and cereals, have proved difficult to stably transform by these methods. The applicability of such physical methods to these plants is limited by the difficulties involved in regenerating plants from protoplasts, although some success in this regard has been achieved with some cereals and rice. Little success has been achieved with soybean or maize.

Little experimentation has been reported regarding the use of viral vectors for transformation of plants. Plant viruses exist in a variety of forms; they contain either DNA or RNA as their genetic material, have either rod- or polyhedral-shaped capsids, and can be transmitted either by insects, bacteria, or contact with wounded regions (Robertson, et al., 1983). Most known plant viruses contain single (+) strand RNA as their genetic material. (+) strand plant viruses can further be divided into those which possess a single RNA chain and those which have several RNA chains, each necessary for viral infectivity and which are separately encapsulated into separate virions. Cowpea mosaic virus, for example, contains two RNAs, one encoding several proteins including terminal protein and a protease, with the other chain encoding capsid proteins. There also exist segmented double-strand RNA plant viruses. The best-known of these is wound tumor virus (WTV) which contains 12 different segments and which can replicate in either insect or plant cells.

There are fewer plant DNA viruses. Only two known classes exist, one of which contains double strand DNA and which has a polyhedral capsid. The best understood of this class is cauliflower mosaic virus (CMV). The second class of DNA plant viruses are the geminiviruses that consist of paired capsids held together like twins with each capsid containing a circular single-stranded DNA of about 2500 nucleotides. In some cases, the two paired genomes are identical, while in other cases, the two bear almost no sequence relationship.

Early work with a DNA virus showed that a small bacterial antibiotic resistance gene integrated into such a virus could spread systemically throughout infected plants and confer resistance (Brisson, et al., 1984). It has been suggested that the small size of DNA viral genomes is prohibitory to the wide application of such vectors as useful transforming agents in plants. However, little has been done to follow up on this work.

Even less work has been performed in plants regarding the application of genetic engineering to the far larger group of plant RNA viruses (Ahlquist et al., 1987; Ahlquist and Pacha, 1990). It has been suggested that because the viral RNA does not integrate into the host genome, and is excluded from the meristems and offspring, the usefulness of such RNA viruses in plant transformation is limited at best (Potrykus, 1991).

SUMMARY OF THE INVENTION

In one aspect, the present invention provides retroviral and retroviral-like polynucleotides derived from a plant wherein such polynucleotides are capable of integration into the genome of a plant cell. The invention is also directed to other plant retroviral or retroviral-like polynucleotides obtainable by hybridization under stringent conditions (see, e.g., Sambrook et al.) with the retroviral or retroviral-like polynucleotides expressly disclosed herein. Also within the scope of this aspect of the invention are regulatory sequences comprising, for example, plant retroviral long terminal repeat (LTR) sequences that may be operably linked to a gene so as to modulate expression of the linked gene.

In a second aspect, the invention is directed to plant retroviral or retroviral-type elements capable of targeted integration into a specific region in the plant genome and further to methods for accomplishing such integration.

In a third aspect, the present invention is directed to vectors containing all or part of a regulatory sequence derived from a plant retrovirus or retrovirus-like polynucleotide, and to vectors comprising all or part of the retroviral or retroviral-like genome and a heterologous gene.

In a fourth aspect, the invention is directed to vectors containing one or more plant retroviral or retroviral-like regulatory sequences operably linked to a heterologous gene. A heterologous gene in the context of the present application refers to a gene or gene fusion or a part of a gene derived from a source other than the plant pro-retrovirus, or a cDNA, or a plant retroviral gene under the regulatory control of a promoter other than its natural promoter.

In a fifth aspect, the invention is directed to isolated purified proteins encoded by the polynucleotides disclosed herein, and to analogs, homologs, and fragments of such proteins that retain at least one biological property of the proteins.

In a sixth aspect, the invention is directed to isolated purified proteins produced by expression of a heterologous gene using the vectors of the present invention.

In a seventh aspect, the invention is directed to methods for using vectors comprising all or part of a plant proretroviral or retroviral genome and vectors comprising plant retroviral regulatory sequences operably linked to a heterologous gene to introduce a heterologous gene or a regulatory element into a plant genome, wherein the expression product of the gene comprises a polypeptide or an antisense RNA and wherein the regulatory element is a transcriptional regulatory element.

In an eighth aspect, the invention is directed to a plant retrovirus comprising a plant retroviral or retroviral-like polynucleotide, a capsid, and an envelope.

In a ninth aspect, the invention is directed to methods for producing a plant retrovirus, in which the plant retroviral polynucleotide is packaged in a capsid and envelope, preferably through the use of a packaging cell line, but alternatively by use of other vector systems or by in vitro constitution of the retroviral capsid and envelope.

In a tenth aspect, the invention is directed to plant cells that have been transformed by transduction of a plant retroviral polynucleotide or transformed by a plant retrovirus comprising a heterologous gene according to the methods of the present invention.

BRIEF DESCRIPTION OF THE DRAWINGS

FIG. 1 shows the DNA sequence of the oligonucleotide used as a primer in the polymerase chain reaction that generated the plant pro-retrovirus SIRE-1 cDNA Gm776 (SEQ ID NO:1). The 5' and 3' ends of the oligonucleotide are indicated, and degenerate sites (wherein the oligonucleotide mix contained equal proportions of two nucleotides at a given site) are re indicated in parentheses.

FIG. 2 presents the nucleotide sequence of the SIRE-1 cDNA Gm776 (SEQ ID NO:2). The regions corresponding to the oligonucleotide primer used to amplify the cDNA are underlined.

FIG. 4 shows a statistical analysis of sequence similarities between Gm776 and retrotransposons from *A. thaliana* and *Saccharomyces cerevisiae*.

FIGS. 5A and 5B set forth the DNA sequences of oligonucleotides (SEQ ID NOS: 12–24) utilized in sequencing Gm776 and the 2.4 kb SIRE-1 cDNA.

FIG. 6 (Parts A–C) sets out the nucleotide sequence (SEQ ID NO: 3) of the 2.4 kb SIRE-1 cDNA isolated from a lambda gt11 soybean cDNA library.

FIG. 9 shows a comparison of the predicted SIRE-1 $CX_2CX_4HX_4C$ (SEQ ID NO: 60) nucleic acid-binding site sequences (SEQ ID NO: 4 and SEQ ID NO: 61) with the amino acid sequences of those in other nucleocapsid proteins (SEQ ID NOS: 62–68).

FIG. 10 shows a comparison of the predicted amino acid sequence (SEQ ID NO: 5) of the putative SIRE-1 protease domain with the amino acid sequences of other retroelement proteases ( SEQ ID NOS: 69–75).

FIG. 11 shows an alignment of the RNA sequence (SEQ ID NO: 6) of the putative SIRE-1 primer binding site to the 3'-end of soybean $tRNA^{met-1}$ (SEQ ID NO: 76). Identity between the sequences is indicated by a vertical line (|).

FIG. 12 shows a sequence alignment between the 3'-termini of the putative 5' LTR of SIRE-1 (SEQ ID NO: 7) and the 5' LTR of the potato retrotransposon Tst1 (SEQ ID NO: 77). Identity between the sequences is indicated by a vertical line (|).

FIG. 13 (Parts A–E) sets out the DNA sequence (SEQ ID NO: 8) of the 4.2 kb fragment of the SIRE-1 genomic clone isolated from a lambda bacteriophage FIX II soybean genomic library.

FIG. 15 (Parts A–B) shows the predicted amino acid sequence encoded by the SIRE-1 open reading frames ORF1 (single underline) (SEQ ID NO: 9) and ORF2 (SEQ ID NO: 59) (double underline) encoded by the 4.2 kb SIRE-1 genomic fragment. The sequences formed by stop codons are also shown (SEQ ID NO: 85 and SEQ ID NO:86).

FIG. 16 shows the predicted amino acid sequence (SEQ ID NO: 84) encoded by the SIRE-1 open reading frame ORF2. The putative signal peptide sequence (residues 22–43) and hydrophobic anchor sequence (residues 511–531) are underlined.

FIG. 17 shows a comparison of the predicted amino acid sequence (SEQ ID NO: 11) of the SIRE-1 ORF1 with the C-terminal region of the copia RNase H polypeptide (SEQ ID NO: 78). Vertical lines (|) indicate identity between the sequences, whereas conservative and semi-conservative substitutions are indicated by (:) or (.) respectively.

FIG. 19 shows the DNA sequences (SEQ ID NOS: 25–38) of oligonucleotide primers used to sequence the 4.2 kb genomic fragment. The numbering in the second column indicates the position of the primer sequence with reference to the predicted sense strand of the genomic pG fragment. Also shown are M13/pUC forward (SEQ ID NO: 12) and reverse oligonucleotide sequences (SEQ ID NO: 14).

FIG. 20 shows the results of a computer analysis performed on the predicted ORF2 amino acid sequence (SEQ ID NO: 55) using the computer program NNpredict (Kneller et al. 1990).

FIG. 21 shows a nucleotide sequence comparison among the SIRE-1 3' LTR (LTR2) (SEQ ID NO: 58) and the gag R1 (SEQ ID NO: 57) and R2 (SEQ ID NO: 56) regions. The numbers following the sequence designations indicate the respective locations of the regions within the SIRE-1 4.2 kb genomic fragment.

FIG. 22 (Parts A–C) depicts a nucleotide sequence comparison between Gm776 (SEQ ID NO: 2) and the 2.4 kb SIRE-1 cDNA (SEQ ID NO: 3). The Gm776 DNA sequence is in reverse orientation (i.e., in the 3' to 5' orientation) to the 2.4 kb cDNA sequence.

FIG. 23 shows the predicted amino acid sequence (SEQ ID NO: 83) of ORF2. The putative hydrophobic transmembrane regions are indicated by a single underline. The predicted coiled-coil regions are indicated by a double underline. The proline rich region is indicated by a dotted underscore. The predicted α-helical regions are indicated in boldface type. The potential SU/TM cleavage sites are indicated by boxes.

FIG. 25 shows a schematic representation of the results of restriction endonuclease digestion and Southern hybridization analyses of the SIRE-1 genomic clone. The length and nature of each fragment is indicated by the alphanumerical designation at the left (e.g., 1.5H is a 1.5 kb Hind III fragment). The fragment(s) recognized by each probe (i.e., env, gag, LTR) are indicated by the arrows.

FIG. 30 presents the sequences (SEQ ID NOS: 39–49) of oligonucleotide primers utilized in the sequencing of the 4.1 kb and 4.3 kb SIRE-1 Hind III fragments contained in pEG4.1 and pEG4.3, respectively. The lower-case c following a primer designation indicates that the primer was utilized for sequencing the (−) strand of the insert. Also shown are PUC forward (SEQ ID NO: 12) and reverse (SEQ ID NO: 14) oligonucleotide sequences.

FIGS. 31(a)–(c) presents the nucleotide sequence (SEQ ID NO: 50) of the SIRE-1 genomic clone derived from the sequences of the 4.1 and 4.3 kb SIRE-1 Hind III fragments. The first 321 nucleotides of the sequence are derived from the 3I terminus of the 4.3 kb Hind III fragment, and the remaining sequence is derived from the 4.1 kb Hind III fragment. The Hind III restriction endonuclease recognition site is indicated in boldface (nt 322–327).

FIG. 32 presents the amino acid sequence (SEQ ID NO: 51) of the predicted open reading frame encoded by the combined nucleotide sequences of the 4.3 kb and 4.1 kb Hind III fragments of the SIRE-1 genomic clone.

FIG. 33 presents a comparison of the predicted amino acid sequence (SEQ ID NO: 52) of the SIRE-1 int domain with the integrase domain of the Opie-2 retroelement (SEQ ID NO: 79) from maize. The amino acid residues constituting the HHCC and D(10)D(35)E conserved motifs are presented in boldface. A (.) represents a gap in the sequence required for optimal alignment. A (|) represents identity between the residues. A (:) represents similarity between the residues.

FIG. 34 presents a comparison of the predicted amino acid sequence (SEQ ID NO: 53) of the SIRE-1 reverse transcriptase (RT) domain and the reverse transcriptase domain of the Opie-2 retroelement from maize (SEQ ID NO: 80). The regions corresponding to conserved retroelement RT domains are presented in boldface. A (|) represents identity between the residues. A (:) represents similarity between the residues.

FIG. 35 presents a comparison of the predicted amino acid sequence (SEQ ID NO: 54) of the SIRE-1 Ribonuclease H (RH) domain and the Ribonuclease H domain of the Opie-2 retroelement from maize (SEQ ID NO: 81). The conserved DEDD motif is indicated by boldface. A (|) indicates identity between the residues. A (:) indicates similarity between the residues. A (.) indicates a gap in the sequence required for optimal alignment.

DETAILED DESCRIPTION OF THE INVENTION

Figure 3:
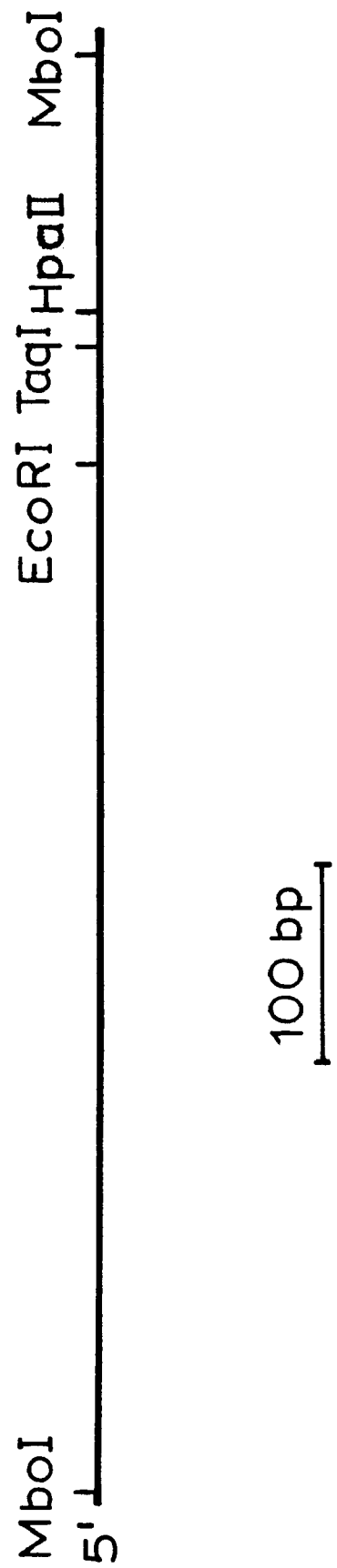
FIG. 3 depicts a restriction map of the SIRE-1 Gm776 cDNA sequence.
Figure 7:
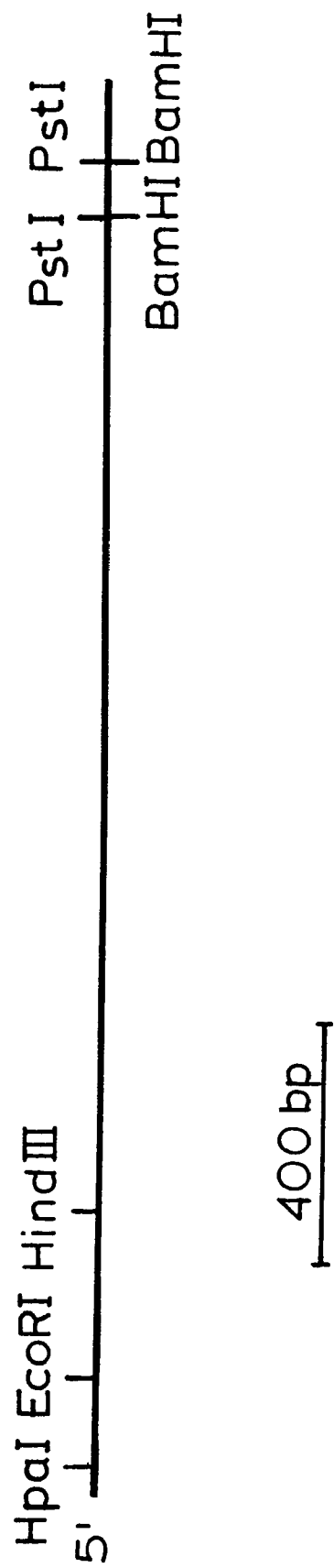
FIG. 7 depicts a restriction map of the 2.4 kb SIRE-1 cDNA.

The present invention provides novel plant retroviruses, proretroviruses, proretroviral polynucleotides, proretroviral DNAs, proretroviral-like polynucleotides and plant retroviral derivatives that are useful for genetic engineering in plants. More particularly, the plant retroviruses, proretroviruses, proretroviral polynucleotides, proretroviral DNAS, proretroviral-like polynucleotides, and plant retroviral derivatives derived therefrom are useful for: introducing a heterologous DNA of interest into plant cells where the peptide or polynucleotide encoded by that sequence will be expressed; for introducing a DNA sequence of interest into plant cells where the RNA encoded by that sequence is complementary (antisense) to an endogenous plant polynucleotide; for introducing a DNA sequence into a plant cell where that sequence becomes integrated into a plant genome; for integrating gene regulatory elements such as transcriptional regulatory sequences into a plant genome; and for identifying the location of such integrations.

The invention provides vector constructs comprising plant proretroviral polynucleotides, proretroviral DNAs, proretroviral-like polynucleotides, fragments thereof, and retroviral derivatives derived therefrom that are useful for: expressing desired proteins in target plant cells, for example, proteins that confer enhanced growth, disease resistance, or herbicide tolerance to plant cells, or to express "antisense" RNA complementary to an endogenous plant polynucleotide.

The invention also provides methods for: producing a plant retroviral vector; using a plant retroviral polynucleotide to identify genetic loci and to characterize the function of a gene within a plant genome; introducing mutations into a plant genome or disrupting an endogenous plant gene ("knockout"); and inserting genes or gene regulatory elements into genomic loci of plants.

The following examples are illustrative of certain embodiments of the present invention but are not to be construed as limiting thereof.

Example 1 describes the isolation and characterization of the SIRE-1 cDNA.

Example 2 describes the isolation and characterization of a full-length SIRE-1 clone from a soybean genomic library.

Example 3 describes the analysis of transcriptional activity from the SIRE-1 pro-retrovirus in soybean and other plants.

Example 4 describes the detection of SIRE-1 retrovirally encoded protein expression in plant tissues by Western blot analysis.

Example 5 describes the in vitro production of polypeptides from SIRE-1-encoded mRNAs.

Example 6 describes the use of SIRE-1 in non-replicative transduction of plant cells.

Example 7 describes methods and products for production of plant retrovirus packaging cells.

Example 8 describes methods for transduction of plant retroviral polynucleotides into plant cells.

Example 9 describes the use of SIRE-1 as a gene transfer vector.

Example 10 describes the use of SIRE-1 to induce and tag mutations in plant genomes.

Example 11 describes the modification of SIRE-1 to effect directed integration at a specific locus in a plant genome.

Example 12 describes the use of SIRE-1 and flanking DNA sequences to determine the site of SIRE-1 insertion in the soybean genome.

EXAMPLE 1

Isolation and Characterization of SIRE-1 cDNA

The initial characterization of the SIRE-1 retroviral DNA was based on the fortuitous recovery and analysis of a 776-bp DNA fragment (Gm776) generated by the polymerase chain reaction (PCR) in an attempt to amplify soybean DNA coding for a cytokinin biosynthetic enzyme (Laten and Morris, 1993). Amplification of either total DNA (from etiolated plumules of Glycine max cv Williams, isolated by the method of Doyle and Doyle, 1990) or nuclear DNA (from G. max cv Wayne, isolated by the method of Hagen and Guilfoyle, 1985) with the single 22-nt oligonucleotide primer (FIG. 1; SEQ ID NO: 1) generated high levels of Gm776. The amount of Gm776 generated in each PCR amplification suggested that SIRE-1 is a member of a multicopy DNA family, and the absence of additional bands suggested that the family is relatively conserved.

Hybridization and restriction digest analyses were performed to characterize the element size of the SIRE-1 family. Soybean genomic DNA was cleaved with BaRHI, EcoRI, HaeIII, HindIII, HpaI, and MboI, respectively, electrophoresed through 0.7–6 agarose, and blotted to a nylon membrane. The blot was hybridized with radiolabeled Gm776 cDNA in 0.05 M Tris, 1 M NaCl pH 7.5 in 50% formamide at 42° C., washed, and exposed to autoradiography (Southern, 1975). These analyses indicated that the SIRE-1 family is composed of several hundred, non-tandem, highly homogeneous copies, each in excess of 10.6 kb in length.

XbaI linkers were ligated to agarose gel electrophoresis (AGE)-purified Gm776 (modified Gm776) (Sambrook et al., 1989; Titus, 1991). The modified Gm776 DNA was extracted with phenol/chloroform and chloroform, ethanol-precipitated, and redissolved in 10 mM Tris-HCl, 1 mM EDTA, pH 7.6. pUC19 was linearized with XbaI and dephosphorylated (Sambrook et al., 1989). Linearized pUC19 DNA and the modified Gm776 DNA insert with the ligated XbaI linkers were ligated, and DH5-α cells were transformed with the ligation products. Transformants were identified by resistance to the antibiotic ampicillin (amp$^r$), and the presence of plasmids containing the insert in the amp$^r$lac$^-$ colonies was determined by hybridization with $^{32}$P-labeled probe synthesized from PCR-amplified, PAGE-purified Gm776 DNA. Plasmid DNA from colonies giving positive hybridization signals was isolated by alkaline lysis (Sambrook et al., 1989).

The recovered pGm776 plasmid DNA was sequenced by dideoxynucleotide chain termination using Sequenase 2.0 (U.S. Biochemical, Cleveland, Ohio) and plasmid-specific and insert-specific primers according to the manufacturer's instructions (FIG. 2, SEQ ID NO: 2; FIGS. 5A and B, SEQ ID NOS: 12–24). Sequence analysis suggested that SIRE-1 is a member of the copia/Ty1 retrotransposon family. SIRE-1 sequences were subsequently detected by hybridization studies using the Gm776 cDNA probe in the genome of G. max cv Williams, in several different cultivars, and in the ancestral species, Glycine soja. The copy number of the element among these sources varies from a few hundred to over a thousand. The variation in copy number, especially among domestic cultivars, suggested that the family remains active, e.g., capable of replication and transposition. The homogeneity of the sizes of the SIRE-1 family members also suggested that most are relatively young and have not had time to accumulate a large number of mutations.

The nucleotide and all six possible peptide translations of the Gm776 sequence were compared to sequences in the GenBank and EMBL databases (Devereux et al. 1984). No closely related sequences were revealed in these searches. However, statistical analyses of sequence similarities between Gm776 and retrotransposons from A. thaliana and Saccharomyces cerevisiae were performed using the Gap computer program (Devereux et al. 1984), and revealed lengthy, albeit weak, sequence similarities. The results of the analyses are set forth in FIG. 4. Column (a) in FIG. 4 denotes the nucleotide ranges within Gm776 that exhibit sequence similarities to other retrotransposon elements, and column (b) denotes the retrotransposon elements that exhibit nucleotide sequence homology to the sequences in column (a). Column (c) shows the percentage identity between the sequence ranges in columns (a) and (b), with gap weights of 3.0 for Ta1 and 2.0 for Ty1 and a gap length weight of 0.3. Two overlapping 300-plus bp regions between nt 150 and 670 of Gm776 exhibit over 50% identity to adjacent regions overlapping the Ta1 RNA binding domain. The alignments include seven gaps in each sequence, averaging 2.5 bp per gap.

When the six potential Gm776 translation sequences were compared to the sequence of the Ta1 polyprotein in the region of DNA similarity, no similarities were observed. However, 51% of the nucleotides between bp 390 and 630 of Gm776 are identical to a sequence within the reverse transcriptase gene of the Saccharomyces cerevisiae retrotransposon Tt1. The alignment requires five gaps averaging 2 bp per gap. There is no significant similarity between any of the six potential Gm776 translation sequences and the corresponding region of the *S. cerevisiae* reverse transcriptase. Sequence comparisons with several other plant transposons, including the copia-like elements Tnt1 from tobacco (Grandbastien et al. 1989), Tst1 from potato (Camirand et al. 1990), and PDR1 from pea did not reveal significant similarities.

Column (d) in FIG. 4 denotes the "qualities" of sequence matches denoted in column (c), and column (e) denotes the qualities and standard deviations of randomized sequence alignments of the same lengths and base compositions. Column (h) represents the probabilities (P) for normal distribution calculated using the equation $P=0.3989e^{-(x2/2)}$ where x=(Q-meanQ)/S.D. The results indicate that the derived similarities are quite significant, especially as approximately 150,000 nucleotides in 30 transposons were analyzed.

A soybean cDNA lambda gt11 bacteriophage library (Clontech) was screened for the presence of SIRE-1 cDNAs by hybridization methods well-known in the art (Sambrook et al. 1989). The radiolabeled probe was generated from the pGm776 plasmid using the Multiprime DNA Labeling kit (Amersham, Arlington Heights, Ill.). Three phage plaques (out of 6,000 screened) showed positive hybridization signals and were isolated by limiting dilution and rescreening. Recombinant phage DNA from one of the clones was isolated from plate lysates (Sambrook et al., 1989) and purified on a Qiagen-100 column as recommended by the manufacturer (Qiagen, Chatsworth, Calif.). The clone contained a 4.0 kilobasepair (kb) insert that was transferred from the phage vector to pUC18 as follows. The purified phage DNA was digested with EcoRI, extracted with phenol/chloroform and chloroform, ethanol precipitated, and redissolved in 10 mM Tris-HCl, 1 mM EDTA, pH 7.6. pUC18 was linearized with EcoRI and dephosphorylated (Sambrook et al., 1989). Linearized pUC18 DNA and the 4.0 kb EcoRI DNA insert were ligated, and DH5-α cells were transformed with the ligation product. Transformants were identified by resistance to the antibiotic ampicillin (amp$^r$), and the presence of plasmids containing the insert in the amp$^r$lac$^-$ colonies was determined by hybridization with $^{32}$P-labeled probe synthesized from PCR-amplified, gel-purified Gm776 DNA.

Plasmid DNA from colonies giving positive hybridization signals was purified over a Qiagen-100 column as described above. Initially, digestion of plasmid DNAs with EcoRI generated insert fragments of 2.4 and 1.6 kb. Only the former hybridized to the Gm776 probe. However, the recombinant plasmid isolated for sequencing contained only the 2.4 kb SIRE-1 fragment, and re-isolation of the original construct proved difficult. The 2.4 kb cDNA insert was sequenced by dideoxynucleotide chain termination using Sequenase 2.0 (U.S. Biochemical, Cleveland, Ohio) and plasmid-specific and insert-specific primers according to the manufacturer's instructions, and was found to be 2389 bp in length (FIG. 6; SEQ ID NO: 3; GenBank Accession No. U22103).

Figure 8:
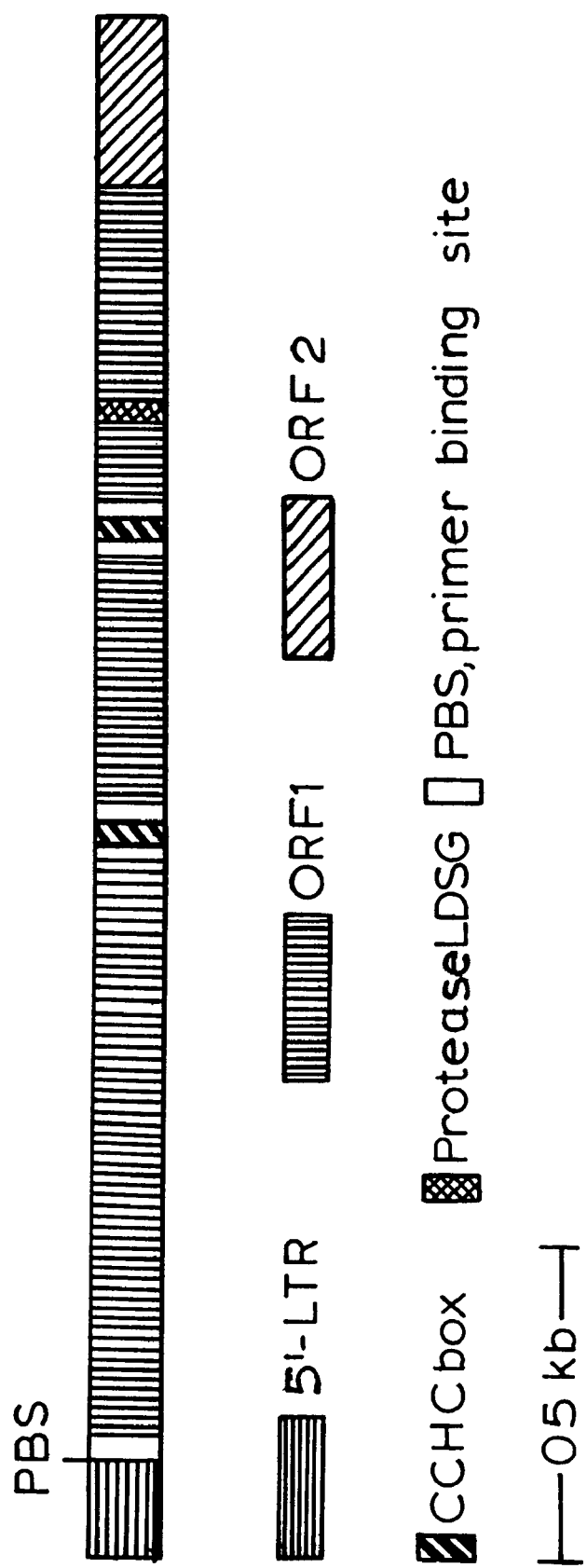
FIG. 8 depicts the organization of the 2.4 kb SIRE-1 cDNA.

The cDNA was found to contain an uninterrupted 617-codon open reading frame (ORF) beginning at nucleotide (nt) 236 (FIGS. 6 and 8; SEQ ID NOS: 8,9). A second 87-codon ORF begins at nt 2155 and continues through the end of the truncated fragment (FIGS. 6 and 8). The ATG codon at nt 236 is the fourth ATG in the sequence. Extended leader regions with ATGs upstream of the actual translational start site are not unknown among retroelement mRNAs (Varmus and Brown, 1989). In the SIRE-1 cDNA (SEQ ID NO: 8), the first ATG at nt 28 is followed immediately by a stop codon, and initiations at the two other upstream ATGs each may produce only a dipeptide. It has been suggested that 40S ribosomal subunits can reinitiate and resume scanning beyond very short, upstream ORFs (Kozak, 1991). The ATG at nt 236 is closely followed by another in-frame ATG at nt 242. The latter is actually in a more representative context for translational initiation than is the former (Heidecker et al., 1986).

The ORF1 of SIRE-1 (FIGS. 6, 8, and 9; SEQ ID NO: 9) contains three regions that are characteristically highly conserved among retroviral and retrotransposon polyproteins (Katz and Jentoft, 1989; Varmus and Brown, 1989). The first two are CX$_2$CX$_4$HX$_4$C (SEQ ID NO: 60). (where C represents cysteine, H represents histidine, and X denotes any amino acid) nucleic acid-binding motifs (i.e., CCHC boxes) found in retroviral and retrotransposon nucleocapsid (NC) proteins encoded by gag, and the third is a catalytic domain (LDSG: lysine-aspartic acid-serine-glycine) characteristic of prot-encoded aspartic proteases that cleave retroelement polyproteins.

In a few characterized retroelements, the CCHC boxes in the gag region are repeated. The repetition of the CCHC boxes in SIRE-1 is unique in that the boxes are separated by 189 codons, rather than by just a few codons as in other retroelements (FIG. 8). As NC proteins are generally less than 100 amino acids in length, it is possible that the SIRE-1 boxes are expressed in two distinct proteins.

Both SIRE-1 CCHC boxes are flanked by highly basic regions, especially the region between the boxes: seven of nine amino acids that precede the downstream box are lysine or arginine. This is characteristic of retroelement NC proteins, which are highly basic and are dominated by polar amino acids. Although the boundaries of the SIRE-1 NC proteins are not yet defined, CCHC boxes are generally found near the carboxy-terminus. The putative NC protein encompasses roughly amino acids 260 to 525. This region is highly basic (23%) and very polar (62%). Sequence comparisons between the SIRE-1 protease peptide sequence and those of other retroelements firmly places SIRE-1 in the copia/Ty1 family (FIGS. 9 and 10).

Retroelement (–) strand replication is usually primed by a host tRNA, often the initiator tRNA. A 22-nt primer binding site (PBS) complementary to the 3' end of soybean tRNA$^{met-1}$ (SEQ ID NO: 76) lies upstream of the SIRE-1 ORFs, between nucleotides 180 and 201 (SEQ ID NO: 6). See FIG. 11. Retroelement PBSs are generally located adjacent to the 5'-LTR (Boeke, 1989). Two bases separate the 5' end of the SIRE-1 PBS from the dinucleotide CA, found at the 3' end of nearly every LTR. The sequence of the downstream LTR from a genomic clone (see Example 2) confirms that this dinucleotide marks the end of the LTR. The a putative SIRE-1 LTR (SEQ ID NO: 7) shows significant homology to the terminal 17 nt of the 5' LTR of the potato retrotransposon Tst1 (SEQ ID NO: 77). See FIG. 12.

An unusual feature of SIRE-1 is the presence of a 95-bp, nearly tandem, direct repeat between nt 2096 and 2299 (FIG. 6; SEQ ID NO: 3). The repeats are separated by 3 bp. The upstream member has an 11-bp insertion that is absent in the downstream member. Otherwise, the sequences are 95% identical. The 5% divergence makes it very unlikely that the duplication was created during the cloning process.

Figure 22A:
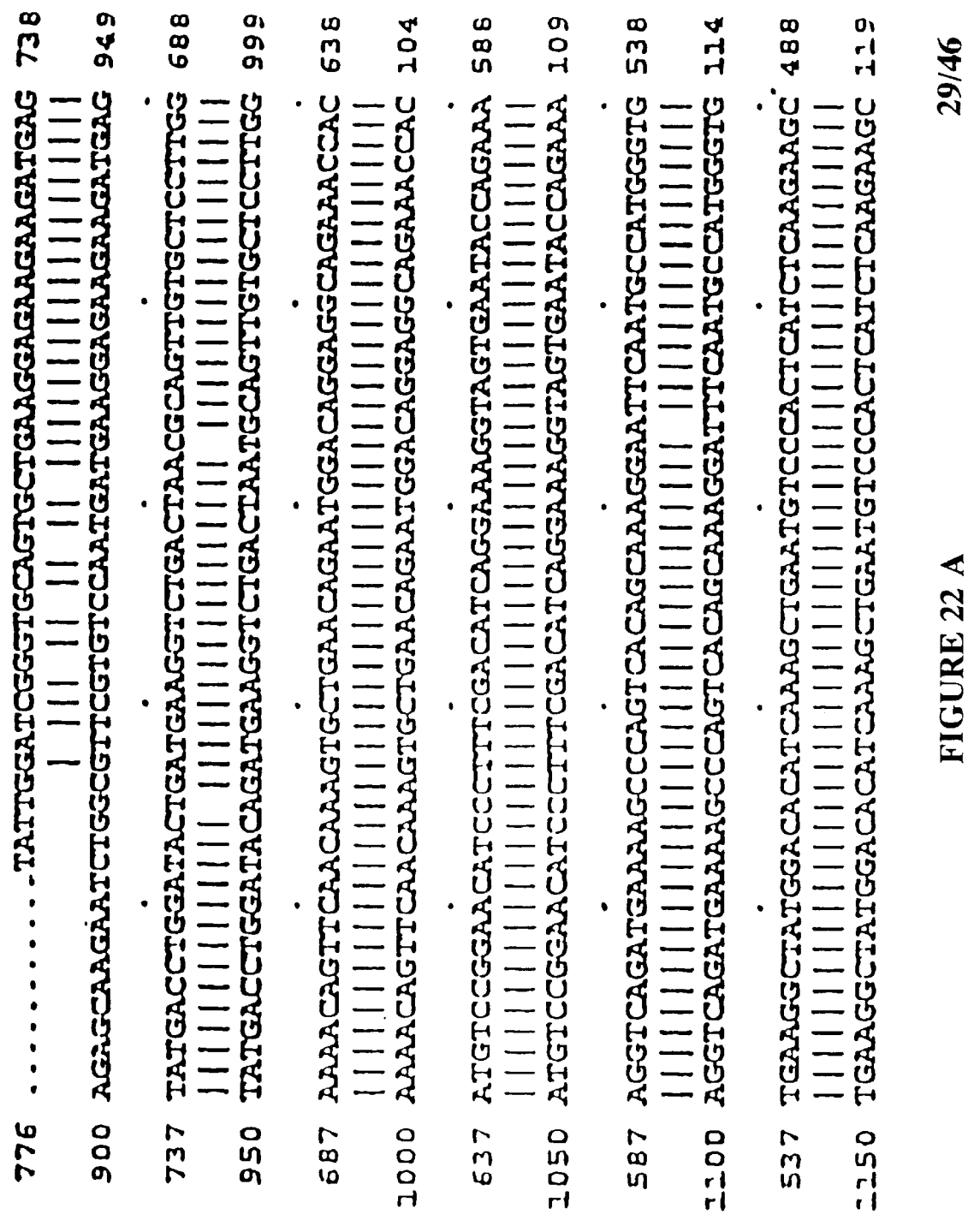

The 2.4 kb cDNA sequence was aligned to the corresponding region of Gm776, and it was found that the amplified fragment lies completely within the gag region of the 2.4 kb fragment, and that the two sequences differ by only 2% (FIG. 22). Of the 13 bp differences, seven retain the same amino acid. Of the remaining six, three result in the substitution of one non-polar amino acid for another—isoleucine for phenylalanine, isoleucine for valine, and leucine for methionine—and two are substitutions of threonine by isoleucine. The last substitution generates a stop codon in Gm776. Among the amino acid changes, only the threonine to isoleucine substitution is not considered to be a conservative replacement. The predominance of silent and conserved substitutions strongly suggests that the differences reflect the slightly diverged, evolutionary relationship between two SIRE-1 family members.

EXAMPLE 2

Isolation and Characterization of the SIRE-1 Genomic Clone

Oligonucleotide primers (FIG. 5B; SEQ ID NOS: 15–24) were utilized in PCR to amplify fragments from the gag and pol regions and from part of the adjacent LTR of the 2.4 kb cDNA clone. These amplified fragments and synthetic oligonucleotides (FIG. 5) were used to generate gag- and LTR-specific radiolabeled probes. A λFIXII soybean genomic library (Stratagene, La Jolla Calif.) was probed with radiolabeled SIRE-1 gag probes and positively-hybridizing plaques were purified by limiting dilution screening (Sambrook et al., 1989). DNA was prepared from phage recovered from liquid culture (Burmeister and Lehrach, 1996).

The phage DNAs containing the putative SIRE-1 genomic clones were digested with the restriction endonuclease Not I to release the DNA inserts from the phage. The largest DNA inserts obtained thereby were digested with Xba I, and Southern blots of the digested DNAs were probed with an end-labeled, LTR-specific oligonucleotide to identify clones carrying two LTRs. Analyses of one clone yielded two hybridizing bands, indicating that this clone contained two LTRs and was a probable source of a full-sized, intact copy of SIRE-1. The purified phage DNA containing the full-length SIRE-1 genomic clone was deposited with the American Type Culture Collection, 12301 Parklawn Drive, Rockville Md. 20852 on Aug. 12, 1997 (ATCC accession number 209200) in accordance with the Budapest Treaty requirements.

Restriction endonuclease digestion of the phage DNA with Xba I yielded three fragments of 8.5, 6.5 and 4.2 kb. Southern hybridization of the electrophoretically separated fragments with a radioactively labeled 2.4 kb SIRE-1 cDNA probe revealed that the SIRE-1 2.4 kb cDNA sequence extends across the 12.5 kb and 4.2 kb Xba I fragments.

The fragments were each subcloned into a PSPORT-1 plasmid (Life Technologies, Gaithersburg Md.) for automated DNA sequencing. Some of these subclones were unstable, but the one carrying the 4.2 kb Xba I fragment that hybridized to the LTR probe, but not to the gag probe, displayed no evidence of rearrangement. Both strands of this 4.2 kb clone were sequenced on ABI Prism 377 DNA sequencers using pUC universal primers and the oligonucleotide primers listed in FIG. 19 (SEQ ID NOS: 25–38). This sequence (FIG. 13; SEQ ID NO: 8) is made available as GenBank Accession number U96295.

Figure 14:
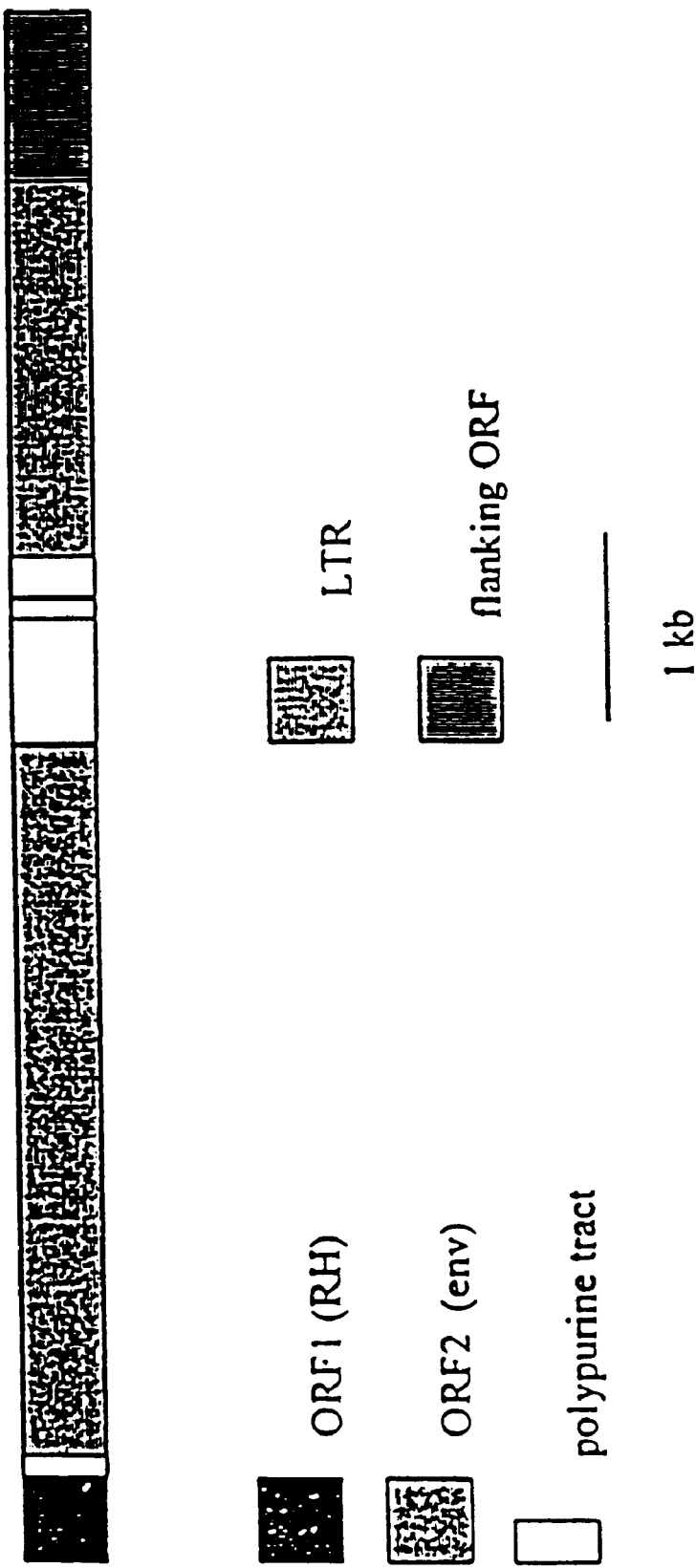
FIG. 14 depicts the organization of the 4.2 kb SIRE-1 genomic fragment.
Figure 18:
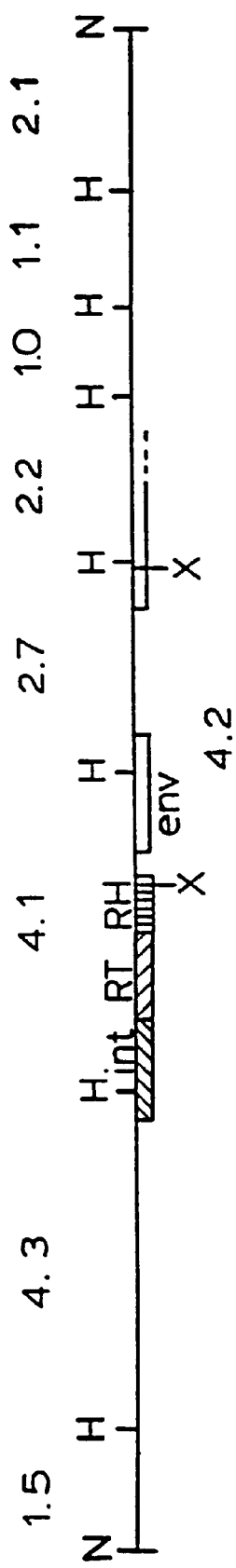
FIG. 18 shows a restriction map of the SIRE-1 genomic clone isolated from a λ bacteriophage FIX II soybean genomic library. The 5' and 3' ends of the insert are at the left and right, respectively. The numbers above and below the schematic indicate the approximate lengths of the restriction fragments. The restriction endonuclease recognition sites are indicated by single letter codes: H represents a Hind III site; X represents an Xba I site; and N represents a Not I site. The boxed regions of the schematic represent open reading frames encoding SIRE-1 proteins: int represents the integrase domain; RT represents the reverse transcriptase domain; RH represents the Ribonuclease H domain; and env represents the envelope protein domain. The rightmost (open) box represents the 3' soybean flanking region.

The 4.2 kb XbaI fragment encompasses the 3' end of the genomic clone and contains the distal 3.7 kb of SIRE-1 along with 538 bp of presumably single-copy flanking DNA (FIG. 14). Analysis and predicted translation of the SIRE-1 genomic sequence revealed the presence of two ORFs (FIG. 14). The first, ORF1 (SEQ ID NO: 9 and 11; See FIG. 15A) extends from nucleotide (nt) 1 to nt 191, and is clearly the 3' end of a retroelement ribonuclease H (RH)-encoding sequence. The 3' terminus of the SIRE-1 RH coding region exhibits significant amino acid sequence homology (i.e., 53% identity and 87% similarity) with the carboxy-terminus of RNase H from copia (FIG. 17). In all copia/Ty1-like retrotransposons, the RH coding sequence is at the 3' end of the pol gene and is closely followed by a polypurine tract (PPT) and the 3' LTR. However, the RH coding region of pol in SIRE-1 is followed by a long ORF in the region corresponding to retroviral env (see below).

Figure 15A:
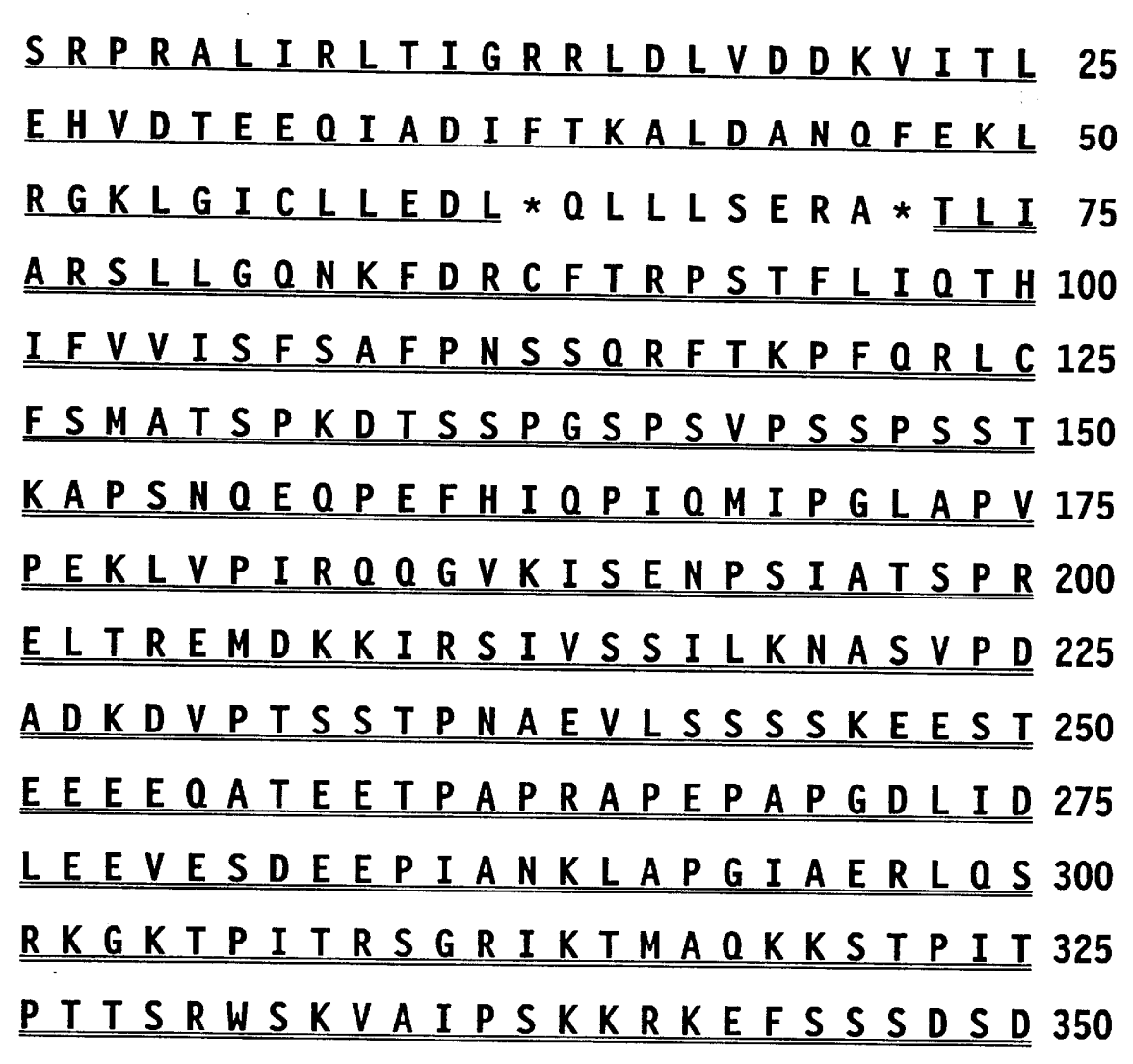

The second ORF within this fragment, i.e., ORF2, extends from nt 219 to nt 1958 The predicted translation product suggests that ORF2 encodes a full-length, envelope (env)-like glycoprotein characteristic of animal retroviruses (FIG. 15A and 15B; SEQ ID NOs: 10 and 59 and FIG. 16; SEQ ID NO: 84). Retroviral envelope proteins are synthesized from a spliced transcript in which the initiation codon is supplied by the gag region, which for SIRE-1 was found in the 2.4 kb cDNA clone (Example 1; SEQ ID NO: 3). The amino-terminal one-third of the SIRE-1 env sequence is rich in proline, serine, and threonine codons, with the latter two possibly serving as O-glycosylation sites. There are also a small number of asparagines in this region that might serve as N-glycosylation sites.

Although the predicted amino acid sequence of ORF2 does not exhibit significant amino acid homology with the known env proteins, its predicted secondary structure is typical of animal retrovirus env proteins. Failure to find high amino acid homology with other retroviral proteins is not surprising, as it is likely that SIRE-1 and gol the animal retroviruses diverged before either had acquired an env encoding region.

A typical retroviral env protein has a signal peptide near the amino-terminus. There is a likely hydrophobic signal peptide at codons 22–43 of the SIRE-1 env sequence (FIG. 16; SEQ ID NO: 84). Near the carboxy-terminus of retroviral envelope proteins, a hydrophobic domain serves to anchor the molecules in the membrane such that the protein is oriented with the N-terminus outside the cell and the C-terminus within the cytoplasm. Codons 511 to 531 of the SIRE-1 env sequence (SEQ ID NO: 84) constitute a hydrophobic region that may provide this function (FIG. 16). These assignments and the appropriate membrane orientations are strongly supported by analysis with the transmembrane prediction computer program TMpredict (Hofman and Stofel, 1993) (see below).

ORF2 is 647 codons in length, and the derived, unmodified theoretical protein has a molecular weight of 70 kD. Despite its location immediately downstream of pol, the translated env amino acid sequence does not exhibit significant sequence identity to any reported retroviral env protein. This result is not entirely unexpected because known env sequences constitute a very heterogeneous population, and pair-wise comparisons often fail to demonstrate significant sequence congruence (Doolittle, et al., 1989; McClure, 1991). Alternatively, ORF2 could be a transduced cellular sequence. For example, Bst1 from maize, a low copy-number LTR retrotransposon that lacks its own RT (Johns, et al., 1989; Jin and Bennetzen, 1989), encodes domains derived from a maize plasma membrane H-ATPase (Bureau, et al., 1994; Palmgren, 1994).

Retroviral env genes encode polypeptides that are cleaved by host proteases into surface (SU) and transmembrane (TM) peptides, respectively, which are subsequently rejoined through disulfide linkages (Hunter and Swanstrom, 1990). While the primary sequences of these proteins may be diverse, all retroviral env proteins are glycosylated and share three functionally conserved hydrophobic domains: a signal peptide near the amino terminus of SU, a membrane fusion peptide near the amino terminus of TM, and a distal anchor peptide (Hunter and Swanstrom, 1990).

Retroviral env glycoproteins contain between four and thirty N-glycosylated asparagines at Asn-Xaa-Ser/Thr motifs (Hunter and Swanstrom, 1990), with SU generally more heavily glycosylated than TM. The conceptual translation product of ORF2 from SIRE-1 has only two Asn in this context. However, retroelement env proteins are also known to be O-glycosylated at Ser and Thr residues (Pinter and Honnen, 1988). O-glycosylation is correlated with clusters of hydroxy amino acids with elevated frequencies of Pro (Wilson et al., 1991). The amino half of the theoretical SIRE-1 protein (corresponding to SU) conforms to this pattern, and many of the hydroxy amino acids in the carboxyl half of the protein are adjacent to Pro. The amino acid composition of one extended proline-rich region encompassing amino acids 60 through 127 (SEQ ID NO: 83) is similar to the 60-amino acid proline-rich neutralization (PRN) domain of SU from feline leukemia virus (FeLV) (Fontenot et al., 1994). Pro makes up 18% in both and hydroxy amino acids are 20% in the FeLV PRN and 22% in SIRE-1. Gln is 9% in FeLV and 10% in SIRE-1, and while the PRN of FeLV contains no aromatic amino acids, the comparable SIRE-1 region contains only one. In SIRE-1, the spacing of many of the Pro residues in this region and beyond $(Xaa-Pro-Yaa)_n$ or $(Xaa-Pro)_n$ is characteristic of many structural membrane proteins from both eukaryotes and prokaryotes (Williamson, 1994).

The putative env protein sequence was evaluated for the presence of hydrophobic, membrane-spanning helices using TMpredict (Hofmann and Stoffel, 1993). The program returned two possible transmembrane regions with high confidence values and a third somewhat below the margin of significance (FIG. 23). The first predicted helix encompasses amino acids 22 to 43 (SEQ ID NO: 83), a typical signal peptide location. The second predicted transmembrane helix extends from amino acid 510 to amino acid 530 (SEQ ID NO: 83), and corresponds to the general location of retroviral anchor peptides. Although of questionable statistical significance, the third predicted transmembrane helix, from amino acids 465 to 485, is in a location that could correspond to that of viral membrane fusion peptides.

Only two retroviral env peptides have been structurally characterized by X-ray crystallography (Chan et al., 1997; Fass et al., 1996), but several env SU and TM sequences have been analyzed by structural prediction computational programs (Hunter and Swanstrom, 1990; Gallaher et al., 1995; Gallaher et al., 1989). Analysis of the ORF2 sequence using the computer program NNpredict (Kneller et al., 1990) suggests the presence of long α-helices and regions of β-sheets (FIG. 20) typically found in env proteins. The evaluation of ORF2 using several other programs (Deleage and Roux, 1987; Georjon and Deleage, 1995; Georjon and Deleage, 1994; Gibrat et al., 1987; Levin et al., 1986), yielded predictions of multiple α-helices similar to those of corresponding regions of other retroviral env proteins (Hunter and Swanstrom, 1990; Gallaher et al., 1995; Gallaher et al., 1989).

ORF2 (SEQ ID NO: 83) was also evaluated for the possible presence of coiled-coils (Lupas et al., 1991). Amino acids 580 to 611 were predicted to form a coiled-coil with very high confidence (FIG. 23). The sequence adheres well to the heptad repeat sequence identified in several virus fusion peptides (Chambers et al., 1990). The predicted coiled-coil in the TM domains of HIV and Moloney murine leukemia virus have recently been confirmed by X-ray crystallography (Chan et al., 1997; Fass et al., 1996).

Retroviral env proteins are generated from spliced transcripts (Varmus and Brown, 1989; Hunter and Swanstrom, 1990). In the case of some avian retroviruses, splicing leads to an in-frame fusion of the gag start codon with the 5' end of the env coding region (Hunter and Swanstrom, 1990), obviating the need for an initiating AUG in env. An analogous splice in a SIRE-1 transcript would serve the same purpose, although no splice donor or acceptor consensus sequences are present in the expected regions. Cleavage of env proteins into SU and TM generally occurs at a conserved site containing the consensus sequence Arg-Xaa-Lys-Arg (Hunter and Swanstrom, 1990). This sequence does not appear in the putative SIRE-1 env, but there are several similarly basic tetrapeptide candidates for such a cleavage site (FIG. 23). The Lys-Lys-Gly-Lys (SEQ ID NO: 82) at residues 439–442 would generate a TM protein of 22.3 kD with the fusion peptide near the amino terminus. The corresponding SU would be 48.7 kD.

To confirm that the putative env gene was not a library or cloning artifact, and that most, if not all, genomic copies of SIRE-1 were organized in the same way as the clone, SIRE-1 genomic DNA was digested with several restriction enzymes and a Southern blot was probed with sequences from the env and gag subclone regions. The intensity of hybridization of an env probe to genomic DNA (data not shown) was similar to that for the gag probe that had previously been used to establish the moderately high copy number of SIRE-1 (Laten and Morris, 1993). In addition, gag and env probes hybridized to the same 10.5 kb HpaI fragment (data not shown). Although the possibility cannot be ruled out, this env-like ORF is probably not a transduced host gene. The presence of this ORF in most if not all of the several hundred copies of SIRE-1 suggests that this gene is an integral part of the retroelement genome.

Alternate splicing could result in an additional ORF extending from nt 1834 to 2166, thereby encoding a 110-amino acid peptide. Such alternate splicing of retroviral transcripts at similar sites has been shown to lead to the production of trans-acting factors, which may be useful in modulating gene expression in accordance with the present invention.

To identify the LTR, the DNA sequence (SEQ ID NO: 8) from the 4.2 kb XbaI fragment was aligned with that from the SIRE-1 cDNA clone (SEQ ID NO: 3) which contained the last 178 bp of the 5' LTR. Sequence alignments were made using the Genetics Computer Group package (Devereux et al., 1984). The GCG analysis confirmed that the genomic subclone contained a 3' LTR and fixed the location of the 3' end of the LTR at nt 3686 in the sequence AATTTCA (FIG. 3; SEQ ID NO: 8), beyond which the two sequences diverged. Although the region of LTR overlap was virtually identical (98% sequence identity), the moderately high copy number of SIRE-1 makes it unlikely that the cDNA and genomic clones represent copies of the same element.

Upstream of the genomic LTR there are several polypurine regions ranging in length from 11 to 16 nucleotides (FIGS. 13 and 14). Such sites are known to serve as origins for initiation of retroelement plus-strand synthesis. In addition, the SIRE-1 LTR contains appropriately located sequences that strongly resemble consensus sequences for retroviral promoter elements and polyadenylation signals.

The 538 nucleotides of flanking DNA adjacent to the 3'-end of the SIRE-1 sequence (SEQ ID NO: 8) comprises an uninterrupted open reading frame (FIG. 14). This strongly suggests that the SIRE-1 insertion disrupted a functional gene. As the *G. max* cultivar is essentially a tetraploid, its genome can accommodate some gene disruptions without major phenotypic consequences. The predicted translation product of the flanking DNA is relatively hydrophilic and is rich in asparagine and glutamine codons. No significant homology was found with known plant proteins, however.

Figure 24:
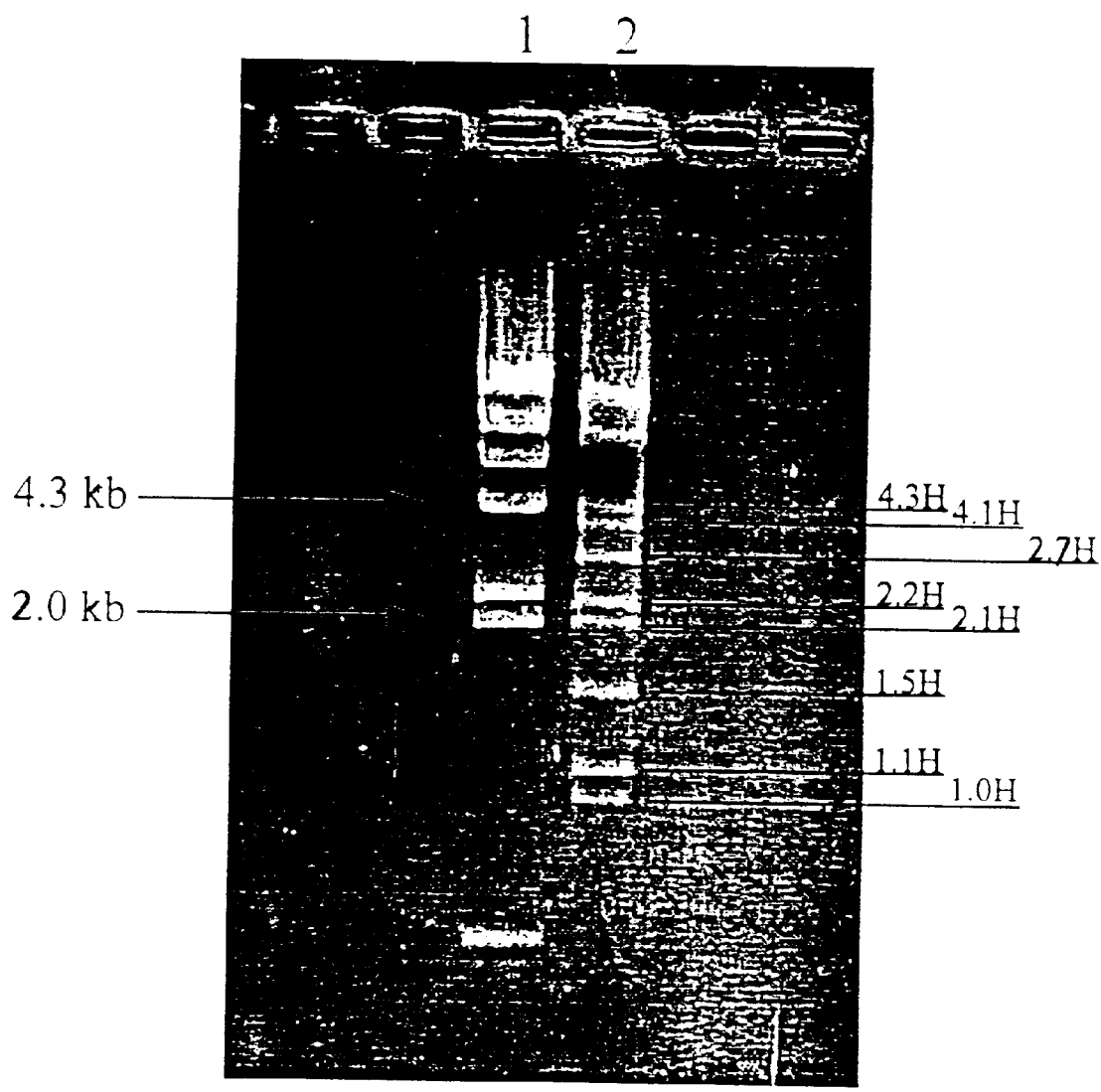
FIG. 24 depicts an agarose gel electrophoretic analysis of restriction endonuclease digestion of the SIRE-1 λFIXII genomic DNA by Hind III. Lane 1 contains λ DNA size markers. Lane 2 contains the SIRE-1 λFIXII genomic DNA digested by Hind III. The relative lengths of the Hind III fragments are indicated by the numbers (e.g., 2.1 H is a 2.1 kb Hind III fragment).

To obtain other subclones of SIRE-1, the genomic SIRE-1 λFIXII bacteriophage DNA was double-digested with Hind III (which does not digest λFIXII DNA) and Sac I (which does digest λFIXII DNA in the multicloning region). This digest generated 10 fragments (FIG. 24). The two largest fragments, 20 kb and 9 kb, respectively, are known to constitute the lambda phage arms. The other eight fragments collectively constituted 19 kb of SIRE-1 genomic sequence. Individual digests of the genomic clone with Hind III and Sac I, respectively, revealed that the 2.1 kb and 1–5 kb fragments produced in the double digest were adjacent to the lambda phage arms (data not shown). Therefore, these two fragments each have Hind III and Sac I termini, while the other 6 fragments have only Hind III termini.

Figure 26:
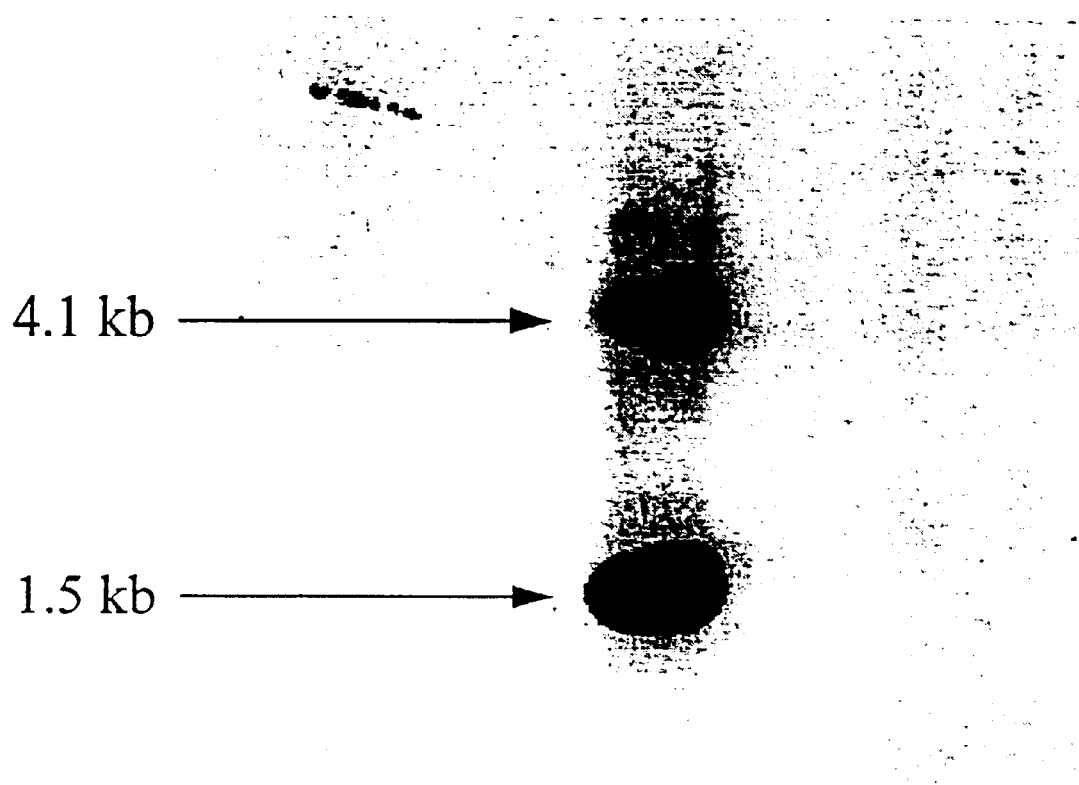
FIG. 26 presents the result of a restriction endonuclease digestion and Southern hybridization analysis of the SIRE-1 genomic clone. The SIRE-1 genomic clone was digested with Sac I and Hind III. The length of the hybridizable fragments is indicated to the left. The Southern hybridization was performed with a radioactively labeled env probe derived from the 4.2 kb Xba I fragment.
Figure 27:
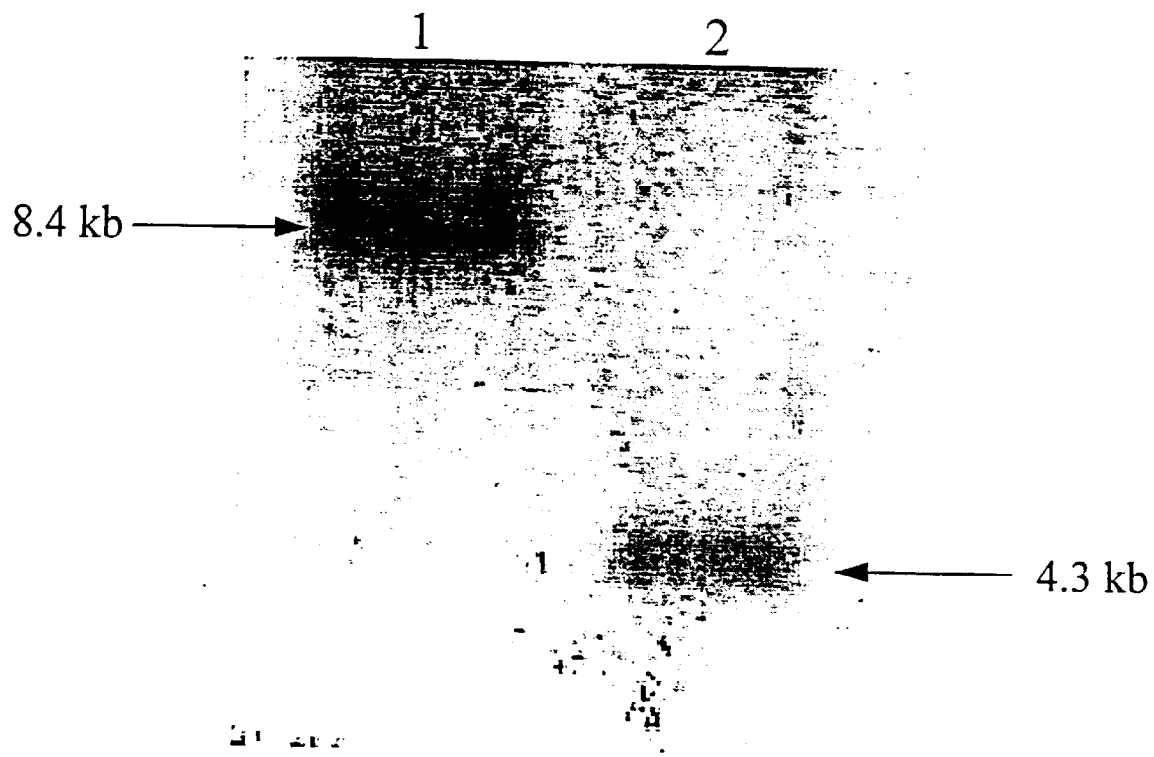
FIG. 27 presents a schematic of the pEG4.1 vector construct. The 4.1 kb SIRE-1 insert is indicated by the thick bolded clockwise arrow.

Southern blot hybridizations were conducted with the Hind III/Sac I double-digested SIRE-1 DNA using probes derived from the LTR, gag, and env regions of the 4.2 kb Xba I fragment, respectively (FIG. 25). These experiments revealed that the env sequence lies within the 4.1 kb fragment (FIG. 26); the LTR regions are contained within the 4.3 kb and 2.7 kb fragments; and the gag region is also contained within the 4.3 kb fragment (FIG. 27).

Figure 28:
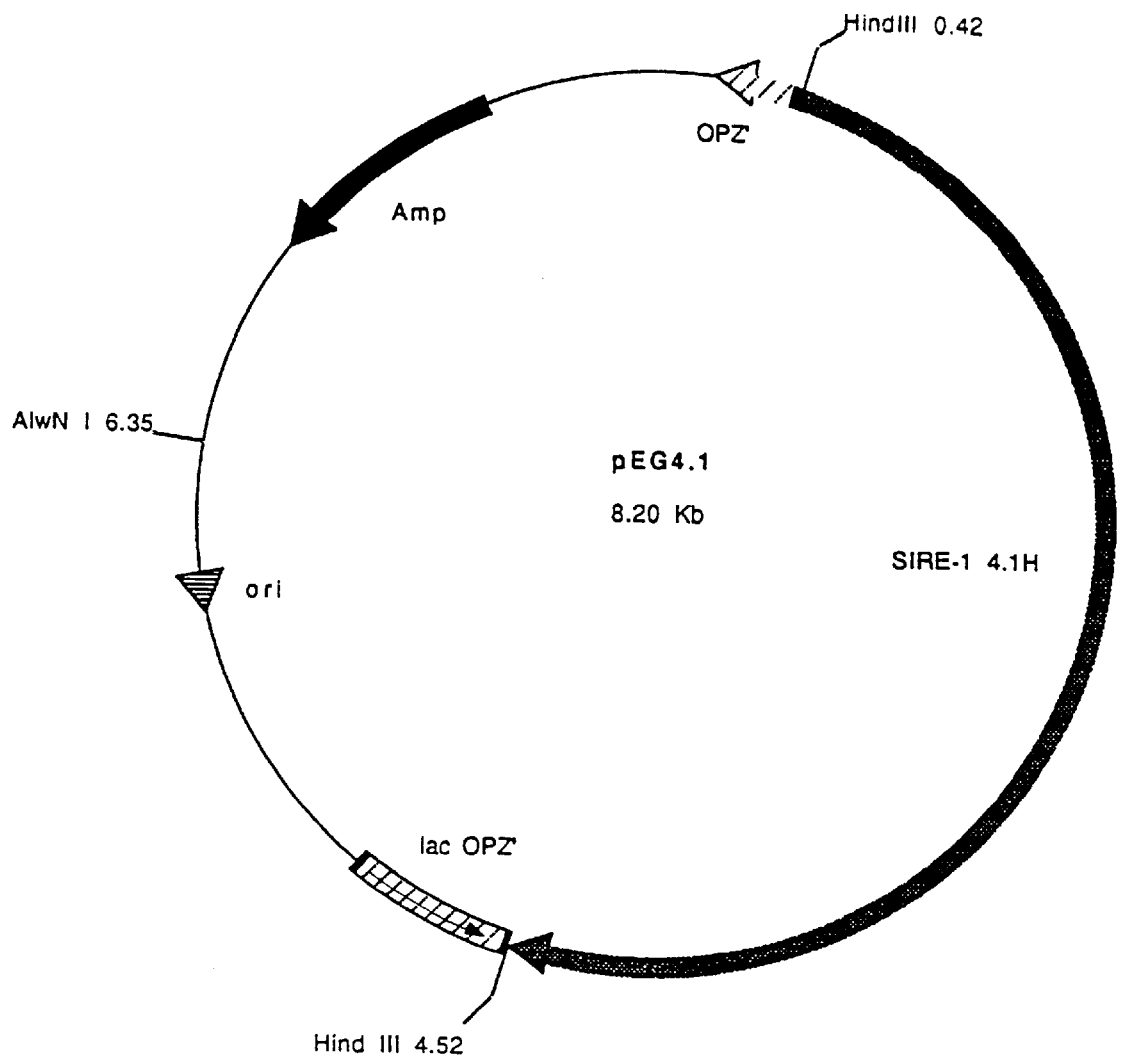
FIG. 28 depicts the result of restriction endonuclease digestion and Southern hybridization analysis of the pEG4.3 vector construct comprising the 4.3 kb SIRE-1 Hind III fragment. The Southern hybridization was performed using a radioactively labeled gag probe derived from the 4.2 kb SIRE-1 Xba I fragment.
Figure 29:
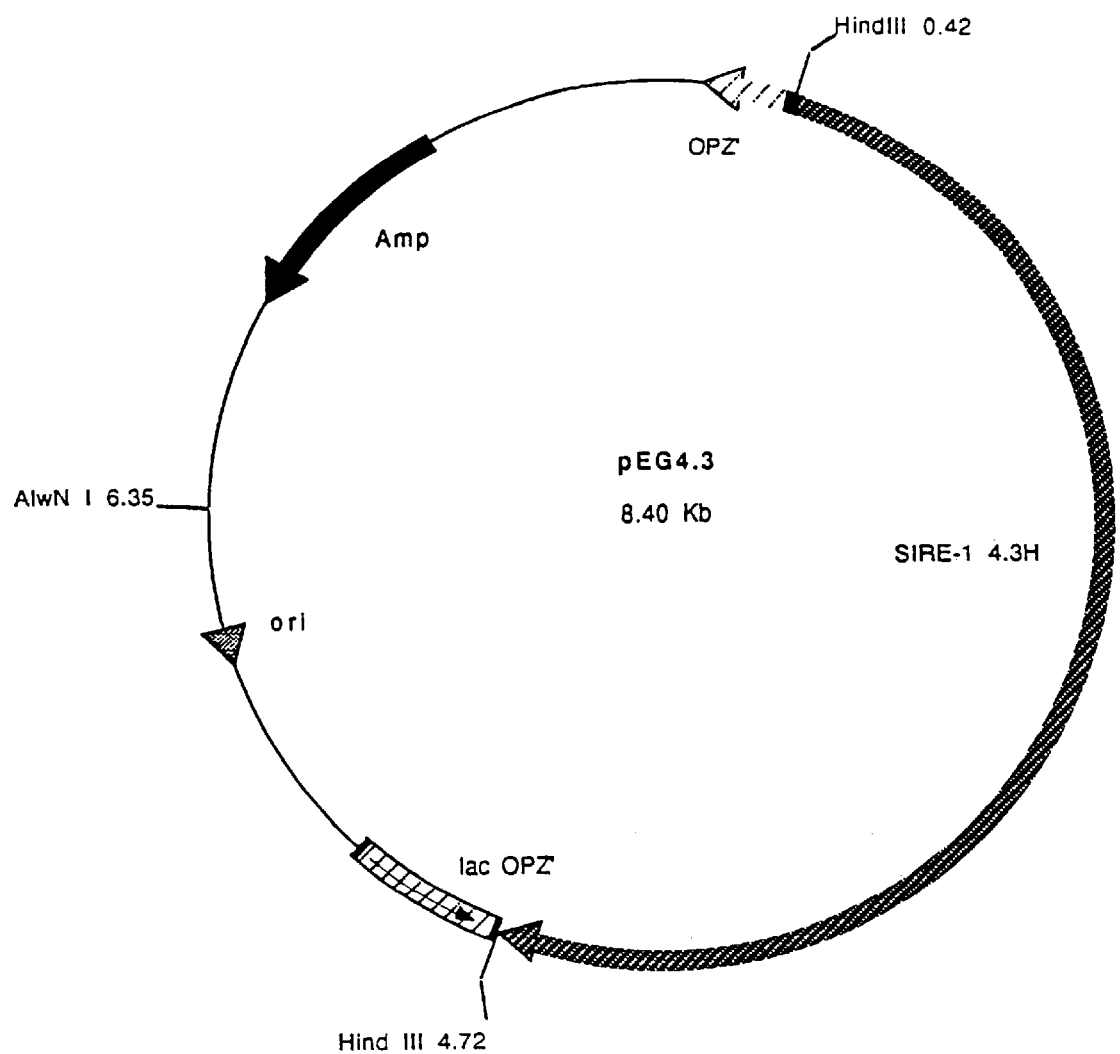
FIG. 29 presents a schematic of the pEG4.3 vector construct. The 4.3 kb SIRE-1 insert is indicated by the thick bolded clockwise arrow.

The 4.1 kb fragment (containing at least a portion of the env region) and the 4.3 kb fragment (containing at least a portion of the gag region) were each subcloned into pSPORT-1 vectors and the constructs were separately transformed into DH10B *E. coli* cells. Recombinant plasmids were detected by restriction digestion and Southern hybridization. The vector construct comprising the 4.1 kb fragment was named pEG4.1 (FIG. 28), and the vector construct comprising the 4.3 kb fragment was named pEG4.3 (FIG. 29).

The pEG4.1 construct was sequenced using M13/pUC universal primers (pUC-forward and -reverse; SEQ ID NOS: 12, 14) and SIRE-1 specific primers (FIG. 30; SEQ ID NOS: 39–49) as described above. Translation of the nucleotide sequence obtained thereby (FIGS. 31a–c; SEQ ID NO: 50) revealed a long uninterrupted open reading frame encoding 942 amino acids (FIG. 32; SEQ ID NO: 51). The 3' terminus of the 4.1 kb Hind III fragment overlapped the 5' terminus of the 4.2 kb Xba I fragment (described above, containing the env region) by approximately 1.5 kb. Translation of the remaining 2.6 kb sequence revealed regions exhibiting strong homologies to the integrase, reverse transcriptase, and RNase H regions of known retrotransposons.

The 4.3 kb Hind III fragment contained in pEG4.3 was partially sequenced using pUC universal primers (REF; SEQ ID NOS: 12,14). The 5' terminal region of the 4.3 kb fragment was found to contain sequence identical to that of the putative 3' LTR contained within the 3' terminal region of the 4.2 kb Xba I (env-containing) fragment (SEQ ID NO: 8). The 3' terminal region of the 4.3 kb Xba I fragment contained sequences exhibiting strong homology to the amino-terminal region of the integrase (int) domain of known retrotransposons.

A region encompassing 400 amino acid residues predicted from the contiguous nucleotide sequences of the 3'-terminal region of the 4.3 kb fragment and the 5'-terminal region of the 4.1 kb fragment, respectively, appears to constitute an integrase (int) domain (SEQ ID NO: 52). The predicted amino acid sequence of this putative int domain was compared against the BLAST-P peptide database. Significant homology was found with copia-like retrotransposons, with the strongest homology being to the Opie-2 element from maize, which exhibited 39.8% identity and 58.5% similarity at the amino acid level, with three sequence gaps (FIG. 33). The putative SIRE-1 and Opie-2 elements each contain a conserved HHCC (H-X4-H, C-X2-C) motif, which is usually found at the amino-terminus of retrotransposon integrase domains (FIG. 33). The SIRE-1 and Opie-2 elements also each contain a D(10)D(35)E motif (i.e., two aspartate residues within 10 residues of each other, and a glutamate residue within 35 residues of the pair in the carboxy-terminal direction) (FIG. 33).

The break point between the integrase (int) and the reverse transcriptase (RT) domains of SIRE-1 was determined by comparison of the 4.1 kb fragment sequence with the sequences of retroelements where the break point has been determined experimentally (Doolittle et al., 1989; McClure, 1991; Springer and Britten, 1993; Taylor et al., 1994; Rogers et al., 1995). The predicted amino acid sequence (SEQ ID NO: 53) of the reverse transcriptase domain extends from residue 401 to residue 781. This predicted sequence was compared against the BLAST-P peptide sequence database. Significant homology was found between the putative SIRE-1 RT region and the RT regions of copia-like retrotransposons (FIG. 34). Again, the most significant match was to Opie-2 from maize, which exhibited 560 identity and 71. similarity at the amino acid level, with one sequence gap (FIG. 34). Several regions in which the SIRE-1 RT exhibits near identity to that of Opie-2 encompass sequences that have proved useful in studying the phylogenetic relationships of retroelements (Xiong and Eickbush, 1990).

The break point between the reverse transcriptase (RT) and Ribonuclease H (RH) regions of the SIRE-1 4.1 kb fragment sequence was also predicted by comparison against those of known retroelements. The RH domain of SIRE-1 appears to encompass the predicted amino acids 782 to 942. This predicted sequence (SEQ ID NO: 54) was compared against the BLAST-P peptide sequence database. Not surprisingly, the strongest homology was found with the RH element of maize Opie-2, which exhibited 53.1% identity and 71.0% similarity to the predicted SIRE-1 RH region (FIG. 35). The SIRE-1 RH domain also contains the DEDD motif found in the RH elements of most known retrotransposons (FIG. 35).

These data confirm that SIRE-1 is a retroviral family whose genomic structure is based on a copia/Ty1-like organization. The genomic organization of all animal retroviruses (from vertebrates and Drosophila) is patterned after gypsy/Ty3-like retrotransposons. Neither retroviral genomes nor virions have been reported in plants, although both classes of retrotransposons are widespread. In plants, virus spread is mediated by intercellular movement (Mushegian and Koonin, 1993). However, very few plant virus genomes encode an env gene. Those that do—rhabdoviruses and bunyaviruses (Matthews, 1991)—also infect animal hosts where env proteins mediate viral-host cell membrane fusion. Plant cell walls may preclude this mode of virus transfer, and whether the env proteins of these viruses serve any function in their plant hosts is not known. Thus, the presence of an env gene in SIRE-1 suggests that SIRE-1 may have originally been an infectious invertebrate retrovirus.

The overall restriction site homogeneity, the presence of long, uninterrupted ORFs within and adjacent to SIRE-1, and the near identity of the 5' and 3' SIRE-1 LTRs suggest that SIRE-1 is not an evolutionary relic, and may be modified to function as an infectious retrovirus and/or intracellular retrotransposon.

The genomic clone may be used as a SIRE-1 genomic probe. The probe may be hybridized to Southern blots of complete and partial digests of soybean DNA to generate a consensus restriction map (Sambrook et al., 1989). Additionally, restriction maps of additional clones and the genomic DNA consensus may be compared to more fully assess SIRE-1 heterogeneity. The polymorphic sequences of clone populations may then be used to determine expression-related features and phylogenetic relationships to other plant and animal elements.

The env, gag, and pol nucleotide sequences may be used to generate oligonucleotide or cDNA probes to detect transcription of these regions (Navot et al., 1989), and antibodies generated against SIRE-1 proteins may be used to detect the presence of retroviral protein expression in various plant tissues (Hsu and Lawson, 1991). Moreover, reverse transcriptase (RT) and integrase (int) probes may be created by restriction digestion or PCR and used to assess the functional significance of the unprecedented length of SIRE-1.

EXAMPLE 3

Northern Hybridization Analysis of SIRE-1 Transcriptional Activity

The use of the SIRE-1 polynucleotide as a tool for genetic engineering may require the expression of sequences therefrom. It may therefore be desirable to determine growing conditions under which plants or plant cell cultures that have been infected or transduced with SIRE-1-derived DNA exhibit elevated or depressed transcriptional activity. There are many examples in which the transcriptional activity of a virus is enhanced during periods in which its host experiences environmental stress. Therefore, experiments may be conducted to determine growth conditions (or conditions of stress) optimal for the regulation of SIRE-1 expression.

The presence of SIRE-1-specific transcripts in plants such as soybean may be evaluated by Northern hybridization (Sambrook et al., 1989). For example several G. max cultivars, including the Asgrow Mutable line, an unstable soybean isolate (Groose & Palmer, 1987; Groose et at, 1983), and Glycine soja strains (from a range of origins) may be grown from seed obtained from the U.S. Regional Soybean Laboratory in Urbana, Ill.

Plants may be grown under optimal and adverse (stress) conditions in growth chambers or in a greenhouse, and the transcriptional activity of SIRE-1 in plants subjected to adverse conditions may then be compared to that in plants grown in normal conditions.

Many potential adverse growing conditions are well-known in the art. For example, seedlings may be grown in vermiculite and subjected to temperatures ranging from 15° C. to 40° C. Plants may also be subjected to salt stress by applying NaCl solutions ranging up to 20%, or to osmotic stress by adding solutions containing PEG 8000. Plants growing under each or several of these conditions may be harvested at various times to assess the temporal relationship of the adverse condition to the transcriptional activity of SIRE-1. To assess the impact of viral infection, leaf tissue may be inoculated with a virus such as soybean mosaic virus and harvested at 2, 5, 10 and 20 days after infection (Mansky et al., 1991).

In addition, the transcriptional activity of SIRE-1 may be assessed in plant tissue cultures. Tissue cultures may be initiated from roots, cotyledons, or leaves from selected cultivars as described (Amberger et al, 1992; Roth et al., 1989; Shoemaker et al., 1991). Tissue can then be transferred to Petri plates containing Gamborg's B5 medium supplemented with kinetin, casein hydrolysate and concentrations of 2,4-D ranging from 1 to 20 $\mu$M. After the formation of callus, suspension cultures may be initiated and maintained in liquid medium (Roth et al., 1989). These cultures may then be exposed to adverse growing conditions as described above.

Total RNA may be isolated from seeds, cotyledons, leaves, roots, shoot tips, or cultured cells using commercial kits such as RNeasy™ (Qiagen, Chatsworth, Calif.). If necessary, polyadenylated RNA may be isolated from total RNA using the PolyATtrac™ mRNA isolation system (Promega, Madison, Wis.). Isolated RNA may then be applied to nylon membranes (Gene Screen Plus™, New England Nuclear, Boston, Mass.) using a slot-blot apparatus, denatured, and probed with end-labeled oligomers or radio-labeled cDNAs corresponding to the gag or pol regions of SIRE-1 (Sambrook et al., 1989). RNA samples that give positive signals may be fractionated on 1% agarose-formaldehyde gels, blotted to nylon membranes, and probed as above. Preliminary studies of SIRE-1 RNA transcripts in G. max (using the slot-blot procedures described above) have revealed the presence of high levels of gag transcripts in leaf tissues.

As retro-elements commonly produce polyprotein-encoding transcripts that traverse nearly the entire element, functional SIRE-1 transcripts could exceed 10 kb in length. This could limit the applicability of agarose-formaldehyde gel separations. Alternatively, isolated RNA can be analyzed for the presence of SIRE-1 transcripts by ribonuclease (RNase) protection assays well-known in the art. For example, RNA isolated from plants grown in the above-described conditions can be hybridized to SIRE-1-derived radiolabeled RNA probe in solution and then exposed to one or more of several available RNases. The double-stranded hybrid formed by the probe and target RNA is protected from RNase digestion. The protected RNA can be fractionated on a denaturing polyacrylamide gel, blotted to a nylon membrane, and visualized by autoradiography.

EXAMPLE 4

Detection of Retroelement Proteins by Western Hybridization Analysis

Plant tissue samples that contain SIRE-1-specific transcripts may be analyzed for the presence of SIRE-1-specific proteins or for proteins expressed by heterologous genes inserted into a SIRE-1 derived vector. Protein recovered from these tissues may be spotted on nylon membranes and assayed for the presence of nucleocapsid, protease, and RT polypeptides by Western hybridization (Sambrook et al., 1989).

Polyclonal antisera against SIRE-1 proteins (or fusion constructs containing SIRE-1 and heterologous peptide sequences) to be detected in these hybridizations can be obtained using methods well-known in the art. For example, oligopeptides may be designed and synthesized using sequence information from the cDNA and genomic clones. The synthetic oligopeptides may be coupled to carrier protein using for example gluteraldehyde, and antibodies against these raised in rabbits and affinity-purified as is well-known in the art (Harlow and Lane, 1988).

Alternatively, polyclonal antisera may be raised against fusion proteins produced by inserting the appropriate SIRE-1 DNA fragments (or DNA encoding the heterologous proteins) in a protein expression vector like pPROEX-1 (Life Technologies, Gaithersburg, Md.) and isolating the fusion protein according to the manufacturer's instructions.

Monoclonal antibody preparations against SIRE-1 proteins or fusion proteins may also be isolated from hybridoma cells derived from splenocytes or thymocytes of mice immunized with such proteins according to methods well-known in the art (Harlow and Lane, 1988).

EXAMPLE 5

In vitro Transcription and Translation of SIRE-1 Transcripts

It may be desirable to produce SIRE-1 polypeptides in vitro for use in producing antibodies or for capsid reconstitution studies and to provide reagents for in vitro packaging of retroviral polynucleotides. Production of SIRE-1 polypeptides in a cell-free environment may be accomplished by creating cDNAs from SIRE-1 mRNA transcripts, inserting those cDNAs into plasmids, propagating the plasmids, and utilizing such plasmids in in vitro transcription/translation reactions as are well-known in the art. cDNAs may be recovered from full-length SIRE-1 transcripts isolated from soybean total or poly-A-selected RNA. Such cDNAs may be produced using reagents and reactions optimized for long transcripts (Nathan et al., 1995). Total or poly-A-selected soybean RNA may be reverse-transcribed with SuperScript II™ reverse transcriptase (Life Technologies, Gaithersburg, Md.) using an oligo(dT) primer. RNase H may be added and the single-stranded cDNA amplified using LA Tag DNA polymerase (Oncor) with oligo(dT) and 5' primers derived from the proximal end of the SIRE-1 gag and/or env cDNA sequences. The 5' end of each PCR primer may contain a restriction enzyme recognition sequence for subsequent vector ligation in the appropriate orientation and sequences that would facilitate enhanced transcription and/or translation.

Amplified cDNAs may be initially characterized by agarose gel electrophoresis and Southern hybridization using gag-, pol- and env-specific cDNA or oligonucleotide probes. The amplified DNAs may be ligated into pSPORT-1 (Life Technologies, Gaithersburg, Md.), a vector designed to carry large inserts, and the recombinant plasmids used to transform competent E. coli DH5α cells (Life Technologies, Gaithersburg, Md.). Plasmid DNA may be recovered from transformants and evaluated by restriction mapping and Southern hybridization as described above. Selected regions of several cDNAs may be sequenced with primers based on the sequence obtained from the genomic SIRE-1 clone. cDNA variability may be assessed and quantitatively compared to that observed with Tnt1 transcripts in tobacco, which constitute a quasispecies-like collection (Casacuberta et al., 1995). The transcriptional initiation site(s) may be evaluated by primer extension and/or S1 nuclease digestion (Sambrook et al., 1989).

Alternatively, a parallel series of experiments may be run to generate translatable mRNAs. SIRE-1-specific cDNAs may be generated as above, except that the 5' PCR primer may be derived from the beginning of the gag and pol coding regions. The cDNA sequence suggests that a single gag-pol ORF may not be present in SIRE-1, and translation of the downstream pol region requires readthrough of a stop codon and/or a frameshift. It is probable that the ribosomes in the in vitro translation system may not emulate the in vivo translation. For expression of the pol region, the cDNAs may be amplified using a 5' primer derived from the proximal end of the pol ORF.

Plasmid DNAs containing SIRE-1 cDNAs may be recovered, and coupled in vitro transcription-translation assays may be run (Switzer and Heneine, 1995) using a reticulocyte lysate system (Promega, Madison, Wis.). Translation products may be analyzed by SDS-PAGE and Western hybridization as described above.

As an alternative to coupled in vitro transcription and translation, SIRE-1 cDNAs may be cloned into the protein expression vector pPROEX-1 (Life Technologies, Gaithersburg, Md.), and fusion proteins, expressed in E. coli and recovered as described by the manufacturer. SIRE-1 cDNAs utilized in the above-mentioned reactions could include those encoding analogs, homologs, or fragments of the full-length SIRE-1 gag, pol, or env proteins. These proteins, although not identical to proteins encoded by the SIRE-1 polynucleotides disclosed herein, may nevertheless be useful if they retain at least one biological property of SIRE-1 proteins. Such proteins may be used for antibody generation as described above, or for subsequent protein conformation studies.

EXAMPLE 6

Modification of SIRE-1 for Use in Non-Replicative Transduction of Plant Cells SIRE-1 may be adopted for use as a retroviral vector in legumes, e.g., soybean, common beans, and alfalfa, cereals, e.g., rice, wheat, and barley, and other agronomically important crops such as fruit trees, conifers, and hardwoods. The use of a plant retrovirus for introduction of DNA sequences into plant cells presents several advantages over previously-known methods. First, unlike other plant viral vectors (Joshi and Joshi, 1991; Potrykus, 1991), the SIRE-1 pro-retrovirus may integrate into the host genome and generate stable transformants (Crystal, 1995; Miller, 1992; Smith, 1995).

Second, although other vectors have been used to introduce nucleic acid into plant genomes, they have serious limitations. For example, Ti plasmid-based vectors lead to integrative transformation, but their bacterial host, *Agrobacterium tumefaciens*, has a limited host range that does not include many legumes or most cereals (Christou, 1995; Potrykus, 1991).

Finally, physical transformation methods (i.e., biolistic projection or microinjection) are far less efficient than viral infection in introducing DNA constructs into desired cells. These physical methods also generally require regeneration of adult plants by somatic embryogenesis (Christou, 1995; Potrykus, 1991).

A full-length SIRE-1 pro-retroviral DNA and vectors derived therefrom will be competent to effect transduction into plant host cells and integration into the host genome, using any of the foregoing methods. However, it may be desirable to modify SIRE-1 vectors so as to limit the region of integration, to restrict subsequent transposition events, to add DNA sequences to promote homologous recombination between a vector and a target region of the genome, and to insure against infectious spread of a potentially pathogenic agent.

SIRE-1 may be modified in a manner analogous to that used for vertebrate retroviruses to create recombinant viral vectors that may infect host cells but not complete an infection cycle. For vertebrate retroviral vectors, this is accomplished by deleting or disabling the trans-acting elements (i.e., gag, pol, and env) from the vector to be transduced into the host cell, while leaving intact the cis-acting elements (i.e., LTRs and packaging signals). This is followed by transduction of the modified vector into retrovirus packaging cell lines or tissue cultures (Miller, 1992; Smith, 1995) that may contribute the necessary trans-acting elements.

Thus, the present invention contemplates SIRE-1 constructs in which sequences encoding the trans-acting factors (e.g., gag, pol, and env), the LTRs, or the packaging signals have been mutated or deleted, either singly or in combination. Mutations may be easily accomplished using PCR-mediated site-directed or cassette mutagenesis techniques as are well-known in the art.

The trans-factor encoding sequences may be deleted by digestion of the SIRE-1 viral DNA with appropriate restriction enzymes. Those of ordinary skill in the art will be readily able to determine the appropriate restriction enzyme recognition sites in the SIRE-1 DNA that will allow for removal of the appropriate trans-factor DNA segments while leaving intact essential cis element sequences. One approach would be to digest the SIRE-1 DNA with a restriction enzyme that would cleave at sites located at or near the 5' and 3' boundaries of the ORF2 region (FIG. 14) such that all or part of the env-encoding region could be-removed from the vector.

Restriction digestion may be followed by recovery and purification of the digested vector DNA fragments containing cis factor sequences, followed by religation of the digested termini (Sambrook et al. 1989). Alternatively, appropriate double-stranded DNA linkers may be ligated to the digested ends of the vector DNA in order to maintain or create a proper reading frame. As another possibility, linker sequences containing one or more endonuclease restriction enzyme recognition sites may be ligated to the ends of the digested vector DNA, and these ends then religated in order to facilitate subsequent insertion of heterologous gene sequences.

Infection of packaging cells or tissue cultures with the modified SIRE-1 vector may allow for the recovery and use of a non-replicative recombinant vector in a functional virion particle that may be capable of intercellular transport (for example, through plasmodesmata), host cell penetration, nuclear targeting, and chromosomal integration, but incapable of further transposition. Reporter genes like GUS (β-glucuronidase, Jefferson et al., 1981) or Npt-II (Neomycin phosphoryltransferase, Pridmore, 1987) and others (Croy, 1994) may also be incorporated into SIRE-1 or vectors derived therefrom to allow detection of integration events.

EXAMPLE 7

Production of Plant Retroviral Packaging Cells

Modification of pro-retroviruses for use as vectors is fairly straightforward. In essence, retroviral vectors are simple, containing the 5' and 3' LTRs, a packaging sequence, and a transcription unit composed of the recombinant gene or genes of interest and appropriate regulatory elements which include LTRs but which may also include heterologous regulatory elements. To grow the vector, however, the missing trans-factors must be provided using a so-called packaging cell line. Such a cell is engineered to contain integrated copies of gag, pot, and env, but to lack a packaging signal so that no "helper virus" sequences become encapsidated. Additional features may be added to or removed from the vector and packaging cell line to render the vectors more efficacious or to reduce the possibility of contamination by "helper virus."

A packaging cell line is produced by means of transfection of a helper virus plasmid encoding gag, pol, and env and by selecting for cells that express the proteins and that can support vector production (Miller, 1990). To avoid replication of helper sequences, one may make deletions in, for example, the packaging signal regions. To avoid recombination between the packaging vector and the replicating vector, the 3' LTR is commonly deleted and replaced with a polyadenylation sequence (Dougherty et al., 1989). Deletions may also be incorporated into the 5' LTR to reduce its ability to replicate, and a heterologous promoter may be inserted downstream to maintain expression of the trans-factors (Miller, 1989). Finally, the viral genome may be split into two transcription units, one encoding gag and pol and a second encoding env (Markowitz, 1988). The cis-acting factors may be deleted or modified from these vectors in order to prevent production of replication-competent retrovirus by the packaging cells.

The trans-acting factors encoded by the helper virus construct may include the native factors from SIRE-1, modified SIRE-1 factors, or other proretrovirus-derived factors that may result in an increased or alternative host range or higher efficiency of viral production or transduction efficiency (Smith, 1995). Thus, the present invention encompasses vectors containing sequences encoding the trans-acting factors from SIRE-1, either singly or in various combination, for use in creating packaging cells, and the packaging cells themselves.

To manipulate target cell specificity, the env gene of the helper virus/packaging cell line may be varied. A successful approach has been to remove sequences from the env gene and replace them with sequences encoding proteins with a different specificity (Russell et al., 1993). For example, erythropoietin sequences have been incorporated into mammalian retroviruses to target the EPO receptor (Kassahara et al., 1994). Another approach has been to incorporate a single-chain antibody into the env sequence (Chu et al., 1994). Finally, the ability of retroviruses to incorporate glycoproteins from other viruses into their envelope has been utilized to produce so-called pseudotypes (Dong et al., 1992). The pseudotype retrovirus acquires the infective range of the glycoprotein donor, and usually is more stable as well. Analogous strategies may be used in SIRE-1 retroviral vectors to manipulate the host range beyond soybean by inserting into the SIRE-1 env gene ligand-, receptor-, or single-chain antibody-encoding fragments that could recognize, or be recognized by, proteins from other plant species, such as rice or maize.

EXAMPLE 8

Transduction of the SIRE-1 Plant Proretrovirus into Plant Cells

If the SIRE-1 proretrovirus or vectors derived therefrom integrate into the genome of a cell transduced with such DNA, all cells derived from the original cell transfected with the SIRE-1 vector may contain the retroviral insertion. Infections are commonly targeted to embryonic, meristematic, or germ line cells to enable transmission to progeny plants. Since certain plants (such as *G. max*) are self-fertilizing, transfection of embryos or meristematic tissue may lead to homozygosity of inserted DNA in some $F_1$ offspring, although the proportion of seed homozygous for a particular insertion event may need to be empirically tested. Dominant changes may be manifested in heterozygous progeny. Transfection of various adult tissues, especially meristems and ovaries, or seeds, pollen, protoplasts, or callus, may be performed by standard inoculation and/or co-incubation techniques which are well known (Potrykus, 1991). Viruses may also be inoculated into phloem for transport to distant sites. In some cases, physical methods such as biolistic projection, microinjection, or macroinjection may be necessary or preferred to transduce SIRE-1 into plant cells or tissues (Draper and Scott, 1991; Potrykus, 1991).

EXAMPLE 9

Use of SIRE-1 as a Gene Transfer Vector

SIRE-1 may be modified to carry useful gene sequences (e.g., gene sequences encoding useful proteins) or, alternatively, genes to produce antisense transcripts against undesirable endogenous sequences or to introduce into the genome gene regulatory elements which may regulate transcription of an adjacent gene. This may be easily accomplished by restriction enzyme digestion of the vector DNA at sites near the 5' and 3' boundaries of the ORFs encoding the gag, pot, and/or env proteins (as described above), isolating the remaining vector DNA, and either ligating a heterologous DNA fragment between the digested vector termini or alternatively by recombinantly inserting a multicloning site (Sambrook, et al., 1989) between the digested vector termini to allow for subsequent facile restriction enzyme digestion and recombination of digested vector and heterologous DNAs. Heterologous gene sequences may be operably linked to (heterologous) host-cell specific promoter sequences (Waugh and Brown 1991), or their transcription may be driven by the SIRE-1 LTR promotor activity. The heterologous gene sequences may encode any of a variety of polypeptides whose expression may result in useful phenotypic changes of the host cell and plant. By way of example, introduction and expression of these heterologous gene sequences in plants may result in the generation of the following exemplary phenotypic variations:

A. Disease Resistance

Many agronomically important crops are susceptible to a variety of diseases, viral infections, and bacterial or fungal infestations. Resistance to these conditions results in higher crop yields and decreased use of bacteriocidal and fungicidal compositions. Transfer of genes conferring resistance to diseases and/or viral or bacterial infection is an object of the present invention.

Many plant genomes, including soybean, are currently being mapped (Keim et al. 1996). In addition, genetic loci associated with disease resistance have been identified in many plant lines. For example, resistance markers and quantitative trait loci (QTL) for many soybean diseases have been linked to restriction fragment length polymorphism (RFLP), RAPD (Randomly Amplified Polymorphic DNA), and STS (Sequence Tag Sites) genome markers. These include bacterial blight, downy mildew (Bernard and Cremeens, 1971), phytophthora root rot (Diers et al. 1992), powdery mildew (Lohnes and Bernard, 1992), soybean rootknot nematode infection (Luzzi et al. 1994), phomopsis seed decay, cyst nematode infection (Baltazar and Mansur 1992; Boutin et al. 1992; Rao-Arelli et al. 1992; Young 1996), soybean mosaic virus (Chen et al. 1993), soybean rust (Hartwig and Bromfield 1983), stem canker (Bowers et al. 1993; Kilen and Hartwig 1987), sudden death syndrome (Prabhu et al. 1996), purple seed stain and leaf blight, and brown spot disease.

Both YAC (yeast artificial chromosome) and BAC (bacterial artificial chromosome) soybean libraries have been constructed (Funk and Colchinsky, 1994), and resistance markers have been assigned to particular clones in these libraries. The availability of these gene sequences will allow for insertion of DNA fragments Ire encoding such genes into SIRE-1 proretrovirus-derived vectors of the present invention using standard recombinant techniques as have been described above (Sambrook et al., 1989). The recombinant vector may then be transduced into target plant cells, where the resistance gene may be expressed episomally or following integration of the vector into the host plant genome.

Transfer of resistance to viral infection to target plant cells is an important object of the present invention. The expression of a viral coat protein in a plant has been shown to diminish the ability of the virus to subsequently infect the plant and spread systemically; thus viral resistance may be mediated by vector-sponsored transfer of viral gene sequences into susceptible plant hosts (Beachy, 1990; Fitchen and Beachy, 1993). Many different viral coat protein genes have been introduced into plant genomes, expressed, and found to confer viral tolerance, including tobacco mosaic virus, cucumber mosaic virus, alfalfa mosaic virus, tobacco streak virus, tobacco rattle virus, potato viruses X and Y, and tobacco etch virus (Beachy, 1990; Gasser and Fraley, 1989; Golemboski et al., 1990; Hemenway et al., 1988; Hill et al., 1991). This approach to viral resistance is especially promising, as the introduction of a viral coat protein from one virus using the vectors of the present invention may often confer tolerance to a range of seemingly unrelated viruses (Beachy, 1990). Moreover, transgenic plants expressing viral coat proteins exhibit viral tolerance in the field as well as in a laboratory setting (Nelson et al., 1988).

Plants may also be transformed with a retroviral vector encoding an antisense RNA complementary to a plant virus polynucleotide. Expression of antisense RNA against viral sequences may provide tolerance against the virus by interfering with either the translation of viral mRNAs or the replication of the viral genome. Expression of antisense RNA has been found to confer viral resistance in, among others, potato, tobacco, and cucumber plants (Beachy, 1990; Day et al., 1991; Hemenway et al., 1988; Rezaian et al., 1988).

Using the present invention, DNA fragments encoding viral coat proteins or antisense RNA complementary to viral RNA transcripts may be recombinantly inserted into the SIRE-1 proretrovirus, transduced into susceptible plants, and expressed to confer resistance to a virus.

B. Herbicide Tolerance

The use of herbicides is limited in part by their toxicity to crop species and by the development of resistance in "weed" species (Hathaway, 1989). Increasing tolerance to herbicides may increase yield and augment the spectrum of herbicides available for use to curtail weed growth. A wider range of suitable herbicides may also retard the development of resistance in weed species (LeBaron and McFarland, 1990), thereby decreasing the overall need for herbicides. Herbicide classes include, for example, acetanilides (e.g., alachlor), aliphatics (e.g., glyphosphate), dinitroanilines (e.g., trifluralin), diphenyl esters (e.g., acifluorfen), imidazolinones (e.g., imazapyr), sulfonylureas (e.g., chlorsulfuron), and triazines (e.g., atrazine).

Two general approaches may be taken in engineering herbicide tolerance: one may alter the level or sensitivity of the target enzyme for the herbicide (such as by altering the enzyme itself, or by decreasing the level or activity of a herbicide transporter), or incorporate or increase the activity of a gene that will detoxify the herbicide (Hathaway, 1989; Stalker, 1991).

An example of the first approach is the introduction (using the vectors and viruses of the present invention) into various crops of genetic constructs leading to overexpression of the enzyme EPSPS (5-enolpyruvylshikimate-3-phosphate synthase), or isoenzymes thereof exhibiting increased tolerance, which confers resistance to the active ingredient in the widely-used herbicide Roundup™, glyphosphate (Shah et al., 1986). The gene for EPSPS was isolated from glyphosphate-resistant *E. coli,* given a plant promoter, and introduced into plants, where it conferred resistance to the herbicide. Transgenic species carrying resistance to glyphosphate have been developed in tobacco, petunia, tomato, potato, cotton, and Arabidopsis (della-Cioppa et al., 1987; Gasser and Fraley, 1989; Shah et al., 1986).

Similarly, resistance to sulfonylurea compounds, the active ingredients in Glean™ and Oust™ herbicides, has been produced by the introduction of site-specific mutant forms of the gene encoding acetolactate synthase (ALS) into plants (Haughn et al., 1988). Resistance to sulfonylureas has been transferred using this method to tobacco, Brassica, and Arabidopsis (Miki et al., 1990).

Bromoxynil is a herbicide that acts by inhibiting photosystem II. Rather than attempting to modify the target plant gene, resistance to bromoxynil has been conferred by the introduction of a gene encoding a bacterial nitrylase, which can inactivate the compound before it contacts the target enzyme. This strategy has been used to confer bromoxynil resistance to tobacco plants (Stalker et al., 1988).

Genes encoding wild-type or mutant forms of endogenous plant enzymes targeted by herbicide compounds, or enzymes that inactivate herbicide compounds, may be recombinantly inserted into SIRE-1 or vectors derived therefrom and transduced into plant cells. The genes may then be expressed under the control of plant- or tissue-specific promoters (Perlak et al., 1991) to confer herbicide resistance to the transformed plant. The overexpression of normal or mutant forms of enzymes normally present in the wild-type progenitor plant is preferred, as this may decrease the probability of deleterious effects on crop performance or product quality.

C. Insect Resistance

Transduction of functional genes encoding insecticidal products into plants may lead to crop strains that are intrinsically tolerant of insect predators. Such plants would not have to be treated with expensive and ecologically hazardous chemical pesticides. In addition, such insecticides would be effective at much lower concentrations than exogenously applied synthetic pesticides, and because biological insecticides are very specific, they are generally not hazardous to the food consumers.

Insect resistance in plants is generally provided by toxins or repellents (Gatehouse et al., 1991). Using the present invention, insecticidal protoxin genes derived from, for example, several subspecies of *Bacillus thuringiensis* (Vaeck et al., 1987), may be transduced into plant cells and constitutively expressed therein. This protoxin does not persist in the environment and is non-hazardous to mammals, making it a safe means for protecting plants. The gene for the toxin has been introduced and selectively expressed in a number of plant species including tomato, tobacco, potato, and cotton (Gasser and Fraley, 1989; Brunke and Meussen, 1991).

The trypsin inhibitor protein from cowpea is also an effective insecticide against a variety of insects: its presence restricts the ability of insects to digest food by interfering with hydrolysis of plant proteins (Hilder et al., 1987). As the trypsin inhibitor is a natural plant protein, it may be expressed in plants without adversely affecting the physiology of the host. There are several potential drawbacks to the use of the cowpea trypsin inhibitor, however. Relative to the *B. thuringiensis* toxin, higher concentrations of inhibitor are required for insecticidal effectiveness (Brunke et al., 1991). Thus, production of the inhibitor may require a more powerful transcriptional promoter (Perlak et al., 1991), and may be more energetically costly for the host plant. In addition, the inhibitor is active in mammalian digestive systems unless inactivated prior to consumption. Inactivation may be accomplished by heating, however, so this may not be a significant drawback to the use of the inhibitor in most crop plants. Moreover, in most crops, the expression of the inhibitor may be restricted to those plant tissues such as leaves or roots that are most exposed to insect predators but are not consumed by mammals through the use of tissue-specific promoter sequences operably linked to the inhibitor gene (Perlak et al., 1991).

These exemplary genes conferring insect resistance or repellence may be inserted into SIRE-1 proretrovirus derived vectors using recombinant methods well-known in the art. These recombinant vectors may then be transduced into soybean and other plants. As more insect resistance and repellence genes are identified, these may be recombinantly inserted into the SIRE-1-derived gene transfer vector and expressed in host plants.

D. Enhanced Nitrogen Fixation and/or Nodulation

Genes whose expression contributes to greater nitrogen fixation and nodulation (Gresshoff and Landau-Ellis, 1994; Qian et al. 1996) may be overexpressed in plant cells by transduction of a recombinant SIRE-1 vector containing DNA fragments from which those genes may be expressed. Alternatively, expression of those genes whose expression leads to reduced nitrogen fixation or nodulation (Wu et al. 1995) may be modulated by the SIRE-1-mediated expression of recombinantly inserted DNA fragments encoding antisense transcripts. Manipulation of these genes may lessen or obviate the current great need for nitrogen-based fertilizers.

E. Enhanced Vigor and/or Growth

Genes from wild progenitor species or non-related species whose expression results in economically valuable growth traits often found in wild progenitor species or non-related species have been discovered (Allen, 1994; Takahashi and Asanuma, 1996). Such genes or gene fragments may be placed under the control of heterologous or native promoters to create a gene cassette, and such cassettes may be recombinantly inserted into SIRE-1 or vectors derived therefrom. These recombinant vectors may then be transduced into plant cells, where expression of the proteins encoded by such genes may lead to the development of plant phenotypes exhibiting economically valuable growth characteristics.

F. Altered Seed Oil/Carbohydrate/Protein Production

Markers have been identified for several genes associated with soybean seed protein and oil content (Lee et al. 1996; Moreira et al. 1996). Transduction and expression of these genes within plants may result in greater seed oil production with lowered linolenic acid content, enhanced seed storage protein production, diminished raffinose-derived oligosaccharide levels, decreased lipoxygenase levels, or decreased protease inhibitor content (which may decrease the nutritive value of some plant proteins in animal feed due to decreased hydrolysis in the digestive tracts of animals). Such genes may be recombinantly inserted into SIRE-1 proretrovirus or vectors derived therefrom, and the recombinant virus or vector may then be used to introduce such genes into plants or plant cells where they may be expressed and may influence the plant phenotype.

The potential food value of certain grains may be improved by altering the amino acid composition of the seed storage proteins. This may be accomplished in at least two ways. First, genes encoding heterologous seed storage proteins composed of a more desirable amino acid mix may be transferred into plants using the vectors and methods of the present invention with an undesirable seed storage protein amino acid composition. This approach has been utilized in several model studies: an oleosin gene from maize was successfully transferred and expressed in Brassica (Lee et al., 1991), and a phaseolin gene from a legume was expressed, and the seed storage protein was appropriately compartmentalized, in tobacco plants (Altenbach et al., 1989).

Second, genes encoding endogenous seed storage proteins may be mutated to contain a more desirable amino acid composition and reintroduced into the host plant using the vectors of the present invention (Hoffman et al., 1988). The effect of these amino acid substitutions on protein conformation and compartmentalization may be lessened by targeting the substitutions to the hypervariable regions near the carboxy-terminus of most seed storage proteins (Dickinson et al., 1990). Genes encoding proteins with altered amino acid compositions may be incorporated into the SIRE-1 retroviral or vectors derived therefrom, and the recombinant virus or vector may then be used to introduce the genes into plant cells in order to introduce changes in protein amino acid composition.

G. Heterologous Protein Production

The present invention contemplates recombinant SIRE-1 virus or vectors derived therefrom that may be used to introduce genes encoding technical enzymes, heterologous storage proteins, or novel polymer-producing enzymes, thus allowing crops to become a novel source for these products.

EXAMPLE 10

Use of SIRE-1 to Induce and Tag Mutations in a Plant Genome

An important object of this invention is the use of the SIRE-1 proretrovirus to establish new landmarks in plant genomes, and to induce and trace new mutations. SIRE-1 may be used to link mutagenesis and element expression. Somaclonal variation has been demonstrated for soybean (Amberger et al., 19921—Freytag et al., 1989; Graybosch et al., 1987; Roth et al., 1989), for example, but little is known about the agents that induce the heritable changes. Persons of ordinary skill in the art will be able to identify new SIRE-1 insertion sites in plant genomes and to correlate these new sites with variant phenotypes. Homozygosity at insertion sites may theoretically be achieved in the $F_1$ progeny, while dominant insertions may be differentiated from pre-existing integration events if the active element possesses a reporter gene like GUS or Npt. Phenotypes may then be correlated with the newly tagged genomic sites, and sequences flanking the sites may be easily cloned and sequenced (Sambrook, et al., 1989).

SIRE-1 may also be used to investigate the relationship between "genomic stress" and transposable element activity by seeking clues in the LTR regions to the identity of host proteins that might regulate element expression. The presence and expression of these proteins may then be correlated with the adverse conditions known to induce element expression.

The availability of a functional proretrovirus in a major plant group has far-ranging applications to applied genetic manipulations and to basic biological problems concerning gene function, genome organization, and evolution. A better understanding of these issues may be valuable in identifying and mapping important new loci. Understanding the relationships between plant health and element mobilization may provide invaluable insights into short- and long-term consequences of transposition. If retroelements have played a significant role in adaptive mutation in natural populations, then plant geneticists may be able to accelerate and direct the process to generate new resistant alleles. New insertion sites would be "tagged" by the element and it may be possible to distinguish these sites from pre-existing loci by competitive hybridization schemes. It should then be possible to clone and characterize the disrupted loci. In addition, if the element has contributed to genotypic changes that have persisted under the pressure of selection, then important loci may be closely linked to the element, a feature that may make it easier to map and isolate coding regions by element-anchored polymorphisms.

EXAMPLE 11

Modification of SIRE-1 Vectors to Effect Directed Integration

Retroviral integration systems show little target site specificity, and random insertions into a target cell genome may have undesirable consequences: integration near cellular proto-oncogenes may lead to ectopic gene activation and tumor production (Shiramazu et al., 1994), and random integration may also inactivate essential or desirable genes (Coffin, 1990). Therefore, the ability to direct the integration of a plant proretrovirus to a limited region of a target plant cell genome is very desirable.

One manner by which directed integration may be effected is via "tethering" of the integration machinery to a specific target sequence. This may be accomplished by fusion of a sequence-specific DNA-binding domain to the integrase sequence of the SIRE-1 proretrovirus (Kirchner et al., 1995). The nucleotide sequence encoding the DNA-binding domain from a protein known to bind to a specific locus in the genome of a plant (i.e., a transcriptional enhancer for a gene whose expression is commercially disadvantageous) may be recombinantly inserted in-frame and just downstream from the 3' end of the SIRE-1 nucleotide sequence encoding the carboxy-terminus of the pol region (i.e., at the carboxy-terminus of the integrase protein, which is a product of pol cleavage). The DNA-binding domain may then act to "guide" the integrase protein and the SIRE-1 polynucleotide to the genetic locus to be insertionally mutated by SIRE-1.

EXAMPLE 12

Determination of the SIRE-1 Insertion Site in the Soybean Genome

The sequence of the flanking genomic DNA from the SIRE-1 genomic clone may be used to generate probes for determination of the genomic insertion site. Restriction enzyme digests of genomic DNA from a variety of G. max cultivars, G. soja, and other plant species (for example, G. tabacina, G. canescens, and G. tormentella) will be electrophoretically fractionated on agarose gels, transferred to nylon membranes, and hybridized with the flanking DNA probe(s). If a band to which the probe(s) hybridize is polymorphic, the relation of the polymorphism to the presence of a SRRE-1 insert may be determined by hybridization with a SIRE-1 LTR-specific probe. A SIRE-1-related polymorphism among cultivars would strongly support functional transposition of the SIRE-1 family in the recent past.

The above examples support that conclusion that SIRE-1 is an endogenous family of proretroviruses whose genomic structure is based on a copia-like organization. In contrast, the genomic organization of all animal retroviruses (from vertebrates and Drosophila) is patterned after gypsy-like retrotransposons. Thus, SIRE-1 is clearly a plant retroviral element that is evolutionarily far diverged from animal retroviruses.

Neither retroviral genomes nor virions have been reported in plants, although both classes of retrotransposons are otherwise widespread in nature. Therefore, SIRE-1 is the first known plant proretrovirus. Few plant virus genomes encode an envelope protein. Those that do—rhabdoviruses and bunyaviruses—also infect animal hosts where envelope proteins sponsor viral-host cell membrane fusion. It is not known whether plant cell walls would preclude this mode of transfer.

SIRE-1 may originally have been an invertebrate retrovirus. Its ability to integrate into plant genomes and the presence of envelope protein-encoding regions suggests the possibility that at one time it may have served as a "shuttle vector" between and among animal and plant hosts. Judging by its copy number it has clearly been successful in G. max.

The overall restriction site homogeneity of family members, the presence of long, uninterrupted ORFs within and adjacent to the retroviral insert, the strong homologies of the env, gag, int, RT and RH domains to those from known retrotransposons, and the near-identity of the LTRs indicate that SIRE-1 is not an evolutionary relic, but an active proretrovirus. As such, it may be utilized to influence the organization and expression of soybean and possibly other plant genomes.

From the foregoing it may be appreciated that, although specific embodiments of the invention have been described herein for purposes of illustration, various modifications may be made without deviating from the spirit and scope of the invention (as set out in the appended claims).

REFERENCES CITED

The following publications which were cited in the specification are incorporated in their entirety by reference herein.

Ahlquist, P., R. French, J. J. Bujarski. Molecular studies of Brome mosaic virus using infectious transcripts from cloned cDNA. Adv. Virus Res. 32:214–242 (1987).

Ahlquist, P., R. F. Pacha. Gene amplification and expression by RNA viruses and potential for further application to plant gene transfer. Physiol. Plant. 79:163–167 (1990).

Altenbach, S. B., K. W. Pearson, G. Meeker, L. C. Staraci, and S. S. M. Sun. Enhancement of the methionine content of seed proteins by the expression of a chimeric gene encoding a methionine-rich protein in transgenic plants. Plant Mol. Biol. 13:513 (1989).

Amberger, L. A., R. G. Palmer and R. C. Shoemaker. Analysis of culture-induced variation in soybean. Crop Sci. 32:1103–1108 (1992).

Ashfield, T., N. T. Keen, R. I. Buzzell, R. W. Innes. 1995. Soybean resistance genes specific for different Pseudomonas syringae avirulence genes are allelic, or closely linked, at the RPGI locus. Genetics 141:1597.

Baltazar, M B, Mansur, L. 1992. Identification of restriction fragment length polymorphisms to map soybean cyst nematode resistance genes in soybean. Soybean Genet. Newslett. 19: 120.

Beachy, R. N. 1990. Plant transformation to confer resistance against virus infection, in Gene Manipulation in Plant Improvement, Vol. 2, Gustafson, J. P., ed., Plenum Press, New York.

Berg, D. E. and M. M. Howe, eds. 1989. Mobile DNA, ASM Washington, D.C.

Bernard, R. L., Cremeens, C. R. 1971. A gene for general resistance to downy mildew of soybeans. J. Hered. 62:359.

Bi, Y.-A. and H. M. Laten. 1996. Sequence analysis of a cDNA containing the gag and prot regions of the soybean retrovirus-like element, SIRE-1. Plant Mol. Biol. 30:1315.

Boeke, J. D. 1989. Transposable elements in *Saccharomyces cerevisiae*. In Mobile DNA, D. E. Berg and M. M. Howe, eds., ASM, Washington, D.C., pp. 335–374.

Boerma, H R, Harris, B B, Kuhn, C W. 1975. Inheritance of resistance to cowpea chlorotic mottle virus in soybeans, Crop Sci. 15: 849.

Brettell, R. I. S. and E. S. Dennis. 1991. Reactivation of a silent Ac following tissue culture is associated with heritable alterations in its methylation pattern. Mol. Gen. Genet. 229, 365–372.

Brisson, N., J. Paszkowski, J. R. Penswick, B. Gronenborn, I. Potrykus, T. Hohn. 1984. Expression of a bacterial gene in plants by using a viral vector. Nature 310, 511–14.

Britten, R. J., Proc. Natl. Acad. Sci. USA 92, 599 (1995).

Britten, R. J., T. J. McCormack, T. L. Mears, E. H. Davidson, J. Mol. Evol. 40, 13 (1995).

Brunke, K. J. and R. L. Meeusen. 1991. Insect control with genetically engineered crops. Trends Biotechnol. 9, 197.

Boutin, S, Ansari, H, Concibido, V, Denny, R, Orf, J, Young, N. 1992. RFLP analysis of cyst nematode resistance in soybeans. Soybean Genet. Newslett. 19: 123.

Burmeister, M. and H. Lehrach. Trends Genet. 12:389 (1996).

Bureau, T. E., S. E. White, S. R. Wessler, Cell 77:479 (1994).

Buss, G. R., Roane, C. W., Tolin, S. A., Vinardi, T. A. 1985. A second dominant gene for resistance to peanut mottle virus in soybeans. Crop Sci. 25:314.

Cal, H. and M. Levine. 1995. Modulation of enhancer-promoter interactions by insulators in the Drosophila embryo. Nature 376:533–536.

Casacuberta, J. M., S. Vemhettes and M.-A. Grandbastien. 1995. Sequence variability within the tobacco retrotransposon Tnt1 population. EMBO J. 14, 2670–2678.

Caverec, L. and T. Heidmann. 1993. The Drosophila copia retrotransposon contains binding sites for transcriptional regulation by homeoproteins. Nucl. Acids Res. 21, 5041–5049.

Cavarec, L., S. Jensen and T. Heidmann. 1994. Identification of a strong transcriptional activator for the copia retrotransposon responsible for its differential expression in Drosophila hydei and melanogaster cell lines. Biochem. Biophys. Res. Commun. 20–31, 392–399.

Chambers, P., C. R. Pringle, A. J. Easton, J. Gen. Virol. 71, 3075 (1990).

Chan, D. C., D. Fass, J. M. Berger, P. S. Kim, Cell 89, 263 (1997).

Chen, P., Buss, G. R., Tolin, S. A. 1993. Resistance to soybean mosaic virus conferred by two independent dominant genes in PI 486355. J. Hered. 84: 25.

Choi, S.-Y. and D. V. Faller. 1994. The long terminal repeats of a murine retrovirus encode a transactivator for cellular genes. J. Biol. Chem. 269, 19691–19694.

Dahlberg, J. E., R. C. Sawyer, J. M. Taylor, A. J. Faras, W. E. Levinson, H. M. Goodman, and J. M. Bishop. 1974. Transcription of DNA from the 70S RNA of Rous sarcoma virus. 1. Identification of a specific 4S RNA which serves as primer. J. Virol. 13:1126–1133.

Dalgleish, A. G., P. C. L. Beverly, P. R. Clapham, D. H. Crawford, M. F. Greaves, and R. A. Weiss. 1984. The CD4 antigen is an essential component of the receptor for the AIDS retrovirus. Nature 312, 763–767.

Day, A. G., E. R. Bejarano, K. W. Buck, M. Burrell, and C. P. Lichtenstein. 1991. Expression of an antisense viral gene in transgenic tobacco confers resistance to the DNA virus tomato golden mosaic virus. Proc. Natl. Acad. Sci. U.S.A. 88, 6721.

Deleage, G., and B. Roux, Prot. Engng. 1, 289 (1987).

della-Cioppa, G., S. C. Bauer, M. L. Taylor, D. E. Rochester, B. K. Klein, D. M. Shah, R. T. Fraley, and G. M. Kishore. 1987. Targeting a herbicide resistant enzyme from Escherichia coli to chloroplasts of higher plants. Bio/Technology 5, 579.

Di, R., V. Purcell, G. B. Collins, S. A. Ghabrial. 1996. Production of transgenic soybean lines expressing the bean pod mottle virus coat protein precursor gene. Plant Cell. Reports 15:746.

Dickinson, C. D., M. P. Scott, E. H. A. Hussein, P. Argos, and N. C. Nielsen. 1990. Effect of structural modifications on the assembly of a glycinin subunit. Plant Cell. 2, 403.

Diers, B. W., Mansur, L., Imsande, J., Shoemaker, R. C. 1992. Mapping phytophthora resistance loci in soybean with resistance fragment length polymorphism markers. Crop Sci. 32: 377.

Eickbush, T. H., in The Evolutionary Biology of Viruses, S. S. Morse, Ed. (Raven Press, New York, 1994) pp. 121–157.

Engels, W. R. 1989. P elements in Drosophila melanogaster. In Mobile DNA, D. E. Berg and M. Howe, eds., ASM, Washington, D. C., pp. 437–484.

Fass, D., S. C. Harrison, P. S. Kim, Nature Struct. Biol. 3, 465 (1996).

Federoff, N. V. 1989. Maize transposable elements. In Mobile DNA, D. E. Berg and M. M. Howe, eds., ASM Washington, D. C., pp. 375–41 1.

Felder, H., A. Herzceg, Y. deChastonay, P. Aeby, H. Tobler, F. Muller, Gene 149, 219 (1994)

Finnegan, D. J. 1989. Eukaryotic transposable elements and genome evolution. Trends Genet. 5, 103107.

Flavell, A. J., V. Jackson, M. P. Iqbal, I. Riach, S. Waddell, Mol. Gen. Genet. 246, 65 (1995).

Flavell, A. J., D. B. Smith and A. Kumar. 1992. Extreme heterogeneity of Ty1-copia group retrotransposons in plants. Mol. Gen. Genet. 231, 233–242.

Fontenot, J. D., N. Tjandra, C. Ho, P. C. Andrews, R. C. Montelaro, J. Biomol. Struct. Dynam. 11, 821 (1994).

Freytag, A. H., A. P. Rao-Arelli, S. C. Anand, I. A. Wrather and L. D. Owens. 1989. Somaclonal variation in soybean plants regenerated from tissue culture. Plant Cell Rep. 8, 199–202.

Friesen, P. D., and M. S. Nissen, Mol. Cell. Biol. 10, 3067 (1990).

Gallaher, W. R., J. M. Ball, R. F. Garry, A. M. Martin-Amedee, R. C. Montelaro, AIDS Res. Hum. Retroviruses 11, 191 (1995).

Gallaher, W. R., J. M. Ball, R. F. Garry, M. C. Griffin, R. C. Montelaro, AIDS Res. Hum. Retroviruses 5, 431 (1989).

Georgiev, P. G. and V. G. Corces. 1995. The su(Hw) protein bound to gypsy sequences in one chromosome can repress enhancer-promoter interactions in the paired gene located on the other homolog. Proc. Natl. Acad. Sci. USA 92. 5184–5 1 S&

Georjon, C., and G. Deleage, Comput. Applic. Biosci. 11, 681 (1995).

Georjon, C., and G. Deleage, Prot. Engng. 7, 157 (1994).

Gever, P. K. and V. G. Corces. 1992. DNA position-specific repression of transcription by a Drosophila zinc finger protein. Genes Dev. 6, 1865–1873).

Gibrat, J. F., J. Garnier, B. Robson, J. Mol. Biol. 198, 425 (1987).

Gijzen, M., T. MacGregor, M. Bhattacharyya, R. Buzzell. 1996. Temperature-induced susceptibility to Phytophthora sojae in soybean isolines carrying different RPS genes. Physiol. Mol. Plant Path. 48:209.

Golemboski, D. B., G. P. Lomonossoff, and M. Zaitlin. 1990. Plants transformed with a tobacco mosaic virus nonstructural gene sequence are resistant to the virus. Proc. Natl. Acad. Sci. U.S.A. 87, 6311.

Grandbastien, M.-A. 1992. Retroelements in higher plants. Trends Genet. 8, 103–108.

Grandbastien, M.-A., A. Spielmann and M. Caboche. 1989. Tnt1, a mobile retroviral-like transposable element of tobacco isolated by plant cell genetics. Nature 337, 376–380.

Graybosch, R. A., N. E. Edge and X. Delannay. 1987. Somaclonal variation in soybean plants regenerated from cotyledonary node tissue culture system. Crop Sci. 27, 803–806.

Gresshoff, P. M. and D. Landau-Ellis. 1994. Molecular mapping of soybean nodulation genes. In Plant Genome Analysis, P. Gresshoff, ed., CRC Press, Boca Raton, pp. 97–112.

Groose, R. W. and R. G. Palmer. 1987. New mutations in a genetically unstable line of soybeans. Soybean Genet. Newsl. 14, 164–1610.

Groose, R-W., H. D. Weigelt and R-G. Palmer. 1988. Somatic analysis of unstable mutation for anthocyanin pigmentation in soybean. 1. Heredity 79, 263–267.

Hagen, G., and T. Guilfoyle. 1985. Rapid induction of selective transcription by auxins. Mol. Cell Biol. 5, 1197.

Harlow, E., and D. Lane. 1985. Antibodies: A Laboratory Manual. Cold Spring Harbor Laboratory Press, Cold Spring Harbor, N.Y.

Hartwig, E. E., Bromfield, K. R. 1983. Relationships among three genes conferring specific resistance to rust in soybeans. Crop Sci. 23: 237.

Haughn, G. W., et al. 1988. Mol. Gen. Genet. 211, 266.

Hemenway, C., R.-X. Fang, W. K. Kaniewski, N.-H. Chua, and N. E. Tumer. 1988. Analysis of the mechanism of insect resistance engineered into tobacco. Nature 330, 160.

Hill, K. K., N. Jarvis-Eagan, E. L. Halk, K. J. Krahn, L. W. Liao, R. S. Mathewson, D. J. Merlo, S. E. Nelson, K. E. Rashka, and L. S. Loesch-Fries. 1991. The development of virus-resistant alfalfa, *Medicago sativa* L. Bio/Technology 9, 373.

Hirochika, H. 1993. Activation of tobacco retrotransposons during tissue culture. EMBO J. 12, 2521–2528.

Hoffman, L. M., D. D. Donaldson, and E. M. Herman. 1988. A modified storage protein is synthesized, processed, and degraded in the seed of transgenic plants. Plant Mol. Biol. 11, 717.

Hofmann, K., and W. Stoffel, Biol. Chem. Hoppe-Seyler 347, 166 (1993).

Horsch, R. B., et al. 1984. Science 223, 496.

Hsu, H. T., and R. H. Lawson. 1991. Direct tissue blotting for detection of tomato spotted wilt virus in Impatiens. Plant Dis. 75, 292.

Hu, W., O. P. Das and J. Messing. 1995. Zeon-1, a member of a new maize retrotransposon family. Mol.Gen. Genet. 248, 471–480.

Hunter, E., and R. Swanstrom, Curr. Top. Microbiol. Immunol. 157, 187 (1990)

Hutchinson III, C. A., S. C. Hardies, D. D. Loeb, W. R. Shehee & M. H. Edgell. 1989. LINES and related retroposons: long interspersed repeated sequences in the eucaryotic genome. In Mobile DNA, D. E. Berg and M. M. Howe, eds., ASM, Washington, D. C., pp.593–617.

Inouye, S., S. Yuki, K. Saigo, Eur. J. Biochem. 154, 417 (1986).

Johns, M. A., J. Mottinger and M. Freeling. 1985. A low copy number, copia-like transposon in maize. EMBO J. 4, 1093–1102.

Kaeppler, S. M. and R. L. Phillips. 1993. Tissue culture-induced DNA methylation variation in maize. Proc. Natl. Acad. Sci. USA 90, 8773–8776.

Kasuga, T, Gijzen, NC, Buzzelli, R, Bhattacharyya, M. 1996. Isolation and mapping of amplified fragment length polymorphisms (AFLP) DNA markers that are linked to the RPS I locus of soybean. (Abstract) Plant Genome IV, San Diego, 1996.

Katz, R. A. and J. E. Jentoft. 1989. What is the role of the Cys-His motif in retroviral nucleocapsid (NC) proteins? Bioessays II, 176–18 1.

Keen, N T, Buzzell, R I. 1991. New disease resistance genes in soybean against Pseudomonas syringae pv glycinea: evidence that one of them interacts with a bacterial elicitor. Theor. Appl. Genet. 81: 133.

Keim, P, Schupp, J M, Ferreira, A, Zhu, T, Shi, L, Travis, S E, Clayton, K, Webb, D M. 1996. A high density soybean genetic map using RFLP, RAPD, and AFLP genetic markers. (Abstract) Plant Genome IV, San Diego, 1996.

Kilen, T C, Hartwig, E E. Identification of single genes controlling resistance to stern canker in soybean. Crop Sci. 27: 863.

Kim, A., C. Terzian, P. Santamaria, A. Pelisson, N. Prudhomme, A. Bucheton, Proc. Natl. Acad. Sci. USA 91, 1285 (1994).

Kina, C. C. 1992. Modular transposition and the dynamic structure of eukaryotic regulatory evolution. Genetica 86, 127–142.

Laten, H. M. and R. O. Morris. 1993. SIRE-1, a long, interspersed repetitive DNA element from soybean with weak sequence similarity to retrotransposons: initial characterization and partial sequence. Gene 134, 153–159.

Lee, S-H, Tamulonis, J, Bailey, M, Man, R, Ashley, D, Parrott, W, Boerma, R, Carter, Jr, T, Shipe, E, Hussey, R. 1996. Molecular markers associated with soybean seed protein and oil across populations and locations. (Abstract) Plant Genome IV, San Diego, 1996.

Lee, W. S., J. T. C. Tzen, J. C. Kridl, S. E. Radke, and A. H. C. Huang. 1991. Maize oleosin is correctly targeted to seed oil bodies in Brassica napus transformed with the maize oleosin gene. Proc. Natl. Acad. Sci. U.S.A. 88, 6181.

Levin, J. M., B. Robson, J. Garnier, FEBS Lett. 205, 303 (1986).

Lim, J. K. and M. J. Simmons. 1994. Gross chromosomal rearrangements mediated by transposable elements in *Drosophila melanogaster*. Bioessays 16, 269–275.

Lohnes, D G, Bernard, R I. 1992. Inheritance of resistance to powdery mildew in soybeans. Plant Disease 76: 964.

Lohning, C. and M. Ciriacy. 1994. The TYE7 gene of *Saccharomyces cerevisiae* encodes a putative bHLH-LZ transcription factor required for Ty1-mediated gene expression. Yeast 10, 1329–1339.

Lupas, A., M. Van Dyke, J. Stock, Science 252, 1162 (1991)

Luzzi, B M, Boerma, H R, Hussey, R S. 1994. A gene for resistance to the soybean root-knot nematode in soybean. J. Hered. 85: 484.

Luzzi, B M, Boerma, H R, Hussey, R S. 1994. Inheritance of resistance to the soybean root-knot nematode in soybean. Crop Sci. 34: 1240.

Ma, G., P. Chen, G. R. Buss, S. A. Tolin. 1995. Genetic characteristics of two genes for resistance to soybean mosaic virus in P1486355 soybean. Theor. Appl. Genetics 91:907.

Mansky, L. M., D. P. Durand and J. H. Ell. 1991. Effects of temperature on the maintenance of resistance to soybean mosaic virus in soybean. Phytopathol. 8 1, 53 5–53) 8.

Matthews, R. E. F., Plant Virology (Academic Press, New York, 1991).

McClintock, B. 1984. The significance of responses of the genome to challenge. Science 226, 792–801.

McDonald, J. F. 1990. Evolution and consequences of transposable elements. Curr. Opin. Genet. Devel. 3, 855–864.

McDonald, J. F. 1990. Macroevolution and retroviral elements. BioScience 40, 183–191.

McDonald, J. F., D. J. Strand, M. R. Brown, S. M. Paskewitz, A. K. Csink and S. H. Voss. 1988. Evidence of hostmediated regulation of retroviral element expression at the posttranscriptional level. In Eukaryotic Transposable Elements as Mutagenic Agents, M. E. Lambert, J. F. McDonald and I. B. Weinstein, eds., Cold Spring Harbor Laboratory, New York, pp. 219–234.

McEntee, K. and V. A. Bradshaw. 1988. Effects of DNA damage on transcription and transposition of Ty retrotransposons of yeast. In Eukaryotic Transposable Elements as Mutagenic Agents, M. E. Lambert, J. F. McDonald and I. B. Weinstein, eds., Cold Spring Harbor Laboratory, New York, pp. 245–253.

Mellentin-Michelotti, J., S. John, W. D. Pennie, T. Williams and G. L. Hager. 1994. The 5' enhancer of the mouse mammary tumor virus long terminal repeat contains a functional AP-2 element. J. Biol. Chem. 269, 31983–31990.

Moreira, M A, Barros, E G, Sediyama, C S, Sediyama, T. 1996. Breeding soybean for high quality seeds assisted by molecular markers. (Abstract) Plant Genome IV, San Diego, 1996.

Murphy, J. E., and S. P. Goff. 1988. Construction and analysis of deletion mutations in the U5 region of Moloney murine leukemia virus: effects on RNA packaging and reverse transcription. J. Virol. 63, 319–327.

Mushegian, A. R. and E. V. Koonin, Arch Virol. 133, 239 (1993).

Nathan, M., L. M. Mertz and D. K. Fox. 1995. Optimizing long RT-PCR. Focus 17, 78–80.

Navot, N., R. Ber, and H. Czosnek. 1989. Rapid detection of tomato yellow leaf curl virus in squashes of plant and insect vectors. Phytopathology 79, 562.

Nelson, R. S., S. M. McCormick, X. Delannay, P. Dube, J. Layton, E. J. Anderson, M. Kaniewska, R. K. Proksch, R. B. Horsch, S. G. Rogers, R. T. Fraley, and R. N. Beachy. 1993. Virus tolerance, plant growth, and field performance of transgenic tomato plants expressing coat protein from tobacco mosaic virus. Bio/Technology 6, 403.

Ngeleka, K, Smith O D. 1993. Inheritance of stem canker resistance in soybean cultivars Crockett and Dowling. Crop Sci. 33: 67.

Padgette, S. R., N. B. Taylor, D. L. Nida, M. R. Bailey, J. MacDonald, L. R. Holden, R. L. Fuchs. 1996. The composition of glyphosphate-tolerant soybean seeds is equivalent to that of conventional soybeans. J. Nutr. 126:702.

Palmgren, M. G. 1994. Capturing of host DNA by a plant retroelement: Bs I encodes plasma membrane H+-ATPase domains. Plant Mol. Blol. 25, 137–140.

Patience, C., D. A. Wilkenson, R. A. Weiss, Trends Genet. 13, 116 (1997).

Paquin, E. and V. M. Williamson. 1988. Effect of temperature on Ty transposition. In Eukaryotic Transposable Elements as Mutagenic Agents, M. E. Lambert, I. F. McDonald and I. B. Weinstein, eds., Cold Spring Harbor Laboratory, New York, pp. 235–244.

Pearl, L. H. and W. R. Taylor. 1987. A structural model for the retroviral proteases. Nature 329, 351354.

Perlak, F. J., R. L. Fuchs, D. A. Dean, S. L. McPherson, and D. A. Fischoff. 1991. Modification of the coding sequence enhances plant expression of insect control protein genes. Proc. Natl. Acad. Sci. U.S.A. 88, 3324.

Peschke, V. M. and R. L. Phillips. 1991. Activation of the maize transposable element Suppressor-mutator (Spm) in tissue culture. Theor. Appl. Genet. 81, 90–97.

Peschke, V. M., R. L. Phillips and B. G. Gengenbach. 1991. Genetic and molecular analysis of tissue culture-derived Ac elements. Theor. Appl. Genet. 821, 121–129.

Phillips, D, Boerma, B R. 1982. Two genes for resistance to race S of Cercospora sojina in soybeans. Phytopathol. 72: 764.

Pinter, A., and W. J. Honnen, J. Virology 62, 1016 (1988).

Pouteau, S., M.-A. Grandbastien and M. Boccara. 1994. Microbial elicitors of plant defense responses activate transcription of a retrotransposon. Plant J. 5, 535–542.

Prabhu, R, Doubler, T W, Chang, SIC, Lightfoot, D A. 1996. Development of sequence characterized amplified regions (SCARs) for marker-assisted selection of soybean lines resistant to sudden death syndrome. (Abstract) Plant Genome IV, San Diego, 1996.

Qian, D., F. L. Allen, G. Stacey, P. M. Gresshoff. 1996. Plant genetic study of restricted nodulation in soybean. Crop Sci. 36(2): 243–49.

Rao-Arelli, A P, Anand, S C, Wrather, A. 1992, Soybean resistance to soybean cyst nematode race 3 is conditioned by an additional dominant gene. Crop Sci. 32: 862.

Rezaian, M. A., K. G. M. Skene, and J. G. Ellis. 1988. Antisense RNAs of cucumber mosaic virus in transgenic plants assessed for control of the virus. Plant Mol. Biol. 11, 463.

Rio, D. C. 1990. Molecular mechanisms regulating Drosophila P element transposition. Annu. Rev. Genet. 24, 543–578.

Robertson, H. D., S. H. Howell, M. Zaitlin, and R. L. Malmberg, eds. 1983. "Plant infectious agents" in Viruses, Viroids, Virusoids, and Satellites. Cold Spring Harbor Laboratory Press, Cold Spring Harbor, N.Y.

Robins, D. M. and L. C. Samuelson. 1993. Retrotransposons and the evolution of mammalian gene expression. In Transposable Elements and Evolution, J. F. McDonald, ed., Kluwer, Dordrecht, pp. 515.

Roth, E. J., B. L. Frazier, N. R. Apuya and K. G. Lark. 1989. Genetic variation in an inbred plant: variation in tissue cultures of soybean (Glycine max (L.) Merrill). Genetics 12: 359–368.

Saigo, K., W. Kugiyama, Y. Matsuo, S. Inouye, K. Yoshioka, S. Yuki, Nature 312, 659 (1984).

Sambrook, J., E. F. Fritsch and T. Maniatis. 1989. Molecular Cloning. Cold Spring Harbor Laboratory: New York.

Sandmeyer, S. B., L. J. Hansen and D. L. Chalker. 1990. Integration-specificity of retrotransposons and retroviruses. Annu. Rev. Genet. 24, 491–518.

Sanger, F., S. Nicklen and A. R. Coulson. 1977. DNA sequencing with chain terminating inhibitors. Proc. Nat. Acad. Sci. USA 74, 5463–5467.

SanMiguel, P., A. Tikhonov, Y.-K. Jin, N, Motchoulskaia, D. Zakharov, A. Melake-Berhan, P. S. Springer, K. J. Edwards, M. Lee, Z. Avramova, J. L. Bennetzen, Science 274, 765 (1996).

Schwarz-Sommer, Z. and H. Saedler. 1987. Can plant transposable elements generate novel regulatory systems? Mol. Gen. Genet. 209, 207–209.

Schwarz-Sommer. Z. and H. Saedler. 1988. Transposition and retrotransposition in plants. In Plant Transposable Elements, 0. Nelson, ed. Plenum Press: New York, pp. 175–187.

Shah, D. M. et al. 1986. Science 233, 478.

Shapiro, J. A. 1983. Mobile Genetic Elements. New York: Academic Press.

Shapiro, J. A. 1992. Natural genetic engineering in evolution. Genetica 86, 99–111.

Sheridan, M. A. and R. G. Palmer. 1977. The effect of temperature on an unstable gene in soybeans. J. Hered. 68, 17–22.

Shih, C. C., J. P. Stoye, and J. M. Coffin. 1988. Highly preferred targets for retrovirus integration. Cell 53, 531–537.

Shoemaker, R, S. Zhao, V. Kanazin, L. Marek. 1996. Phytophthora root rot resistance gene mapping in soybean. (Abstract) Plant Genome IV, San Diego, 1996.

Shoemaker, R. C., L. A. Amberger, R. G. Palmer, L. Oglesby and J. P. Ranch. 1991. Effect of 2,4 dichlorophenoxyacetic acid concentration on somatic embryogenesis and heritable variation in soybean [Glycine max (L) Merr.]. In Vitro Cell. Dev. Biol. 27P, 84–88.

Southern, E. M. 1975. Detection of specific sequences among DNA fragments separated by gel electrophoresis. J. Mol. Biol. 98, 503.

Switzer, W. M. and W. Heneine. 1995. Rapid screening of open reading frames by protein synthesis with an in vitro transcription and translation system. Biotech. 18, 244-1-48.

Takahashi, R., and S. Asanuma. 1996. Association of T gene with chilling tolerance in soybean. Crop Sci. 36:559.

Tanda, S., J. L. Mullor, V. G. Corces, Mol. Cell. Biol. 14, 5392 (1994).

Titus, D. E. 1991. Promega Protocols and Applications Guide. Madison, Wis.

H. B. Urnovitz and W. H. Murphy, Clin. Microbiol. Rev. 9, 72 (1996).

Vaeck, M., A. Reynaerts, H. Hofte, S. Jansens, M. DeBeuckeleer, C. Dean, M. Zabeau, M. Van Montagu, and J. Leemans. 1987. Transgenic plants protected from insect attack. Nature 328, 33.

Varmus, H., and P. Brown, in Mobile DNA, D. E. Berg and M. M. Howe, Eds. (ASM, Washington, D.C., 1989) pp 53–108.

Varmus, H. E. 1982. Form and function of retroviral proviruses. Science 216, 812–821.

Varmus, H. and P. Brown. 1989. Retroviruses. In Mobile DNA, D. E. Berg and M. M. Howe, eds. pp.53–108.

Voytas, D. F., M. P. Cummings, A. Konieczny, F. M. Ausubel and S. R. Rodermel. 1992. copia-like retrotransposons are ubiquitous among plants. Proc. Natl. Acad. Sci. USA 89, 7124–7128.

Watson, J. D., N. H. Hopkins, J. W. Roberts, J. A. Steitz, and A. M. Weiner. 1987. Molecular Biology of the Gene. Menlo Park: Benjamin/Cummings Publishing.

Waugh, R. and J. W. S. Brown. 1991. Plant gene structure and expression. In Plant Genetic Engineering, D. Gierson, ed., Chapman and Hall, New York, pp. 1–37.

Weil, C. F. and S. R. Wessler. The effects of plant transposable element insertions on transcription initiation and RNA processing. 1990. Annu. Rev. Plant Physiol. Plant Mol. Biol. 41, 527–552.

White, S. E., L. F. Habera and S. R. Wessler. 1994. Retrotransposons in the flanking regions of normal plant genes: A role for copia-like elements in the evolution of gene structure and expression. Proc. Nad. Acad. Sci. USA 91, 11792–11796.

Williamson, M. P., Biochem. J. 297, 249 (1994).

Wilson, I. B. H., Y. Gavel, G. von Heijne, Biochem. J. 275, 529 (1991).

Wu, S. C., Q. Lu, A. L. Kriz, J. E. Harper. 1995. Identification of cDNA clones corresponding to two inducible nitrate reductase genes in soybean—analysis in wild-type and NR(1) mutant. Plant Mol. Biol. 29:491–506.

Young, N D. 1996. Genome analysis of soybean cyst nematode resistance in soybean. (Abstract) Plant Genome IV, San Diego, 1996.

Yu, Y. G., M. A.S. Maroof, G. R. Buss. 1996. Divergence and allelomorphic relationship of a soybean virus resistance gene based on tightly linked DNA microsatellite and RFLP markers. Theor. Appl. Genetics 92:64.

```
                      SEQUENCE LISTING

<160> NUMBER OF SEQ ID NOS: 86

<210> SEQ ID NO 1
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n = a, g, c, or t
<220> FEATURE:
<221> NAME/KEY: misc_feature
<222> LOCATION: (5)..(5)
<223> OTHER INFORMATION: n = a, g, c, or t
<220> FEATURE:
<221> NAME/KEY: misc_feature
<222> LOCATION: (14)..(14)
<223> OTHER INFORMATION: n = a, g, c, or t

<400> SEQUENCE: 1
tnttngatcg kgtncartgc tg                                            22

<210> SEQ ID NO 2
<211> LENGTH: 776
<212> TYPE: DNA
<213> ORGANISM: Glycine max
<220> FEATURE:
<221> NAME/KEY: misc_feature
<223> OTHER INFORMATION: SIRE-1 fragment from Glycine max genomic DNA

<400> SEQUENCE: 2
tattggatcg ggtgcagtgc tgtttttggc aggaacaaat tatgtcatgg ttgttctgcc      60
agcagattta tgattaaatc caagtcctct ctggtttcca acattcttcc caagctgtag    120
cacctcatca agcaaatttg agcctttatt cagcatcttt attgatttg tcatgttttc     180 cagtttagag ttcagaaaac caatttctcc tttaagttca gagatttcct cttcatgtgc    240
ctccttctca gcctccagat ttgcaatgac cttctttagt tgtgcttctt gctgaagaat    300
```

| | |
|---|---|
| cttctcactt tgatgcata gttctctata ggatatagca agctcatcaa aagtgatttc | 360 |
| actatctgta tcacttgaat cttcagcaga ttcaaatctc ccagtgagtg cattcacatc | 420 |
| tctgtcagaa tcacttcttg ttcactctct gtatcatcag accgacatac agaaagtcct | 480 |
| ttcctctgct tcttgagatg agtgggacat tcagctttga tgtgtccata gccttcacac | 540 |
| ccatggcatt gaattccttt gctgtgactg gcttttcat ctgacctttt ctggtattca | 600 |
| ctacctttcc tgatgtcgaa agggatgttc cggacatgtg gtttctgcct cctgtccatt | 660 |
| ctgttcagca ctttgttgaa ctgttttcca aggagcacaa ctgcgttagt cagaccttca | 720 |
| tcagtatcca ggtcatactc atcttcttct ccttcagcac tgcacccgat ccaata | 776 |

<210> SEQ ID NO 3
<211> LENGTH: 2417
<212> TYPE: DNA
<213> ORGANISM: Glycine max
<220> FEATURE:
<221> NAME/KEY: misc_feature
<223> OTHER INFORMATION: SIRE-1 cDNA clone

<400> SEQUENCE: 3

| | |
|---|---|
| tccggtccct ggcttggtag cccccagatg taggtgaggt tgcaccgaac tgggttaaca | 60 |
| attctcttgt gttagttact tgtttaatct gttcatacag tcaaacataa tctgcatgtt | 120 |
| ctgaagcgtg atgtcgtgac atccggtacg acatctgtca ttggtatcag aatttcaatt | 180 |
| ggtatcagag caggcactcg aattcactga gtgagatcta gggagataaa ttctgatgaa | 240 |
| catggagaaa gaaggaggac cagtgaacag accaccaatt ctggatggaa ccaactatga | 300 |
| atactggaaa gcaaggatgg tggccttcct caaatcactg gatagcagaa cctggaaagc | 360 |
| tgtcatcaaa gactgggaac atcccaagat gctggacaca gaaggaaagc ccactgatgg | 420 |
| attgaagcca gaagaagact ggactaaaga agaagacgaa ttggcacttg gaaactccaa | 480 |
| agctttgaat gctctattca atggagttga caagaatatc ttcagactga tcaacacatg | 540 |
| cacagtggcc aaggatgcat gggagatcct gaaaaccact catgaaggaa cctccaaagt | 600 |
| gaagatgtcc agattgcaac tattggccac aaaattcgaa aatctgaaga tgaaggagga | 660 |
| agagtgtatt catgactttc acatgaacat tcttgaaatt gccaatgctt gcactgcctt | 720 |
| gggagaaaga atgactgatg aaaagctggt gagaaagatc ctcagatcct tgcctaagag | 780 |
| atttgacatg aaagtcactg caatagagga ggcccaagac atttgcaacc tgagagtaga | 840 |
| tgaactcatt ggttcccttc aaacctttga gctaggactc tcggatagga ctgaaaagaa | 900 |
| gagcaagaat ctggcgttcg tgtccaatga tgaaggagaa aagatgagt atgacctgga | 960 |
| tacagatgaa ggtctgacta atgcagttgt gctccttgga aaacagttca acaaagtgct | 1020 |
| gaacagaatg gacaggaggc agaaaccaca tgtccggaac atccctttcg acatcaggaa | 1080 |
| aggtagtgaa taccagaaaa ggtcagatga aaagcccagt cacagcaaag gatttcaatg | 1140 |
| ccatgggtgt gaaggctatg acacatcaa agctgaatgt cccactcatc tcaagaagca | 1200 |
| gaggaaagga ctttctgtat gtcggtctga tgatacagag agtgaacaag aaagtgattc | 1260 |
| tgacagagat gtgaatgcac tcactgggag atttgaatct gctgaagatt caagtgatac | 1320 |
| agacagtgaa atcacttttg atgagcttgc tacatcctat agaaactat gcatcaaaag | 1380 |
| tgagaagatt cttcagcaag aagcacaact gaagaaggtc attgcaaatc tggaggctga | 1440 |
| gaaggaggca catgaagagg agatctctga gcttaaagga gaagttggtt ttctgaactc | 1500 |
| taaactggaa aacatgacaa aatcaataaa gatgctgaat aaaggctcag atatgcttga | 1560 |

```
tgaggtgcta cagcttggga agaatgttgg aaaccagaga ggacttgggt ttaatcataa     1620
atctgctggc agaataacca tgacagaatt tgttcctgcc aaaatcagca ctggagccac     1680
gatgtcacaa catcggtctc gacatcatgg aacgcagcag aaaaagagta aagaaagaa     1740 gtggaggtgt cactactgtg gcaagtatgg tcacataaag ccctttttgct atcatctaca    1800 tggccatcca catcatggaa ctcaaagtag cagcagcaga aggaagatga tgtgggttcc    1860
aaaacacaag attgtcagtc ttgttgttca tacttcactt agagcatcag ctaaggaaga    1920
ttggtaccta gatagcggct gttccagaca catgacagga gtcaaagaat ttctggtgaa    1980
cattgaaccc tgctccacta gctatgtgac atttggagat ggctctaaag gaaagatcac    2040
tggaatggga aagctagtcc atgatggact tcgttatgtc aaggaataag atcgggctgc    2100
acaatgcaca aggcaagata aaatgtcaaa tgaagaattg aagctgcagg atccatgatg    2160
tcggatacaa tgtccaggac atcctgcccg aaaatactgg agttgctgca caatgcacaa    2220
ggcaagataa aagaagtgaa gctgcaggat ccacgatgtc ggatacgatg tccaggacat    2280
ctggcccgaa atactggac acataaatct gttatatctt taacagatta ttgtgcagtt     2340
agcaacaggt tagacgatct atctttagga acgaactctt ctagttccgg aattcgagct    2400
cggtacccgg ggatcct                                                    2417
```

```
<210> SEQ ID NO 4
<211> LENGTH: 14
<212> TYPE: PRT
<213> ORGANISM: Glycine max

<400> SEQUENCE: 4

Cys His Gly Cys Glu Gly Tyr Gly His Ile Lys Ala Glu Cys
1               5                   10

<210> SEQ ID NO 5
<211> LENGTH: 10
<212> TYPE: PRT
<213> ORGANISM: Glycine max

<400> SEQUENCE: 5

Leu Asp Ser Gly Cys Ser Arg His Met Thr
1               5                   10

<210> SEQ ID NO 6
<211> LENGTH: 22
<212> TYPE: DNA
<213> ORGANISM: Glycine max

<400> SEQUENCE: 6
tggtatcaga gcaggcactc ga                                              22

<210> SEQ ID NO 7
<211> LENGTH: 17
<212> TYPE: DNA
<213> ORGANISM: Glycine max
<220> FEATURE:
<221> NAME/KEY: misc_feature
<223> OTHER INFORMATION: 3' end of SIRE-1 element (sequence is
      identified in the 5' to 3' direction in the sequence listing
      and in the 3' to 5' direction in Figure 12

<400> SEQUENCE: 7
actttaagac tatggtt                                                    17

<210> SEQ ID NO 8
```

<211> LENGTH: 4224
<212> TYPE: DNA
<213> ORGANISM: Glycine max
<220> FEATURE:
<221> NAME/KEY: misc_feature
<223> OTHER INFORMATION: SIRE-1 genomic DNA clone

<400> SEQUENCE: 8

| | | | | | |
|---|---|---|---|---|---|
| gctcgcggcc | gcgagctcta | atacgactca | ctatagggcg | tcgactcgat | cttgttgatg | 60 |
| ataaagttat | cacactggag | catgttgaca | ctgaggaaca | aatagcagat | attttcacaa | 120 |
| aggcattgga | tgcaaatcag | tttgaaaaac | tgaggggcaa | gctgggcatt | tgtctgctag | 180 |
| aggatttata | gcaattactt | ttatctgaac | gtgcttaaac | gttaatagcg | cgttctctac | 240 |
| tgggccaaaa | caaattcgac | cgttgcttca | cacgtccctc | tacattcctc | attcaaactc | 300 |
| atattttcgt | ggtaatctcg | ttttcagcat | tccccaacag | ctctcagaga | tttacgaaac | 360 |
| cattccaaag | gctctgcttc | tccatggcta | cctcaccaaa | agatacttca | tctcctggtt | 420 |
| caccctctgt | accatcatct | ccatcatcca | ccaaagcacc | atcaaaccag | gaacaacctg | 480 |
| aattccatat | ccaacccata | caaatgattc | ctggtctagc | ccctgttcct | gagaaactgg | 540 |
| tccccataag | acaacaggga | gtgaagattt | ctgaaaaccc | tagcattgca | acaagtccta | 600 |
| gggaattgac | acgggagatg | gataagaaga | tccgcagtat | tgtgagtagt | attctgaaaa | 660 |
| atgcttctgt | ccctgatgct | gataaagatg | ttccaacatc | ttccacccca | aatgctgaag | 720 |
| tcctctcttc | atccagtaaa | gaggaatcaa | cagaggaaga | ggaacaagcc | acagaggaga | 780 |
| cccctgcacc | aagggcacca | gaacctgctc | caggtgacct | cattgaccta | agaagtag | 840 |
| aatctgatga | ggaacccatt | gccaacaagt | tggcacctgg | cattgcagaa | agattacaaa | 900 |
| gcagaaaggg | aaaaaccccc | attactaggt | ctggacgaat | caaaactatg | cacagaaga | 960 |
| agagcacacc | aatcactcct | accacatcca | gatggagcaa | agttgcaatc | ccttccaaga | 1020 |
| agaggaaaga | attttcctca | tctgattctg | atgatgatgt | cgaactagat | gttcccgaca | 1080 |
| tcaagagggc | caagaaatct | gggaaaaagg | tgcctggaaa | tgtccctgat | gcaccattgg | 1140 |
| acaacatttc | attccactcc | attggcaatg | ttgaaaggtg | gaaatttgta | tatcaacgca | 1200 |
| gacttgcctt | agaaagagaa | ctgggaagag | atgccttgga | ttgcaaggag | atcatggacc | 1260 |
| tcatcaaggg | ctgctggact | gctgaaaaca | gtcaccaagt | tgggagatgt | tatgaaagcc | 1320 |
| tagtcaggga | attcattgtc | aacattccct | ctgacataac | aaacagaaag | agtgatgagt | 1380 |
| atcagaaagt | gtttgtcaga | ggaaaatgtg | ttagattctc | ccctgctgta | atcaacaaat | 1440 |
| acctgggcag | acctactgaa | ggagtggtgg | atattgctgt | ttctgagcat | caaattgcca | 1500 |
| aggaaatcac | tgccaaacaa | gtccagcatt | ggccaaagaa | agggaagctt | tctgcaggga | 1560 |
| agctaagtgt | gaagtatgca | atcctgcaca | ggattggcgc | tgcaaactgg | gtacccacca | 1620 |
| atcatacttc | cacagttgcc | acaggtttgg | gtaaatttct | gtatgctgtt | ggaaccaagt | 1680 |
| ccaaatttaa | ttttggaaag | tatatttttg | atcaaactgt | taagcattca | gaatcatttg | 1740 |
| ctgtcaaatt | acccattgcc | ttcccaactg | tattgtgtgg | cattatgttg | agtcaacatc | 1800 |
| ccaatatttt | aaacaacatt | gactctgtga | tgaagaaaga | atcggctctg | tccctgcatt | 1860 |
| acaaactgtt | tgaggggaca | catgtcccag | acattgtctc | gacatcaggg | aaagctgctg | 1920 |
| cttcaggtgc | tgtatccaag | ggatgctttg | attgctgaac | tcaaggacac | atgcaaggtg | 1980 |
| ctggaagcaa | ccatcaaagc | caccacagag | aagaaaatgg | agctggaacg | cctgatcaaa | 2040 |
| agactctcag | acagtggcat | tgatgatggt | gaagcagctg | aggaagaaga | agaagccgct | 2100 |

-continued

```
gaggaagaga aagatgcagc agaagataca gaatcagatg atgatgattc tgatgccacc    2160
ccatgaccat cagaccttta tttttgcttt ttactcttac tagctatagg gcatgtccct    2220
ttgaacaatt gattgctatt ggtctgtaat atttgcatgc attctacttt tgtcaaattc    2280
tgtctaaaaa ggggatatat attatgcatg attttgagta gtagatacta tgttgcaata    2340
gtatattatg cataatttat gattttgagt agtaggatac gatgtatgca tgattcatga    2400
ttttgagggg gagttgtaag tatatgattt tgagggggag tagtatctga tgatgctgat    2460
agaagatggc atggagacag ggggagcaga aagctgatgt cacgtgagat gtcttgacat    2520
cctggaaacg acttgcaact tgcagaattt tgctgtcgcc cctacagata ccgctgtgct    2580
tgattactct gataatgaaa gttgctgatc ccacttgcat aactgctcgt acctgctcag    2640
gaagtgtcta agtatgtttt agacaaaatt tgccaaaggg ggagattgtt agtgcttagc    2700
tttactgagt tttaaaagat tggctaaaat tttgttaaaa cataagcact tagacaatga    2760
aggaaagctg gagttgctgc acaggatgtc caacgttatg tcaaggaatc agattgggct    2820
ccacaatgca caaggcaaga taaaaggtca aatgaagaat tgaagctgca ggatccacga    2880
tgtcggatac aatgtccagg acatcctgcc cgaaaatact ggacacataa atctgttata    2940
tctttaacag attaatgtgc agttagcaac agatttggcg atctatcttt aggaacgaat    3000
taaaagataa ttaaagttcg aattacaaac ttgaatagtt cgttcaggga ttaaagatta    3060
aagataaaaa ctaaagatc aaactgtatc ttttagatct ttaagtgcag atttttcagg    3120
agaatgatag atcttatcca gcgcaagatg ttgcagccca gatacgcaca ctgctatata    3180
aacatgaagg ctgcacgagt tttctaccaa gtccgggatt gaagagttat tttgtgagtt    3240
ttgggacttg agtgttttgt gagccacctt gatgttaccc taacatcaag tgttggacct    3300
gagtgtgtag agttgatctc tattgttcag agagcaatct ctggtgtgtc tttgatttat    3360
ttgtaaacac gggagagtga ttgagaggga gtgagagggg ttctcatatc taagagtggc    3420
tcttaggtag aggttgcacg ggtagtggtt aggtgagaag gttgtaaaca gtggctgtta    3480
gatcttcgaa ctaacactat tttagtggat ttcctccctg gcttggtagc ccccagatgt    3540
aggtgaggtt gcaccgaact gggttaacaa ttctcttgtg ttatttactt gtttaatctg    3600
ttcatactgt caaatataat ctgcatgttc tgaagcgtga tgtcgtgaca tccggtacga    3660
catctgtcat tggtatcaga atttcatgct gcaaatattt acaatagacc tcctcaacct    3720
caacagcaaa atcaaccaca gcagaacaat tatgacctct ccagcaacag atacaaccct    3780
ggatggagga atcaccctaa cctcagatgg tccagccctc agcaacaaca acagcagcct    3840
gctccttcct tccaaaatgc tgttggccca agcagaccat acattcctcc accaatccaa    3900
caacagcaac aaccccagaa acagccaaca gttgaggccc tccacaactt ccttcgaaga    3960
acttgtgagg caaatgacta tgcagaacat gcagtttcag caagagacta gagcctccat    4020
tcagagctta accaatcaga tgggacaatt ggctacccaa ttgaatcaac aacagtccca    4080
gaattctgac aagttgcctt ctcaagctgt ccaaaatccc aaaaatgtca gtgccatttc    4140
attgaggtcg ggaaagcagt gtcaaggacc tcaacccgta gcaccttcct catctgcaaa    4200
tgaacctgcc aaacttcact ctac                                          4224
```

<210> SEQ ID NO 9
<211> LENGTH: 62
<212> TYPE: PRT
<213> ORGANISM: Glycine max
<220> FEATURE:
<221> NAME/KEY: misc_feature

```
<223> OTHER INFORMATION: ORF1

<400> SEQUENCE: 9

Ser Arg Pro Arg Ala Leu Ile Arg Leu Thr Ile Gly Arg Arg Leu Asp
1               5                   10                  15

Leu Val Asp Asp Lys Val Ile Thr Leu Glu His Val Asp Thr Glu Glu
            20                  25                  30

Gln Ile Ala Asp Ile Phe Thr Lys Ala Leu Asp Ala Asn Gln Phe Glu
        35                  40                  45

Lys Leu Arg Gly Lys Leu Gly Ile Cys Leu Leu Glu Asp Leu
    50                  55                  60

<210> SEQ ID NO 10
<211> LENGTH: 579
<212> TYPE: PRT
<213> ORGANISM: Glycine max

<400> SEQUENCE: 10

Thr Leu Ile Ala Arg Ser Leu Leu Gly Gln Asn Lys Phe Asp Arg Cys
1               5                   10                  15

Phe Thr Arg Pro Ser Thr Phe Leu Ile Gln Thr His Ile Phe Val Val
            20                  25                  30

Ile Ser Phe Ser Ala Phe Pro Asn Ser Ser Gln Arg Phe Thr Lys Pro
        35                  40                  45

Phe Gln Arg Leu Cys Phe Ser Met Ala Thr Ser Pro Lys Asp Thr Ser
    50                  55                  60

Ser Pro Gly Ser Pro Ser Val Pro Ser Ser Pro Ser Ser Thr Lys Ala
65                  70                  75                  80

Pro Ser Asn Gln Glu Gln Pro Glu Phe His Ile Gln Pro Ile Gln Met
                85                  90                  95

Ile Pro Gly Leu Ala Pro Val Pro Glu Lys Leu Val Pro Ile Arg Gln
            100                 105                 110

Gln Gly Val Lys Ile Ser Glu Asn Pro Ser Ile Ala Thr Ser Pro Arg
        115                 120                 125

Glu Leu Thr Arg Glu Met Asp Lys Lys Ile Arg Ser Ile Val Ser Ser
    130                 135                 140

Ile Leu Lys Asn Ala Ser Val Pro Asp Ala Asp Lys Asp Val Pro Thr
145                 150                 155                 160

Ser Ser Thr Pro Asn Ala Glu Val Leu Ser Ser Ser Lys Glu Glu
                165                 170                 175

Ser Thr Glu Glu Glu Gln Ala Thr Glu Thr Pro Ala Pro Arg
                180                 185                 190

Ala Pro Glu Pro Ala Pro Gly Asp Leu Ile Asp Leu Glu Glu Val Glu
            195                 200                 205

Ser Asp Glu Glu Pro Ile Ala Asn Lys Leu Ala Pro Gly Ile Ala Glu
        210                 215                 220

Arg Leu Gln Ser Arg Lys Gly Lys Thr Pro Ile Thr Arg Ser Gly Arg
225                 230                 235                 240

Ile Lys Thr Met Ala Gln Lys Lys Ser Thr Pro Ile Thr Pro Thr Thr
                245                 250                 255

Ser Arg Trp Ser Lys Val Ala Ile Pro Ser Lys Arg Lys Glu Phe
            260                 265                 270

Ser Ser Ser Asp Ser Asp Asp Val Glu Leu Asp Val Pro Asp Ile
        275                 280                 285

Lys Arg Ala Lys Lys Ser Gly Lys Lys Val Pro Gly Asn Val Pro Asp
```

```
                    290                 295                 300
Ala Pro Leu Asp Asn Ile Ser Phe His Ser Ile Gly Asn Val Glu Arg
305                 310                 315                 320

Trp Lys Phe Val Tyr Gln Arg Arg Leu Ala Leu Glu Arg Glu Leu Gly
                325                 330                 335

Arg Asp Ala Leu Asp Cys Lys Glu Ile Met Asp Leu Ile Lys Gly Cys
            340                 345                 350

Trp Thr Ala Glu Asn Ser His Gln Val Gly Arg Cys Tyr Glu Ser Leu
        355                 360                 365

Val Arg Glu Phe Ile Val Asn Ile Pro Ser Asp Ile Thr Asn Arg Lys
    370                 375                 380

Ser Asp Glu Tyr Gln Lys Val Phe Val Arg Gly Lys Cys Val Arg Phe
385                 390                 395                 400

Ser Pro Ala Val Ile Asn Lys Tyr Leu Gly Arg Pro Thr Glu Gly Val
                405                 410                 415

Val Asp Ile Ala Val Ser Glu His Gln Ile Ala Lys Glu Ile Thr Ala
            420                 425                 430

Lys Gln Val Gln His Trp Pro Lys Lys Gly Lys Leu Ser Ala Gly Lys
        435                 440                 445

Leu Ser Val Lys Tyr Ala Ile Leu His Arg Ile Gly Ala Ala Asn Trp
    450                 455                 460

Val Pro Thr Asn His Thr Ser Thr Val Ala Thr Gly Leu Gly Lys Phe
465                 470                 475                 480

Leu Tyr Ala Val Gly Thr Lys Ser Lys Phe Asn Phe Gly Lys Tyr Ile
                485                 490                 495

Phe Asp Gln Thr Val Lys His Ser Glu Ser Phe Ala Val Lys Leu Pro
            500                 505                 510

Ile Ala Phe Pro Thr Val Leu Cys Gly Ile Met Leu Ser Gln His Pro
        515                 520                 525

Asn Ile Leu Asn Asn Ile Asp Ser Val Met Lys Lys Glu Ser Ala Leu
    530                 535                 540

Ser Leu His Tyr Lys Leu Phe Glu Gly Thr His Val Pro Asp Ile Val
545                 550                 555                 560

Ser Thr Ser Gly Lys Ala Ala Ser Gly Ala Val Ser Lys Gly Cys
                565                 570                 575

Phe Asp Cys

<210> SEQ ID NO 11
<211> LENGTH: 62
<212> TYPE: PRT
<213> ORGANISM: Glycine max

<400> SEQUENCE: 11

Ser Arg Pro Arg Ala Leu Ile Arg Leu Thr Ile Gly Arg Arg Leu Asp
1               5                   10                  15

Leu Val Asp Asp Lys Val Ile Thr Leu Glu His Val Asp Thr Glu Glu
            20                  25                  30

Gln Ile Ala Asp Ile Phe Thr Lys Ala Leu Asp Ala Asn Gln Phe Glu
        35                  40                  45

Lys Leu Arg Gly Lys Leu Gly Ile Cys Leu Leu Glu Asp Leu
    50                  55                  60

<210> SEQ ID NO 12
<211> LENGTH: 23
<212> TYPE: DNA
```

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
cccagtcacg acgttgtaaa acg                                             23

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
tcctttaagt tcagagatt                                                  19

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
agcggataac aatttcacac agg                                             23

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
gtaatggtca accagaccac agtt                                            24

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
gacgaattgg cacttgg                                                    17

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
tttgcactgc cttgggag                                                   18

<210> SEQ ID NO 18
<211> LENGTH: 17
<212> TYPE: DNA
<213> ORGANISM: Artificial Sequence
<220> FEATURE:
<223> OTHER INFORMATION: primer

<400> SEQUENCE: 18
ccaaggagca caactgc                                                    17

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gctgaacaga atggacagga                                                    20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
aaagatataa caagattta                                                     19

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cccgatctta ttccttgaca                                                    20

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
cttgccacag tagtgaca                                                      18

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
tcttcccaag ctgtagca                                                      18

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
tcctttaagt tcagagatt                                                     19

<210> SEQ ID NO 25
<211> LENGTH: 20
<212> TYPE: DNA
<213> ORGANISM: Artificial Sequence
<220> FEATURE:

<223> OTHER INFORMATION: primer

<400> SEQUENCE: 25
agcgcgttct ctactgggcc        20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ccaccaaagc accatcaaac        20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ggcacagaag aagagcacac        20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tgcaaggaga tcatggacct        20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
cacaggattg gcgctgcaaa        20

<210> SEQ ID NO 30
<211> LENGTH: 29
<212> TYPE: DNA
<213> ORGANISM: Artificial Sequence
<220> FEATURE:
<223> OTHER INFORMATION: primer

<400> SEQUENCE: 30
tccctggctt ggtagccccc agatgtagg        29

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
ggccctccac aacttccttc g        21

```
<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
cagatgagga aggtgctacg                                                   20

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
cccagttcgg tgcaacctca cctacatctg                                        30

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggtggctcac aaaacactca                                                   20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tgtgtccagt attttcgggc                                                   20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
tcatcagata ctactccccc                                                   20

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
cctaggactt gttgcaatgc ta                                                22

<210> SEQ ID NO 38
<211> LENGTH: 20
<212> TYPE: DNA
<213> ORGANISM: Artificial Sequence
<220> FEATURE:
<223> OTHER INFORMATION: primer
```

```
<400> SEQUENCE: 38
atgaggaatg tagagggacg                                                    20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ctcatgagtt ctctgcagcc                                                    20

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40
gacaatgttg cagatacagc taaaagtgc                                          29

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
ccagatggat gtgaagagcg                                                    20

<210> SEQ ID NO 42
<211> LENGTH: 19
<212> TYPE: DNA
<213> ORGANISM: Artificial Sequence
<220> FEATURE:
<223> OTHER INFORMATION: primer

<400> SEQUENCE: 42
tgggatggaa aatgccagc                                                     19

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
agaactgtgt gtccctatcc                                                    20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
cctcagtgtc aacatgctcc                                                    20

<210> SEQ ID NO 45
<211> LENGTH: 20
```

```
<212> TYPE: DNA
<213> ORGANISM: Artificial Sequence
<220> FEATURE:
<223> OTHER INFORMATION: primer

<400> SEQUENCE: 45
atcccatagt cactggtgcc                                                20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ctctgttagc ctttcatacc                                                20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
cttgatcttg tagtgactcc                                                20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
atacagtgtg gttggagtcc                                                20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gaagtcttag actcaactcc                                                20

<210> SEQ ID NO 50
<211> LENGTH: 2826
<212> TYPE: DNA
<213> ORGANISM: Glycine max
<220> FEATURE:
<221> NAME/KEY: misc_feature
<223> OTHER INFORMATION: SIRE-1 genomic clone

<400> SEQUENCE: 50
gatgaaggat tcaatgtaga cttcacagag tcagaatgct tgatgacaaa agagaagaga     60
gaagtcctaa tgaagggcgg cagatcaaag gacaactgtt acctgtggac acctcaagaa    120
accagttact cctccacatg tctattctcc aaagaagatg aagtcaaaat atggcatcaa    180
agatttggac atctgcactt aggaggcatg aagaaaatca ttgacaaagg tgctgttaga    240
ggcattccca atctgaaaat agaagaaggc agaatctgtg gtgaatgtca gattggaaag    300
caagtcaaga tgtccaacca gaagcttcaa catcagacca cttccagggt gctggaacta    360
```

-continued

```
cttcacatgg acttgatggg gcctatgcaa gttgaaagcc ttggaagaaa aaggtatgcc      420
tatgttgttg tggatgattt ctccagattt acctgggtca actttatcag agagaaatca      480
gacacctttg aagtattcaa ggagttgagt ctaagacttc aaagagaaaa agactgtgtc      540
atcaagagaa tcaggagtga ccatggcaga gagtttgaaa acagcaagtt tactgaattc      600
tgcacatctg aaggcatcac tcatgagttc tctgcagcca ttacaccaca acaaaatggc      660
atagttgaaa ggaaaaacag gaccttgcca gaagctgcta gggtcatgct tcatgccaaa      720
gaacttccct ataatctctg ggctgaagcc atgaacacag catgctacat ccacaacaga      780
gtcacactta agagggggac tccaaccaca ctgtatgaaa tctggaaagg gaggaagcca      840
actgtcaagc acttccacat ctgtggaagt ccatgttaca ttttggcaga tagagagcaa      900
aggagaaaga tggatcccaa gagtgatgca gggatattct gggatactc tacaaacagc      960 agagcatata gagtattcaa ttccagaacc agaactgtga tggaatccat caatgtggtt     1020
gttgatgatc taactccagc aagaaagaag gatgtcgaag aagatgtcag aacatcggga     1080
gacaatgttg cagatacagc taaaagtgca gaaaatgcag aaaactctga ttctgctaca     1140
gatgaaccaa acatcaatca acctgacaag agaccctcca ttagaatcca gaagatgcac     1200
cccaaggagc tgattatagg agatccaaac agaggagtca ctacaagatc aagggagatt     1260
gagattatct ccaattcatg ttttgtctcc aaaattgagc ccaagaatgt gaaagaggca     1320
ctgactgatg agttctggat caatgctatg caagaagaat tggagcaatt caaaaggaat     1380
gaagtttggg agctagttcc taggcccgag ggaactaatg tgattggcac caagtggatc     1440
ttcaagaaca aaaccaatga agaaggtgtt ataaccagaa acaaggccag acttgttgct     1500
caaggctaca ctcagattga aggtgtagac tttgatgaaa cttttgcccc tggtgctaaa     1560
cttgagtcca tcagactgtt acttggtgta gcttgcatcc tcaaattcaa gctgtaccag     1620
atggatgtga agagcgcatt tctgaatgga tacctgaatg aagaagccta tgtggagcag     1680
ccaaagggat tgtagatcc aactcatcca gatcatgtat acaggctcaa gaagctctgc     1740
tatggattga agcaagcttc aagagcttgg tatgaaaggc taacagagtt ccttactcag     1800
caagggtata ggaaggggg gattgacaag acccttttg ttaaacaaga tgctggaaaa     1860
ttgatgatag cacagatata tgttgatgac attgtgtttg gagggatgtt gaatgagatg     1920
cttcgacatt tgtccaaca gatgcaattt gaatttgaga tgagttttgt tggagagctg     1980
aattattttt tgggaatcca agtgaagcag atggaagaat ccatattcct ttcacaaagc     2040
aagtatgcaa agaacattgt caagaagttt gggatggaaa atgccagcca taaaagaaca     2100
cctgcaccta atcaattgaa gctgtcaaaa gatgaagctg gcaccagtgt tgatcaaagt     2160
ttgtacagaa gcatgattgg gagcttaata tatttaacag ctagcagacc tgacatcacc     2220
tatgcagtag gtggttgtgc aagatatcaa gccaatccta agataagtca cttgaatcaa     2280
gtaaagagaa ttttgaaata tgtaaatggc accagtgact atgggattat gtactgtcat     2340
tgttcagatt caatgctggt tgggtattgt gatgctgatt gggctggaag tgtagatgac     2400 agaaaagca cttttggtgg atgtttttat ttgggaacca attttatttc atggttcagc     2460
aagaagcaga actgtgtgtc cctatccact gcagaagcag agtatattgc agcaggaagc     2520
agctgttcac aactagtttg gatgaagcag atgctcaagg agtacaatgt cgaacaagat     2580
gtcatgacat tgtactgtga caacttgagt gctattaata tttctaaaaa tcctgttcaa     2640
cacagcagaa ccaagcacat tgacattaga catcactata ttagagatct tgttgatgat     2700
```

-continued

```
aaagttatca cactggagca tgttgacact gaggaacaaa tagcagatat tttcacaaag    2760
gcattggatg caaatcagtt tgaaaaactg aggggcaagc tgggcatttg tctgctagag    2820
gattta                                                              2826
```

<210> SEQ ID NO 51
<211> LENGTH: 942
<212> TYPE: PRT
<213> ORGANISM: Glycine max

<400> SEQUENCE: 51

```
Asp Glu Gly Phe Asn Val Asp Phe Thr Glu Ser Glu Cys Leu Met Thr
1               5                   10                  15

Lys Glu Lys Arg Glu Val Leu Met Lys Gly Gly Arg Ser Lys Asp Asn
            20                  25                  30

Cys Tyr Leu Trp Thr Pro Gln Glu Thr Ser Tyr Ser Ser Thr Cys Leu
        35                  40                  45

Phe Ser Lys Glu Asp Glu Val Lys Ile Trp His Gln Arg Phe Gly His
    50                  55                  60

Leu His Leu Gly Gly Met Lys Lys Ile Ile Asp Lys Gly Ala Val Arg
65                  70                  75                  80

Gly Ile Pro Asn Leu Lys Ile Glu Glu Gly Arg Ile Cys Gly Glu Cys
                85                  90                  95

Gln Ile Gly Lys Gln Val Lys Met Ser Asn Gln Lys Leu Gln His Gln
            100                 105                 110

Thr Thr Ser Arg Val Leu Glu Leu Leu His Met Asp Leu Met Gly Pro
        115                 120                 125

Met Gln Val Glu Ser Leu Gly Arg Lys Arg Tyr Ala Tyr Val Val Val
    130                 135                 140

Asp Asp Phe Ser Arg Phe Thr Trp Val Asn Phe Ile Arg Glu Lys Ser
145                 150                 155                 160

Asp Thr Phe Glu Val Phe Lys Glu Leu Ser Leu Arg Leu Gln Arg Glu
                165                 170                 175

Lys Asp Cys Val Ile Lys Arg Ile Arg Ser Asp His Gly Arg Glu Phe
            180                 185                 190

Glu Asn Ser Lys Phe Thr Glu Phe Cys Thr Ser Glu Gly Ile Thr His
        195                 200                 205

Glu Phe Ser Ala Ala Ile Thr Pro Gln Gln Asn Gly Ile Val Glu Arg
    210                 215                 220

Lys Asn Arg Thr Leu Pro Glu Ala Ala Arg Val Met Leu His Ala Lys
225                 230                 235                 240

Glu Leu Pro Tyr Asn Leu Trp Ala Glu Ala Met Asn Thr Ala Cys Tyr
                245                 250                 255

Ile His Asn Arg Val Thr Leu Arg Arg Gly Thr Pro Thr Thr Leu Tyr
            260                 265                 270

Glu Ile Trp Lys Gly Arg Lys Pro Thr Val Lys His Phe His Ile Cys
        275                 280                 285

Gly Ser Pro Cys Tyr Ile Leu Ala Asp Arg Glu Gln Arg Lys Met
    290                 295                 300

Asp Pro Lys Ser Asp Ala Gly Ile Phe Leu Gly Tyr Ser Thr Asn Ser
305                 310                 315                 320

Arg Ala Tyr Arg Val Phe Asn Ser Arg Thr Arg Thr Val Met Glu Ser
                325                 330                 335

Ile Asn Val Val Val Asp Asp Leu Thr Pro Ala Arg Lys Lys Asp Val
            340                 345                 350
```

-continued

```
Glu Glu Asp Val Arg Thr Ser Gly Asp Asn Val Ala Asp Thr Ala Lys
            355                 360                 365
Ser Ala Glu Asn Ala Glu Asn Ser Asp Ser Ala Thr Asp Glu Pro Asn
370                 375                 380
Ile Asn Gln Pro Asp Lys Arg Pro Ser Ile Arg Ile Gln Lys Met His
385                 390                 395                 400
Pro Lys Glu Leu Ile Ile Gly Asp Pro Asn Arg Gly Val Thr Thr Arg
                405                 410                 415
Ser Arg Glu Ile Glu Ile Ile Ser Asn Ser Cys Phe Val Ser Lys Ile
                420                 425                 430
Glu Pro Lys Asn Val Lys Glu Ala Leu Thr Asp Glu Phe Trp Ile Asn
            435                 440                 445
Ala Met Gln Glu Glu Leu Glu Gln Phe Lys Arg Asn Glu Val Trp Glu
450                 455                 460
Leu Val Pro Arg Pro Glu Gly Thr Asn Val Ile Gly Thr Lys Trp Ile
465                 470                 475                 480
Phe Lys Asn Lys Thr Asn Glu Glu Gly Val Ile Thr Arg Asn Lys Ala
                485                 490                 495
Arg Leu Val Ala Gln Gly Tyr Thr Gln Ile Glu Gly Val Asp Phe Asp
                500                 505                 510
Glu Thr Phe Ala Pro Gly Ala Lys Leu Glu Ser Ile Arg Leu Leu Leu
            515                 520                 525
Gly Val Ala Cys Ile Leu Lys Phe Lys Leu Tyr Gln Met Asp Val Lys
            530                 535                 540
Ser Ala Phe Leu Asn Gly Tyr Leu Asn Glu Glu Ala Tyr Val Glu Gln
545                 550                 555                 560
Pro Lys Gly Phe Val Asp Pro Thr His Pro Asp His Val Tyr Arg Leu
                565                 570                 575
Lys Lys Leu Cys Tyr Gly Leu Lys Gln Ala Ser Arg Ala Trp Tyr Glu
                580                 585                 590
Arg Leu Thr Glu Phe Leu Thr Gln Gln Gly Tyr Arg Lys Gly Gly Ile
            595                 600                 605
Asp Lys Thr Leu Phe Val Lys Gln Asp Ala Gly Lys Leu Met Ile Ala
            610                 615                 620
Gln Ile Tyr Val Asp Asp Ile Val Phe Gly Gly Met Leu Asn Glu Met
625                 630                 635                 640
Leu Arg His Phe Val Gln Gln Met Gln Phe Glu Phe Glu Met Ser Phe
                645                 650                 655
Val Gly Glu Leu Asn Tyr Phe Leu Gly Ile Gln Val Lys Gln Met Glu
                660                 665                 670
Glu Ser Ile Phe Leu Ser Gln Ser Lys Tyr Ala Lys Asn Ile Val Lys
            675                 680                 685
Lys Phe Gly Met Glu Asn Ala Ser His Lys Arg Thr Pro Ala Pro Asn
            690                 695                 700
Gln Leu Lys Leu Ser Lys Asp Glu Ala Gly Thr Ser Val Asp Gln Ser
705                 710                 715                 720
Leu Tyr Arg Ser Met Ile Gly Ser Leu Ile Tyr Leu Thr Ala Ser Arg
                725                 730                 735
Pro Asp Ile Thr Tyr Ala Val Gly Gly Cys Ala Arg Tyr Gln Ala Asn
                740                 745                 750
Pro Lys Ile Ser His Leu Asn Gln Val Lys Arg Ile Leu Lys Tyr Val
            755                 760                 765
```

```
Asn Gly Thr Ser Asp Tyr Gly Ile Met Tyr Cys His Cys Ser Asp Ser
            770                 775                 780

Met Leu Val Gly Tyr Cys Asp Ala Asp Trp Ala Gly Ser Val Asp Asp
785                 790                 795                 800

Arg Lys Ser Thr Phe Gly Gly Cys Phe Tyr Leu Gly Thr Asn Phe Ile
                805                 810                 815

Ser Trp Phe Ser Lys Lys Gln Asn Cys Val Ser Leu Ser Thr Ala Glu
            820                 825                 830

Ala Glu Tyr Ile Ala Ala Gly Ser Ser Cys Ser Gln Leu Val Trp Met
            835                 840                 845

Lys Gln Met Leu Lys Glu Tyr Asn Val Glu Gln Asp Val Met Thr Leu
            850                 855                 860

Tyr Cys Asp Asn Leu Ser Ala Ile Asn Ile Ser Lys Asn Pro Val Gln
865                 870                 875                 880

His Ser Arg Thr Lys His Ile Asp Ile Arg His His Tyr Ile Arg Asp
                885                 890                 895

Leu Val Asp Asp Lys Val Ile Thr Leu Glu His Val Asp Thr Glu Glu
            900                 905                 910

Gln Ile Ala Asp Ile Phe Thr Lys Ala Leu Asp Ala Asn Gln Phe Glu
            915                 920                 925

Lys Leu Arg Gly Lys Leu Gly Ile Cys Leu Leu Glu Asp Leu
            930                 935                 940

<210> SEQ ID NO 52
<211> LENGTH: 400
<212> TYPE: PRT
<213> ORGANISM: Glycine max

<400> SEQUENCE: 52

Asp Glu Gly Phe Asn Val Asp Phe Thr Glu Ser Glu Cys Leu Met Thr
1               5                   10                  15

Lys Glu Lys Arg Glu Val Leu Met Lys Gly Gly Arg Ser Lys Asp Asn
            20                  25                  30

Cys Tyr Leu Trp Thr Pro Gln Glu Thr Ser Tyr Ser Ser Thr Cys Leu
        35                  40                  45

Phe Ser Lys Glu Asp Glu Val Lys Ile Trp His Gln Arg Phe Gly His
50                  55                  60

Leu His Leu Gly Gly Met Lys Lys Ile Ile Asp Lys Gly Ala Val Arg
65              70                  75                  80

Gly Ile Pro Asn Leu Lys Ile Glu Glu Gly Arg Ile Cys Gly Glu Cys
                85                  90                  95

Gln Ile Gly Lys Gln Val Lys Met Ser Asn Gln Lys Leu Gln His Gln
            100                 105                 110

Thr Thr Ser Arg Val Leu Glu Leu Leu His Met Asp Leu Met Gly Pro
        115                 120                 125

Met Gln Val Glu Ser Leu Gly Arg Lys Arg Tyr Ala Tyr Val Val Val
130                 135                 140

Asp Asp Phe Ser Arg Phe Thr Trp Val Asn Phe Ile Arg Glu Lys Ser
145                 150                 155                 160

Asp Thr Phe Glu Val Phe Lys Glu Leu Ser Leu Arg Leu Gln Arg Glu
                165                 170                 175

Lys Asp Cys Val Ile Lys Arg Ile Arg Ser Asp His Gly Arg Glu Phe
            180                 185                 190

Glu Asn Ser Lys Phe Thr Glu Phe Cys Thr Ser Glu Gly Ile Thr His
        195                 200                 205
```

```
Glu Phe Ser Ala Ala Ile Thr Pro Gln Gln Asn Gly Ile Val Glu Arg
    210                 215                 220

Lys Asn Arg Thr Leu Pro Glu Ala Ala Arg Val Met Leu His Ala Lys
225                 230                 235                 240

Glu Leu Pro Tyr Asn Leu Trp Ala Glu Ala Met Asn Thr Ala Cys Tyr
                245                 250                 255

Ile His Asn Arg Val Thr Leu Arg Arg Gly Thr Pro Thr Thr Leu Tyr
                260                 265                 270

Glu Ile Trp Lys Gly Arg Lys Pro Thr Val Lys His Phe His Ile Cys
            275                 280                 285

Gly Ser Pro Cys Tyr Ile Leu Ala Asp Arg Glu Gln Arg Arg Lys Met
    290                 295                 300

Asp Pro Lys Ser Asp Ala Gly Ile Phe Leu Gly Tyr Ser Thr Asn Ser
305                 310                 315                 320

Arg Ala Tyr Arg Val Phe Asn Ser Arg Thr Arg Thr Val Met Glu Ser
                325                 330                 335

Ile Asn Val Val Val Asp Asp Leu Thr Pro Ala Arg Lys Lys Asp Val
                340                 345                 350

Glu Glu Asp Val Arg Thr Ser Gly Asp Asn Val Ala Asp Thr Ala Lys
            355                 360                 365

Ser Ala Glu Asn Ala Glu Asn Ser Asp Ser Ala Thr Asp Glu Pro Asn
    370                 375                 380

Ile Asn Gln Pro Asp Lys Arg Pro Ser Ile Arg Ile Gln Lys Met His
385                 390                 395                 400

<210> SEQ ID NO 53
<211> LENGTH: 381
<212> TYPE: PRT
<213> ORGANISM: Glycine max

<400> SEQUENCE: 53

Pro Lys Glu Leu Ile Ile Gly Asp Pro Asn Arg Gly Val Thr Thr Arg
1               5                   10                  15

Ser Arg Glu Ile Glu Ile Ile Ser Asn Ser Cys Phe Val Ser Lys Ile
                20                  25                  30

Glu Pro Lys Asn Val Lys Glu Ala Leu Thr Asp Glu Phe Trp Ile Asn
            35                  40                  45

Ala Met Gln Glu Glu Leu Glu Gln Phe Lys Arg Asn Glu Val Trp Glu
    50                  55                  60

Leu Val Pro Arg Pro Glu Gly Thr Asn Val Ile Gly Thr Lys Trp Ile
65                  70                  75                  80

Phe Lys Asn Lys Thr Asn Glu Glu Gly Val Ile Thr Arg Asn Lys Ala
                85                  90                  95

Arg Leu Val Ala Gln Gly Tyr Thr Gln Ile Glu Gly Val Asp Phe Asp
            100                 105                 110

Glu Thr Phe Ala Pro Gly Ala Lys Leu Glu Ser Ile Arg Leu Leu Leu
    115                 120                 125

Gly Val Ala Cys Ile Leu Lys Phe Lys Leu Tyr Gln Met Asp Val Lys
130                 135                 140

Ser Ala Phe Leu Asn Gly Tyr Leu Asn Glu Glu Ala Tyr Val Glu Gln
145                 150                 155                 160

Pro Lys Gly Phe Val Asp Pro Thr His Pro Asp His Val Tyr Arg Leu
                165                 170                 175

Lys Lys Leu Cys Tyr Gly Leu Lys Gln Ala Ser Arg Ala Trp Tyr Glu
```

-continued

```
              180                 185                 190
Arg Leu Thr Glu Phe Leu Thr Gln Gln Gly Tyr Arg Lys Gly Gly Ile
              195                 200                 205
Asp Lys Thr Leu Phe Val Lys Gln Asp Ala Gly Lys Leu Met Ile Ala
        210                 215                 220
Gln Ile Tyr Val Asp Asp Ile Val Phe Gly Met Leu Asn Glu Met
225                 230                 235                 240
Leu Arg His Phe Val Gln Gln Met Gln Phe Glu Phe Glu Met Ser Phe
                245                 250                 255
Val Gly Glu Leu Asn Tyr Phe Leu Gly Ile Gln Val Lys Gln Met Glu
            260                 265                 270
Glu Ser Ile Phe Leu Ser Gln Ser Lys Tyr Ala Lys Asn Ile Val Lys
        275                 280                 285
Lys Phe Gly Met Glu Asn Ala Ser His Lys Arg Thr Pro Ala Pro Asn
    290                 295                 300
Gln Leu Lys Leu Ser Lys Asp Glu Ala Gly Thr Ser Val Asp Gln Ser
305                 310                 315                 320
Leu Tyr Arg Ser Met Ile Gly Ser Leu Ile Tyr Leu Thr Ala Ser Arg
                325                 330                 335
Pro Asp Ile Thr Tyr Ala Val Gly Gly Cys Ala Arg Tyr Gln Ala Asn
            340                 345                 350
Pro Lys Ile Ser His Leu Asn Gln Val Lys Arg Ile Leu Lys Tyr Val
        355                 360                 365
Asn Gly Thr Ser Asp Tyr Gly Ile Met Tyr Cys His Cys
    370                 375                 380

<210> SEQ ID NO 54
<211> LENGTH: 166
<212> TYPE: PRT
<213> ORGANISM: Glycine max
<220> FEATURE:
<221> NAME/KEY: SITE
<222> LOCATION: (162)..(162)
<223> OTHER INFORMATION: X= any amino acid
<220> FEATURE:
<221> NAME/KEY: SITE
<222> LOCATION: (165)..(165)
<223> OTHER INFORMATION: X= any amino acid

<400> SEQUENCE: 54

Ser Asp Ser Met Leu Val Gly Tyr Cys Asp Ala Asp Trp Ala Gly Ser
1               5                   10                  15
Val Asp Asp Arg Lys Ser Thr Phe Gly Gly Cys Phe Tyr Leu Gly Thr
            20                  25                  30
Asn Phe Ile Ser Trp Phe Ser Lys Lys Gln Asn Cys Val Ser Leu Ser
        35                  40                  45
Thr Ala Glu Ala Glu Tyr Ile Ala Ala Gly Ser Ser Cys Ser Gln Leu
    50                  55                  60
Val Trp Met Lys Gln Met Leu Lys Glu Tyr Asn Val Glu Gln Asp Val
65                  70                  75                  80
Met Thr Leu Tyr Cys Asp Asn Leu Ser Ala Ile Asn Ile Ser Lys Asn
                85                  90                  95
Pro Val Gln His Ser Arg Thr Lys His Ile Asp Ile Arg His His Tyr
            100                 105                 110
Ile Arg Asp Leu Val Asp Lys Val Ile Thr Leu Glu His Val Asp
        115                 120                 125
Thr Glu Glu Gln Ile Ala Asp Ile Phe Thr Lys Ala Leu Asp Ala Asn
```

```
            130                 135                 140
Gln Phe Glu Lys Leu Arg Gly Lys Leu Gly Ile Cys Leu Leu Glu Asp
145                 150                 155                 160

Leu Xaa Asn Pro Xaa Pro
                165

<210> SEQ ID NO 55
<211> LENGTH: 613
<212> TYPE: PRT
<213> ORGANISM: Glycine max

<400> SEQUENCE: 55

Thr Leu Ile Ala Arg Ser Leu Leu Gly Gln Asn Lys Phe Asp Arg Cys
1               5                   10                  15

Phe Thr Arg Pro Ser Thr Phe Leu Ile Gln Thr His Ile Phe Val Val
                20                  25                  30

Ile Ser Phe Ser Ala Phe Pro Asn Ser Ser Gln Arg Phe Thr Lys Pro
            35                  40                  45

Phe Gln Arg Leu Cys Phe Ser Met Ala Thr Ser Pro Lys Asp Thr Ser
        50                  55                  60

Ser Pro Gly Ser Pro Ser Val Pro Ser Ser Pro Ser Ser Thr Lys Ala
65                  70                  75                  80

Pro Ser Asn Gln Glu Gln Pro Glu Phe His Ile Gln Pro Ile Gln Met
                85                  90                  95

Ile Pro Gly Leu Ala Pro Val Pro Glu Lys Leu Val Pro Ile Arg Gln
            100                 105                 110

Gln Gly Val Lys Ile Ser Glu Asn Pro Ser Ile Ala Thr Ser Pro Arg
        115                 120                 125

Glu Leu Thr Arg Glu Met Asp Lys Lys Ile Arg Ser Ile Val Ser Ser
130                 135                 140

Ile Leu Lys Asn Ala Ser Val Pro Asp Ala Asp Lys Asp Val Pro Thr
145                 150                 155                 160

Ser Ser Thr Pro Asn Ala Glu Val Leu Ser Ser Ser Lys Glu Glu
                165                 170                 175

Ser Thr Glu Glu Glu Gln Ala Thr Glu Thr Pro Ala Pro Arg
            180                 185                 190

Ala Pro Glu Pro Ala Pro Gly Asp Leu Ile Asp Leu Glu Glu Val Glu
        195                 200                 205

Ser Asp Glu Glu Pro Ile Ala Asn Lys Leu Ala Pro Gly Ile Ala Glu
    210                 215                 220

Arg Leu Gln Ser Arg Lys Gly Lys Thr Pro Ile Thr Arg Ser Gly Arg
225                 230                 235                 240

Ile Lys Thr Met Ala Gln Lys Lys Ser Thr Pro Ile Thr Pro Thr Thr
                245                 250                 255

Ser Arg Trp Ser Lys Val Ala Ile Pro Ser Lys Lys Arg Lys Glu Phe
            260                 265                 270

Ser Ser Ser Asp Ser Asp Asp Val Glu Leu Asp Val Pro Asp Ile
        275                 280                 285

Lys Arg Ala Lys Lys Ser Gly Lys Lys Val Pro Gly Asn Val Pro Asp
    290                 295                 300

Ala Pro Leu Asp Asn Ile Ser Phe His Ser Ile Gly Asn Val Glu Arg
305                 310                 315                 320

Trp Lys Phe Val Tyr Gln Arg Arg Leu Ala Leu Glu Arg Glu Leu Gly
                325                 330                 335
```

```
Arg Asp Ala Leu Asp Cys Lys Glu Ile Met Asp Leu Ile Lys Gly Cys
            340                 345                 350

Trp Thr Ala Glu Asn Ser His Gln Val Gly Arg Cys Tyr Glu Ser Leu
        355                 360                 365

Val Arg Glu Phe Ile Val Asn Ile Pro Ser Asp Ile Thr Asn Arg Lys
    370                 375                 380

Ser Asp Glu Tyr Gln Lys Val Phe Val Arg Gly Lys Cys Val Arg Phe
385                 390                 395                 400

Ser Pro Ala Val Ile Asn Lys Tyr Leu Gly Arg Pro Thr Glu Gly Val
                405                 410                 415

Val Asp Ile Ala Val Ser Glu His Gln Ile Ala Lys Glu Ile Thr Ala
            420                 425                 430

Lys Gln Val Gln His Trp Pro Lys Lys Gly Lys Leu Ser Ala Gly Lys
        435                 440                 445

Leu Ser Val Lys Tyr Ala Ile Leu His Arg Ile Gly Ala Ala Asn Trp
    450                 455                 460

Val Pro Thr Asn His Thr Ser Thr Val Ala Thr Gly Leu Gly Lys Phe
465                 470                 475                 480

Leu Tyr Ala Val Gly Thr Lys Ser Lys Phe Asn Phe Gly Lys Tyr Ile
                485                 490                 495

Phe Asp Gln Thr Val Lys His Ser Glu Ser Phe Ala Val Lys Leu Pro
            500                 505                 510

Ile Ala Phe Pro Thr Val Leu Cys Gly Ile Met Leu Ser Gln His Pro
        515                 520                 525

Asn Ile Leu Asn Asn Ile Asp Ser Val Met Lys Lys Glu Ser Ala Leu
    530                 535                 540

Ser Leu His Tyr Lys Leu Phe Glu Gly Thr His Val Pro Asp Ile Val
545                 550                 555                 560

Ser Thr Ser Gly Lys Ala Ala Ser Gly Ala Val Ser Lys Gly Cys
                565                 570                 575

Phe Asp Cys Thr Gln Gly His Met Gln Gly Ala Gly Ser Asn His Gln
            580                 585                 590

Ser His His Arg Lys Lys Asn Gly Ala Gly Thr Pro Asp Gln Lys Thr
        595                 600                 605

Leu Arg Gln Trp His
    610

<210> SEQ ID NO 56
<211> LENGTH: 183
<212> TYPE: DNA
<213> ORGANISM: Glycine max

<400> SEQUENCE: 56
gttgctgcac aatgcacaag gcaagataaa agaagtgaag ctgcaggatc cacgatgtcg      60
gatacgatgt ccaagacatc tggcccgaaa atactggaca cataaatctg ttatatcttt    120
aacagattat tgtgcagtta gcaacaggtt agacgatcta tctttaggaa cgaactcttc    180
tag                                                                   183

<210> SEQ ID NO 57
<211> LENGTH: 138
<212> TYPE: DNA
<213> ORGANISM: Glycine max

<400> SEQUENCE: 57
gacttcgtta tgtcaaggaa taagatcggg ctgcacaatg cacaaggcaa gataaaatgt     60
```

```
caaatgaaga attgaagctg caggatccat gatgtcggat acaatgtcca ggacatcctg      120
cccgaaaata ctggagtt                                                    138
```

<210> SEQ ID NO 58
<211> LENGTH: 220
<212> TYPE: DNA
<213> ORGANISM: Glycine max

<400> SEQUENCE: 58

```
tccaacgtta tgtcaaggaa tcagattggg ctccacaatg cacaaggcaa gataaaaggt       60
caaatgaaga attgaagctg caggatccac gatgtcggat acaatgtcca ggacatcctg      120
cccgaaaata ctggacacat aaatctgtta tatctttaac agattaatgt gcagttagca      180
acagatttgg cgatctatct ttaggaacga attaaaagat                            220
```

<210> SEQ ID NO 59
<211> LENGTH: 579
<212> TYPE: PRT
<213> ORGANISM: Glycine max

<400> SEQUENCE: 59

```
Thr Leu Ile Ala Arg Ser Leu Leu Gly Gln Asn Lys Phe Asp Arg Cys
1               5                   10                  15

Phe Thr Arg Pro Ser Thr Phe Leu Ile Gln Thr His Ile Phe Val Val
                20                  25                  30

Ile Ser Phe Ser Ala Phe Pro Asn Ser Ser Gln Arg Phe Thr Lys Pro
            35                  40                  45

Phe Gln Arg Leu Cys Phe Ser Met Ala Thr Ser Pro Lys Asp Thr Ser
        50                  55                  60

Ser Pro Gly Ser Pro Ser Val Pro Ser Ser Ser Thr Lys Ala
65                  70                  75                  80

Pro Ser Asn Gln Glu Gln Pro Glu Phe His Ile Gln Pro Ile Gln Met
                85                  90                  95

Ile Pro Gly Leu Ala Pro Val Pro Glu Lys Leu Val Pro Ile Arg Gln
            100                 105                 110

Gln Gly Val Lys Ile Ser Glu Asn Pro Ser Ile Ala Thr Ser Pro Arg
        115                 120                 125

Glu Leu Thr Arg Glu Met Asp Lys Lys Ile Arg Ser Ile Val Ser Ser
    130                 135                 140

Ile Leu Lys Asn Ala Ser Val Pro Asp Ala Asp Lys Asp Val Pro Thr
145                 150                 155                 160

Ser Ser Thr Pro Asn Ala Glu Val Leu Ser Ser Ser Lys Glu Glu
                165                 170                 175

Ser Thr Glu Glu Glu Gln Ala Thr Glu Thr Pro Ala Pro Arg
            180                 185                 190

Ala Pro Glu Pro Ala Pro Gly Asp Leu Ile Asp Leu Glu Glu Val Glu
        195                 200                 205

Ser Asp Glu Glu Pro Ile Ala Asn Lys Leu Ala Pro Gly Ile Ala Glu
    210                 215                 220

Arg Leu Gln Ser Arg Lys Gly Lys Thr Pro Ile Thr Arg Ser Gly Arg
225                 230                 235                 240

Ile Lys Thr Met Ala Gln Lys Lys Ser Thr Pro Ile Thr Pro Thr Thr
                245                 250                 255

Ser Arg Trp Ser Lys Val Ala Ile Pro Ser Lys Lys Arg Lys Glu Phe
            260                 265                 270
```

```
Ser Ser Ser Asp Ser Asp Asp Val Glu Leu Asp Val Pro Asp Ile
            275                 280                 285
Lys Arg Ala Lys Lys Ser Gly Lys Lys Val Pro Gly Asn Val Pro Asp
290                 295                 300
Ala Pro Leu Asp Asn Ile Ser Phe His Ser Ile Gly Asn Val Glu Arg
305                 310                 315                 320
Trp Lys Phe Val Tyr Gln Arg Arg Leu Ala Leu Glu Arg Glu Leu Gly
                325                 330                 335
Arg Asp Ala Leu Asp Cys Lys Glu Ile Met Asp Leu Ile Lys Gly Cys
                340                 345                 350
Trp Thr Ala Glu Asn Ser His Gln Val Gly Arg Cys Tyr Glu Ser Leu
            355                 360                 365
Val Arg Glu Phe Ile Val Asn Ile Pro Ser Asp Ile Thr Asn Arg Lys
370                 375                 380
Ser Asp Glu Tyr Gln Lys Val Phe Val Arg Gly Lys Cys Val Arg Phe
385                 390                 395                 400
Ser Pro Ala Val Ile Asn Lys Tyr Leu Gly Arg Pro Thr Glu Gly Val
                405                 410                 415
Val Asp Ile Ala Val Ser Glu His Gln Ile Ala Lys Glu Ile Thr Ala
                420                 425                 430
Lys Gln Val Gln His Trp Pro Lys Gly Lys Leu Ser Ala Gly Lys
            435                 440                 445
Leu Ser Val Lys Tyr Ala Ile Leu His Arg Ile Gly Ala Ala Asn Trp
            450                 455                 460
Val Pro Thr Asn His Thr Ser Thr Val Ala Thr Gly Leu Gly Lys Phe
465                 470                 475                 480
Leu Tyr Ala Val Gly Thr Lys Ser Lys Phe Asn Phe Gly Lys Tyr Ile
                485                 490                 495
Phe Asp Gln Thr Val Lys His Ser Glu Ser Phe Ala Val Lys Leu Pro
                500                 505                 510
Ile Ala Phe Pro Thr Val Leu Cys Gly Ile Met Leu Ser Gln His Pro
            515                 520                 525
Asn Ile Leu Asn Asn Ile Asp Ser Val Met Lys Lys Glu Ser Ala Leu
530                 535                 540
Ser Leu His Tyr Lys Leu Phe Glu Gly Thr His Val Pro Asp Ile Val
545                 550                 555                 560
Ser Thr Ser Gly Lys Ala Ala Ser Gly Ala Val Ser Lys Gly Cys
                565                 570                 575
Phe Asp Cys

<210> SEQ ID NO 60
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: SITE
<222> LOCATION: (2)..(3)
<223> OTHER INFORMATION: X = any amino acid
<220> FEATURE:
<221> NAME/KEY: SITE
<222> LOCATION: (5)..(8)
<223> OTHER INFORMATION: X = any amino acid
<220> FEATURE:
<221> NAME/KEY: SITE
<222> LOCATION: (10)..(13)
<223> OTHER INFORMATION: X = any amino acid
```

<400> SEQUENCE: 60

Cys Xaa Xaa Cys Xaa Xaa Xaa Xaa His Xaa Xaa Xaa Xaa Cys
1               5                   10

<210> SEQ ID NO 61
<211> LENGTH: 14
<212> TYPE: PRT
<213> ORGANISM: Glycine max

<400> SEQUENCE: 61

Cys His Tyr Cys Gly Lys Tyr Gly His Ile Lys Pro Phe Cys
1               5                   10

<210> SEQ ID NO 62
<211> LENGTH: 14
<212> TYPE: PRT
<213> ORGANISM: Lilium henryi

<400> SEQUENCE: 62

Cys Tyr Ser Cys Gly Gln Pro Gly His Phe Lys Ala Asn Cys
1               5                   10

<210> SEQ ID NO 63
<211> LENGTH: 14
<212> TYPE: PRT
<213> ORGANISM: Drosophila melanogaster

<400> SEQUENCE: 63

Cys His His Cys Gly Arg Glu Gly His Ile Lys Lys Asp Cys
1               5                   10

<210> SEQ ID NO 64
<211> LENGTH: 14
<212> TYPE: PRT
<213> ORGANISM: Arabidopsis thaliana

<400> SEQUENCE: 64

Cys Trp Tyr Cys Lys Lys Glu Gly His Val Lys Lys Asp Cys
1               5                   10

<210> SEQ ID NO 65
<211> LENGTH: 14
<212> TYPE: PRT
<213> ORGANISM: Nicotiana tabacum

<400> SEQUENCE: 65

Cys Tyr Asn Cys Val Lys Pro Gly His Phe Lys Arg Asp Cys
1               5                   10

<210> SEQ ID NO 66
<211> LENGTH: 14
<212> TYPE: PRT
<213> ORGANISM: HIV-1

<400> SEQUENCE: 66

Cys Trp Lys Cys Gly Lys Pro Gly His Ile Met Thr Asn Cys
1               5                   10

<210> SEQ ID NO 67
<211> LENGTH: 14
<212> TYPE: PRT
<213> ORGANISM: Solanum tuberosum

<400> SEQUENCE: 67

Cys Asp His Cys Lys Lys Tyr Trp His Thr Arg Glu Thr Cys
1               5                   10

<210> SEQ ID NO 68
<211> LENGTH: 14
<212> TYPE: PRT
<213> ORGANISM: Cauliflower mosaic

<400> SEQUENCE: 68

Cys Trp Ile Cys Asn Ile Glu Gly His Tyr Ala Asn Glu Cys
1               5                   10

<210> SEQ ID NO 69
<211> LENGTH: 10
<212> TYPE: PRT
<213> ORGANISM: Arabidopsis thaliana

<400> SEQUENCE: 69

Leu Asp Ser Gly Cys Thr Ser His Met Ser
1               5                   10

<210> SEQ ID NO 70
<211> LENGTH: 10
<212> TYPE: PRT
<213> ORGANISM: Nicotiana tabacum

<400> SEQUENCE: 70

Val Asp Thr Ala Ala Ser His His Ala Thr
1               5                   10

<210> SEQ ID NO 71
<211> LENGTH: 10
<212> TYPE: PRT
<213> ORGANISM: Drosophila melanogaster

<400> SEQUENCE: 71

Leu Asp Ser Gly Ala Ser Asp His Leu Thr
1               5                   10

<210> SEQ ID NO 72
<211> LENGTH: 10
<212> TYPE: PRT
<213> ORGANISM: Solanum tuberosum

<400> SEQUENCE: 72

Ile Asp Ser Arg Ala Ser Asp His Met Thr
1               5                   10

<210> SEQ ID NO 73
<211> LENGTH: 10
<212> TYPE: PRT
<213> ORGANISM: Lilium henryi

<400> SEQUENCE: 73

Ile Asp Thr Gly Ser Thr His Ser Phe Ile
1               5                   10

<210> SEQ ID NO 74
<211> LENGTH: 10
<212> TYPE: PRT
<213> ORGANISM: Cauliflower mosaic

<400> SEQUENCE: 74

Val Asp Thr Gly Ala Ser Leu Cys Ile Ala

-continued

```
1               5                   10
```

<210> SEQ ID NO 75
<211> LENGTH: 10
<212> TYPE: PRT
<213> ORGANISM: HIV-1

<400> SEQUENCE: 75

```
Leu Asp Thr Gly Arg Asp Asp Thr Val Leu
1               5                   10
```

<210> SEQ ID NO 76
<211> LENGTH: 22
<212> TYPE: RNA
<213> ORGANISM: Glycine max
<220> FEATURE:
<221> NAME/KEY: misc_feature
<223> OTHER INFORMATION: 3'-end of soybean tRNA met-1 (sequence is
      identified in the 5' to 3' direction in the sequence listing
      and in the 3' to 5' direction in Figure 11)

<400> SEQUENCE: 76
ucgaaaccug gcucugauac ca                                         22

<210> SEQ ID NO 77
<211> LENGTH: 20
<212> TYPE: DNA
<213> ORGANISM: Solanum tuberosum

<400> SEQUENCE: 77
ttgcagtatc taaactttca                                            20

<210> SEQ ID NO 78
<211> LENGTH: 65
<212> TYPE: PRT
<213> ORGANISM: Drosophila melanogaster

<400> SEQUENCE: 78

```
His Lys Arg Ala Lys His Ile Asp Ile Lys Tyr His Phe Ala Arg Glu
1               5                   10                  15

Gln Val Gln Asn Asn Val Ile Cys Leu Glu Tyr Ile Pro Thr Glu Asn
            20                  25                  30

Gln Leu Ala Asp Ile Phe Thr Lys Pro Leu Pro Ala Ala Arg Phe Val
        35                  40                  45

Glu Leu Arg Asp Lys Leu Gly Leu Leu Gln Asp Gln Ser Asn Ala
    50                  55                  60

Glu
65
```

<210> SEQ ID NO 79
<211> LENGTH: 441
<212> TYPE: PRT
<213> ORGANISM: Zea mays
<220> FEATURE:
<221> NAME/KEY: SITE
<222> LOCATION: (1)..(441)
<223> OTHER INFORMATION: amino acid positions 86-526 of Opie-2
      retroelement

<400> SEQUENCE: 79

```
Asn Met Gly Tyr Asn Cys Leu Phe Thr Asn Ile Asp Val Ser Val Phe
1               5                   10                  15

Arg Arg Cys Asp Gly Ser Leu Ala Phe Lys Gly Val Leu Asp Gly Lys
            20                  25                  30
```

-continued

```
Leu Tyr Leu Val Asp Phe Ala Lys Glu Ala Gly Leu Asp Ala Cys
         35                  40                  45
Leu Ile Ala Lys Thr Ser Met Gly Trp Leu Trp His Arg Arg Leu Ala
 50                  55                  60
His Val Gly Met Lys Asn Leu His Lys Leu Leu Lys Gly Glu His Val
 65                  70                  75                  80
Ile Gly Leu Thr Asn Val Gln Phe Glu Lys Asp Arg Pro Cys Ala Ala
                 85                  90                  95
Cys Gln Ala Gly Lys Gln Val Gly Gly Ser His His Thr Lys Asn Val
                100                 105                 110
Met Thr Thr Ser Arg Pro Leu Glu Met Leu His Met Asp Leu Phe Gly
         115                 120                 125
Pro Val Ala Tyr Leu Ser Ile Gly Gly Ser Lys Tyr Gly Leu Val Ile
         130                 135                 140
Val Asp Asp Phe Ser Arg Phe Thr Trp Val Phe Phe Leu Gln Glu Lys
145                 150                 155                 160
Ser Glu Thr Gln Gly Thr Leu Lys Arg Phe Leu Arg Arg Ala Gln Asn
                 165                 170                 175
Glu Phe Glu Leu Lys Val Lys Lys Ile Arg Ser Asp Asn Gly Ser Glu
             180                 185                 190
Phe Lys Asn Leu Gln Val Glu Glu Phe Leu Glu Glu Glu Gly Ile Lys
         195                 200                 205
His Glu Phe Ser Ala Pro Tyr Thr Pro Gln Gln Asn Gly Val Val Glu
     210                 215                 220
Arg Lys Asn Arg Thr Leu Ile Asp Met Ala Arg Thr Met Leu Gly Glu
225                 230                 235                 240
Phe Lys Thr Pro Glu Cys Phe Trp Thr Glu Ala Val Asn Thr Ala Cys
                 245                 250                 255
His Ala Ile Asn Arg Val Tyr Leu His Arg Ile Leu Lys Asn Thr Ser
             260                 265                 270
Tyr Glu Leu Leu Thr Gly Asn Lys Pro Asn Val Ser Tyr Phe Arg Val
         275                 280                 285
Phe Gly Ser Lys Cys Tyr Ile Leu Val Lys Lys Gly Arg Asn Ser Lys
     290                 295                 300
Phe Ala Pro Lys Ala Val Glu Gly Phe Leu Leu Gly Tyr Asp Ser Asn
305                 310                 315                 320
Thr Lys Ala Tyr Arg Val Phe Asn Lys Ser Ser Gly Leu Val Glu Val
                 325                 330                 335
Ser Gly Asp Val Val Phe Asp Glu Thr Asn Gly Ser Pro Arg Glu Gln
             340                 345                 350
Val Val Asp Cys Asp Asp Val Asp Glu Glu Asp Ile Pro Thr Ala Ala
         355                 360                 365
Ile Arg Thr Met Ala Ile Gly Glu Val Arg Pro Gln Glu Gln Asp Glu
     370                 375                 380
Arg Glu Gln Pro Ser Pro Ser Thr Met Val His Pro Pro Thr Gln Asp
385                 390                 395                 400
Asp Glu Gln Val His Gln Gln Glu Val Cys Asp Gln Gly Gly Ala Gln
                 405                 410                 415
Asp Asp His Val Leu Glu Glu Glu Ala Gln Pro Ala Pro Pro Thr Gln
             420                 425                 430
Val Arg Ala Met Ile Gln Arg Asp His
         435                 440
```

<210> SEQ ID NO 80
<211> LENGTH: 380
<212> TYPE: PRT
<213> ORGANISM: Zea mays
<220> FEATURE:
<221> NAME/KEY: SITE
<222> LOCATION: (1)..(380)
<223> OTHER INFORMATION: amino acid positions 527-906 of Opie-2 retroelement

<400> SEQUENCE: 80

```
Pro Val Asp Gln Ile Leu Gly Asp Ile Ser Lys Gly Val Thr Thr Arg
1               5                   10                  15

Ser Arg Leu Val Asn Phe Cys Glu His Asn Ser Phe Val Ser Ser Ile
            20                  25                  30

Glu Pro Phe Arg Val Glu Glu Ala Leu Leu Asp Pro Asp Trp Val Leu
        35                  40                  45

Ala Met Gln Glu Glu Leu Asn Asn Phe Lys Arg Asn Glu Val Trp Thr
    50                  55                  60

Leu Val Pro Arg Pro Lys Gln Asn Val Val Gly Thr Lys Trp Val Phe
65                  70                  75                  80

Arg Asn Lys Gln Asp Glu Arg Gly Val Val Thr Arg Asn Lys Ala Arg
                85                  90                  95

Leu Val Ala Lys Gly Tyr Ala Gln Val Ala Gly Leu Asp Phe Glu Glu
            100                 105                 110

Thr Phe Ala Pro Val Ala Arg Leu Glu Ser Ile Arg Ile Leu Leu Ala
        115                 120                 125

Tyr Ala Ala His His Ser Phe Arg Leu Tyr Gln Met Asp Val Lys Ser
    130                 135                 140

Ala Phe Leu Asn Gly Pro Ile Lys Glu Glu Val Tyr Val Glu Gln Pro
145                 150                 155                 160

Pro Gly Phe Glu Asp Glu Arg Tyr Pro Asp His Val Cys Lys Leu Ser
                165                 170                 175

Lys Ala Leu Tyr Gly Leu Lys Gln Ala Pro Arg Ala Trp Tyr Glu Cys
            180                 185                 190

Leu Arg Asp Phe Leu Ile Ala Asn Ala Phe Lys Val Gly Lys Ala Asp
        195                 200                 205

Pro Thr Leu Phe Thr Lys Thr Cys Asp Gly Asp Leu Phe Val Cys Gln
    210                 215                 220

Ile Tyr Val Asp Asp Ile Ile Phe Gly Ser Thr Asn Gln Lys Ser Cys
225                 230                 235                 240

Glu Glu Phe Ser Arg Val Met Thr Gln Lys Phe Glu Met Ser Met Met
                245                 250                 255

Gly Glu Leu Asn Tyr Phe Leu Gly Phe Gln Val Lys Gln Leu Lys Asp
            260                 265                 270

Gly Thr Phe Ile Ser Gln Thr Lys Tyr Thr Gln Asp Leu Leu Lys Arg
        275                 280                 285

Phe Gly Met Lys Asp Ala Lys Pro Ala Lys Thr Pro Met Gly Thr Asp
    290                 295                 300

Gly His Thr Asp Leu Asn Lys Gly Gly Lys Ser Val Asp Gln Lys Ala
305                 310                 315                 320

Tyr Arg Ser Met Ile Gly Ser Leu Leu Tyr Leu Cys Ala Ser Arg Pro
                325                 330                 335

Asp Ile Met Leu Ser Val Cys Met Cys Ala Arg Phe Gln Ser Asp Pro
            340                 345                 350
```

```
Lys Glu Cys His Leu Val Ala Val Lys Arg Ile Leu Arg Tyr Leu Val
        355                 360                 365

Ala Thr Pro Cys Phe Gly Leu Trp Tyr Pro Lys Gly
    370                 375                 380

<210> SEQ ID NO 81
<211> LENGTH: 168
<212> TYPE: PRT
<213> ORGANISM: Zea mays
<220> FEATURE:
<221> NAME/KEY: SITE
<222> LOCATION: (1)..(168)
<223> OTHER INFORMATION: nucleotide positions 901-1068 of Opie-2
      nucleotide sequence

<400> SEQUENCE: 81

Leu Trp Tyr Pro Lys Gly Ser Thr Phe Asp Leu Val Gly Tyr Ser Asp
1               5                   10                  15

Ser Asp Tyr Ala Gly Cys Lys Val Asp Arg Lys Ser Thr Ser Gly Thr
            20                  25                  30

Cys Gln Phe Leu Gly Arg Ser Leu Val Ser Trp Asn Ser Lys Lys Gln
        35                  40                  45

Thr Ser Val Ala Leu Ser Thr Ala Glu Ala Glu Tyr Val Ala Ala Gly
    50                  55                  60

Gln Cys Cys Ala Gln Leu Leu Trp Met Arg Gln Thr Leu Arg Asp Phe
65                  70                  75                  80

Gly Tyr Asn Leu Ser Lys Val Pro Leu Leu Cys Asp Asn Glu Ser Ala
                85                  90                  95

Ile Arg Met Ala Glu Asn Pro Val Glu His Ser Arg Thr Lys His Ile
            100                 105                 110

Asp Ile Arg His His Phe Leu Arg Asp His Gln Gln Lys Gly Asp Ile
        115                 120                 125

Glu Val Phe His Val Ser Thr Glu Asn Gln Leu Ala Asp Ile Phe Thr
    130                 135                 140

Lys Pro Leu Asp Glu Lys Thr Phe Cys Arg Leu Arg Ser Glu Leu Asn
145                 150                 155                 160

Val Leu Asp Ser Arg Asn Leu Asp
                165

<210> SEQ ID NO 82
<211> LENGTH: 4
<212> TYPE: PRT
<213> ORGANISM: Artificial Sequence
<220> FEATURE:
<223> OTHER INFORMATION: synthetic

<400> SEQUENCE: 82

Lys Lys Gly Lys
1

<210> SEQ ID NO 83
<211> LENGTH: 647
<212> TYPE: PRT
<213> ORGANISM: Glycine max

<400> SEQUENCE: 83

Thr Leu Ile Ala Arg Ser Leu Leu Gly Gln Asn Lys Phe Asp Arg Cys
1               5                   10                  15

Phe Thr Arg Pro Ser Thr Phe Leu Ile Gln Thr His Ile Phe Val Val
            20                  25                  30
```

-continued

```
Ile Ser Phe Ser Ala Phe Pro Asn Ser Ser Gln Arg Phe Thr Lys Pro
         35                  40                  45

Phe Gln Arg Leu Cys Phe Ser Met Ala Thr Ser Pro Lys Asp Thr Ser
 50                  55                  60

Ser Pro Gly Ser Pro Ser Val Pro Ser Ser Pro Ser Ser Thr Lys Ala
 65                  70                  75                  80

Pro Ser Asn Gln Glu Gln Pro Glu Phe His Ile Gln Pro Ile Gln Met
                 85                  90                  95

Ile Pro Gly Gln Ala Pro Val Pro Glu Lys Leu Val Pro Lys Arg Gln
                100                 105                 110

Gln Gly Val Lys Ile Ser Glu Asn Pro Ser Ile Ala Thr Ser Pro Arg
            115                 120                 125

Val Asp Thr Glu Met Asp Lys Lys Ile Arg Ser Ile Val Ser Ser Ile
    130                 135                 140

Leu Lys Asn Ala Ser Val Pro Asp Ala Asp Lys Asp Val Pro Thr Ser
145                 150                 155                 160

Ser Thr Pro Asn Ala Glu Val Leu Ser Ser Ser Lys Glu Glu Ser
                165                 170                 175

Thr Glu Glu Glu Gln Ala Thr Glu Glu Thr Pro Ala Pro Arg Ala
                180                 185                 190

Pro Glu Pro Ala Pro Gly Asp Leu Ile Asp Leu Glu Glu Val Glu Ser
            195                 200                 205

Asp Glu Glu Pro Ile Ala Asn Lys Leu Ala Pro Gly Ile Ala Glu Arg
    210                 215                 220

Leu Gln Ser Arg Lys Gly Lys Thr Pro Ile Thr Arg Ser Gly Arg Ile
225                 230                 235                 240

Lys Thr Met Ala Gln Lys Lys Ser Thr Pro Ile Thr Pro Thr Thr Ser
                245                 250                 255

Arg Trp Ser Lys Val Ala Ile Pro Ser Lys Lys Arg Lys Glu Phe Ser
                260                 265                 270

Ser Ser Asp Ser Asp Asp Asp Val Glu Leu Asp Val Pro Asp Ile Lys
            275                 280                 285

Arg Ala Lys Lys Ser Gly Lys Lys Val Pro Gly Asn Val Pro Asp Ala
    290                 295                 300

Pro Leu Asp Asn Ile Ser Phe His Ser Ile Gly Asn Val Glu Arg Trp
305                 310                 315                 320

Lys Phe Val Tyr Gln Arg Arg Leu Ala Leu Glu Arg Glu Leu Gly Arg
                325                 330                 335

Asp Ala Leu Asp Cys Lys Glu Ile Met Asp Leu Ile Lys Ala Ala Gly
            340                 345                 350

Leu Leu Lys Thr Val Thr Lys Leu Gly Asp Cys Tyr Glu Ser Leu Val
    355                 360                 365

Arg Glu Phe Ile Val Asn Ile Pro Ser Asp Ile Thr Asn Arg Lys Ser
    370                 375                 380

Asp Glu Tyr Gln Lys Val Phe Arg Gly Lys Cys Val Arg Phe Ser
385                 390                 395                 400

Pro Ala Val Ile Asn Lys Tyr Leu Gly Arg Pro Thr Glu Gly Val Val
                405                 410                 415

Asp Ile Ala Val Ser Glu His Gln Ile Ala Lys Glu Ile Thr Ala Lys
            420                 425                 430

Gln Val Gln His Trp Pro Lys Lys Gly Lys Leu Ser Ala Gly Lys Leu
    435                 440                 445

Ser Val Lys Tyr Ala Ile Leu His Arg Ile Gly Ala Ala Asn Trp Val
```

-continued

```
            450                 455                 460
Pro Thr Asn His Thr Ser Thr Val Ala Thr Gly Leu Gly Lys Phe Leu
465                 470                 475                 480

Tyr Ala Val Gly Thr Lys Ser Lys Phe Asn Phe Gly Lys Tyr Ile Phe
                485                 490                 495

Asp Gln Thr Val Lys His Ser Glu Ser Phe Ala Val Lys Leu Pro Ile
                500                 505                 510

Ala Phe Pro Thr Val Leu Cys Gly Ile Met Leu Ser Gln His Pro Asn
            515                 520                 525

Ile Leu Asn Asn Ile Asp Ser Val Met Lys Arg Glu Ser Ala Leu Ser
        530                 535                 540

Leu His Tyr Lys Leu Phe Glu Gly Thr His Val Pro Asp Ile Val Ser
545                 550                 555                 560

Thr Ser Gly Lys Ala Ala Ser Gly Ala Val Ser Lys Asp Ala Leu
                565                 570                 575

Ile Ala Glu Leu Lys Asp Thr Cys Lys Val Leu Glu Ala Thr Ile Lys
            580                 585                 590

Ala Thr Thr Glu Lys Lys Met Glu Leu Glu Arg Leu Ile Lys Arg Leu
            595                 600                 605

Ser Asp Ser Gly Ile Asp Gly Glu Ala Ala Glu Glu Glu Glu
        610                 615                 620

Ala Ala Glu Glu Glu Lys Asp Ala Ala Glu Asp Thr Glu Ser Asp Asp
625                 630                 635                 640

Asp Asp Ser Asp Ala Thr Pro
                645
```

<210> SEQ ID NO 84
<211> LENGTH: 578
<212> TYPE: PRT
<213> ORGANISM: Glycine max

<400> SEQUENCE: 84

```
Thr Leu Ile Ala Arg Ser Leu Leu Gly Gln Asn Lys Phe Asp Arg Cys
1               5                   10                  15

Phe Thr Arg Pro Ser Thr Phe Leu Ile Gln Thr His Ile Phe Val Val
                20                  25                  30

Ile Ser Phe Ser Ala Phe Pro Asn Ser Ser Gln Arg Phe Thr Lys Pro
            35                  40                  45

Phe Gln Arg Leu Cys Phe Ser Met Ala Thr Ser Pro Lys Asp Thr Ser
        50                  55                  60

Ser Pro Gly Ser Pro Ser Val Pro Ser Ser Ser Thr Lys Ala
65                  70                  75                  80

Pro Ser Asn Gln Glu Gln Pro Glu Phe His Ile Gln Pro Ile Gln Met
                85                  90                  95

Ile Pro Gly Leu Ala Pro Val Pro Glu Lys Leu Val Pro Ile Arg Gln
            100                 105                 110

Gln Gly Val Lys Ile Ser Glu Asn Pro Ser Ile Ala Thr Ser Pro Arg
        115                 120                 125

Glu Leu Thr Arg Glu Met Asp Lys Lys Ile Arg Ser Ile Val Ser Ser
130                 135                 140

Ile Leu Lys Asn Ala Ser Val Pro Asp Ala Asp Lys Asp Val Pro Thr
145                 150                 155                 160

Ser Ser Thr Pro Asn Ala Glu Val Leu Ser Ser Ser Ser Lys Glu Glu
                165                 170                 175
```

```
Ser Thr Glu Glu Glu Gln Ala Thr Glu Thr Pro Ala Pro Arg
            180                 185                 190

Ala Pro Glu Pro Ala Pro Gly Asp Leu Ile Asp Leu Glu Val Glu
        195                 200                 205

Ser Asp Glu Glu Pro Ile Ala Asn Lys Leu Ala Pro Gly Ile Ala Glu
        210                 215                 220

Arg Leu Gln Ser Arg Lys Gly Lys Thr Pro Ile Thr Arg Ser Gly Arg
225                 230                 235                 240

Ile Lys Thr Met Ala Gln Lys Lys Ser Thr Pro Ile Thr Pro Thr Thr
                245                 250                 255

Ser Arg Trp Ser Lys Val Ala Ile Pro Ser Lys Lys Arg Lys Glu Phe
                260                 265                 270

Ser Ser Ser Asp Ser Asp Asp Val Glu Leu Asp Val Pro Asp Ile
        275                 280                 285

Lys Arg Ala Lys Lys Ser Gly Lys Lys Val Pro Gly Asn Val Pro Asp
    290                 295                 300

Ala Pro Leu Asp Asn Ile Ser Phe His Ser Ile Gly Asn Val Glu Arg
305                 310                 315                 320

Trp Lys Phe Val Tyr Gln Arg Arg Leu Ala Leu Glu Arg Glu Leu Gly
                325                 330                 335

Arg Asp Ala Leu Asp Cys Lys Glu Ile Met Asp Leu Ile Lys Gly Cys
                340                 345                 350

Trp Thr Ala Glu Asn Ser His Gln Val Gly Arg Cys Tyr Glu Ser Leu
                355                 360                 365

Val Arg Glu Phe Ile Val Asn Ile Pro Ser Asp Ile Thr Asn Arg Lys
    370                 375                 380

Ser Asp Glu Tyr Gln Lys Val Phe Val Arg Gly Lys Cys Val Arg Phe
385                 390                 395                 400

Ser Pro Ala Val Ile Asn Lys Tyr Leu Gly Arg Pro Thr Glu Gly Val
                405                 410                 415

Val Asp Ile Ala Val Ser Glu His Gln Ile Ala Lys Glu Ile Thr Ala
                420                 425                 430

Gln Val Gln His Trp Pro Lys Lys Gly Lys Leu Ser Ala Gly Lys Leu
        435                 440                 445

Ser Val Lys Tyr Ala Ile Leu His Arg Ile Gly Ala Ala Asn Trp Val
    450                 455                 460

Pro Thr Asn His Thr Ser Thr Val Ala Thr Gly Leu Gly Lys Phe Leu
465                 470                 475                 480

Tyr Ala Val Gly Thr Lys Ser Lys Phe Asn Phe Gly Lys Tyr Ile Phe
                485                 490                 495

Asp Gln Thr Val Lys His Ser Glu Ser Phe Ala Val Lys Leu Pro Ile
        500                 505                 510

Ala Phe Pro Pro Val Leu Cys Gly Ile Met Leu Thr Gln His Pro Asn
    515                 520                 525

Ile Leu Asn Asn Ile Asp Ser Val Met Lys Lys Glu Ser Ala Leu Ser
530                 535                 540

Leu His Tyr Lys Leu Phe Glu Gly Thr His Val Pro Asp Ile Val Ser
545                 550                 555                 560

Thr Ser Gly Lys Ala Ala Ala Ser Gly Ala Val Ser Lys Gly Cys Phe
                565                 570                 575

Asp Cys

<210> SEQ ID NO 85
```

-continued

```
<211> LENGTH: 8
<212> TYPE: PRT
<213> ORGANISM: Glycine max

<400> SEQUENCE: 85

Gln Leu Leu Leu Ser Glu Arg Ala
1               5

<210> SEQ ID NO 86
<211> LENGTH: 34
<212> TYPE: PRT
<213> ORGANISM: Glycine max

<400> SEQUENCE: 86

Thr Gln Gly His Met Gln Gly Ala Gly Ser Asn His Gln Ser His His
1               5                   10                  15

Arg Lys Lys Asn Gly Ala Gly Thr Pro Asp Gln Lys Thr Leu Arg Gln
                20                  25                  30

Trp His
```

I claim:

1. An isolated, purified polynucleotide comprising a polynucleotide selected from the group consisting of SEQ ID NO:3, SEQ ID NO:8, SEQ ID NO:50, polynucleotides that hybridize under stringent conditions to any one of the foregoing polynucleotides and that have the properties of the foregoing polynucleotides, and fragments thereof, wherein said fragments retain the properties of their respective parent polynucleotides.

2. The polynucleotide of claim 1 wherein said fragments comprise all or part of one or more SIRE-1 long terminal repeats.

3. The polynucleotide of claim 1 further comprising a heterologous DNA.

4. The polynucleotide of claim 3 wherein said heterologous DNA comprises a transcriptional regulatory element.

5. A vector comprising the polynucleotide according to claim 1.

6. The vector of claim 5 further comprising a heterologous DNA.

7. The vector of claim 6 wherein said heterologous DNA comprises a transcriptional regulatory element.

8. The vector of claim 6 wherein said heterologous DNA is operably linked to a transcriptional regulatory element.

9. The vector of claim 8 wherein the heterologous DNA comprises a DNA encoding a protein conferring resistance to a plant disease.

10. The vector of claim 8 wherein said heterologous DNA comprises a DNA encoding a protein conferring resistance to insect infestation.

11. The vector of claim 8 wherein said heterologous DNA comprises a DNA encoding a protein conferring tolerance to a herbicide.

12. The vector of claim 8 wherein said heterologous DNA comprises a DNA encoding a protein conferring tolerance enhanced nitrogen fixation or nodulation.

13. The vector of claim 8 wherein said heterologous DNA comprises a DNA encoding a protein conferring enhanced vigor or growth.

14. The vector of claim 8 wherein said heterologous DNA comprises a DNA encoding a SIRE-1-encoded protein.

15. The vector of claim 8 wherein said heterologous DNA comprises a gene or a fragment thereof.

16. The vector of claim 8 wherein said heterologous DNA comprises a DNA encoding an antisense transcript.

17. A method for transforming a host cell comprising the step of introducing a vector according to claim 5, or into said host cell.

18. A host cell transformed by the method of claim 17.

19. The host cell according to claim 18 wherein said host cell is a plant cell.

20. A method for making a heterologous protein comprising the steps of:

(a) culturing a host cell according to claim 18 under suitable medium and environmental conditions; and (b) isolating said protein from said cultured cell or from said medium.

21. The host cell according to claim 19 wherein said plant cell is a soybean cell.

22. An isolated, purified SIRE-1-encoded protein comprising an amino acid sequence selected from the group consisting of SEQ ID NO: 10, SEQ ID NO: 11, SEQ ID NO: 51, SEQ ID NO: 52, SEQ ID NO: 53, SEQ ID NO: 54, SEQ ID NO: 55, SEQ ID NO: 59, SEQ ID NO: 83, SEQ ID NO: 84 and fragments thereof, wherein said protein fragments retain the properties of their respective parent proteins.

23. The protein of claim 22, wherein said protein is a recombinant protein.

24. An isolated, purified antibody that specifically recognizes an epitope on a protein comprising an amino acid sequence selected from the group consisting of SEQ ID NO: 10, SEQ ID NO: 11, SEQ ID NO: 51, SEQ ID NO: 52, SEQ ID NO: 53, SEQ ID NO: 54, SEQ ID NO: 55, SEQ ID NO: 59, SEQ ID NO:83, SEQ ID NO: 84 and fragments thereof.

25. A method for transforming a plant cell, said method comprising the steps of:

(a) introducing a polynucleotide according to claim 1 into a plant cell; and (b) culturing said plant cell under suitable nutrient and environmental conditions; and (c) detecting said polynucleotide in said plant cell.

26. A method for transforming a plant cell, said method comprising the steps of:

(a) introducing a vector according to any one of claims 5 to 8 into a plant cell;

(b) culturing said plant cell under suitable nutrient and environmental conditions for the expression of an expression product of said polynucleotide; and (c) detecting said expression product.

27. A transformed plant cell produced by the method of claim 25 claim 26.

28. The transformed plant cell of claim 27 wherein said plant cell is a soybean cell.

29. A transgenic plant comprising a vector according to claims 5, 6, 7, or 8.

30. A method for generating a transgenic plant, the method comprising:

(a) introducing a vector according to claim 6 into a plant cell and detecting the polynucleotide in the plant cell; and (b) generating a plant from the cell of step (a), wherein the plant comprises cells which contain the heterologous DNA.

31. A transgenic plant produced according to the method of claim 30 or transgenic progeny thereof that contain the heterologous DNA.

32. An isolated, purified SIRE-1-encoded protein comprising SEQ ID NO: 10.

33. An isolated purified polynucleotide selected from the group consisting of:

(a) SEQ ID NO: 3; and (b) DNA molecules that hybridize under stringent conditions to the complement of SEQ ID NO: 3, wherein said DNA molecules have the properties of SEQ ID NO: 3.

34. An isolated purified polynucleotide selected from the group consisting of:

(a) SEQ ID NO: 8; and (b) DNA molecules that hybridize under stringent conditions to the complement of SEQ ID NO: 8, wherein said DNA molecules have the properties of SEQ ID NO: 8.

35. An isolated purified polynucleotide selected from the group consisting of:

(a) SEQ ID NO: 50; and (b) DNA molecules that hybridize under stringent conditions to the complement of SEQ ID NO: 50, wherein said DNA molecules have the properties of SEQ ID NO: 50.

36. An isolated, purified polynucleotide comprising the polynucleotide of SEQ ID NO: 3.

37. An isolated, purified polynucleotide comprising the polynucleotide of SEQ ID NO: 8.

38. An isolated, purified polynucleotide comprising the polynucleotide of SEQ ID NO: 50.

39. An isolated, purified SIRE-1-encoded protein comprising the amino acid sequence of SEQ ID NO: 10.

40. An isolated, purified SIRE-1-encoded protein comprising the amino acid sequence of SEQ ID NO: 11.

41. An isolated, purified SIRE-1-encoded protein comprising the amino acid sequence of SEQ ID NO: 51.

42. An isolated, purified SIRE-1-encoded protein comprising the amino acid sequence of SEQ ID NO: 52.

43. An isolated, purified SIRE-1-encoded protein comprising the amino acid sequence of SEQ ID NO: 53.

44. An isolated, purified SIRE-1-encoded protein comprising the amino acid sequence of SEQ ID NO: 54.

45. An isolated, purified SIRE-1-encoded protein comprising the amino acid sequence of SEQ ID NO: 55.

46. An isolated, purified SIRE-1-encoded protein comprising the amino acid sequence of SEQ ID NO: 59.

47. An isolated, purified antibody that specifically recognizes an epitope on a protein comprising an amino acid sequence of SEQ ID NO: 10.

48. An isolated, purified antibody that specifically recognizes an epitope on a protein comprising an amino acid sequence of SEQ ID NO: 11.

49. An isolated, purified antibody that specifically recognizes an epitope on a protein comprising an amino acid sequence of SEQ ID NO: 51.

50. An isolated, purified antibody that specifically recognizes an epitope on a protein comprising an amino acid sequence of SEQ ID NO: 52.

51. An isolated, purified antibody that specifically recognizes an epitope on a protein comprising an amino acid sequence of SEQ ID NO: 53.

52. An isolated, purified antibody that specifically recognizes an epitope on a protein comprising an amino acid sequence of SEQ ID NO: 54.

53. An isolated, purified antibody that specifically recognizes an epitope on a protein comprising an amino acid sequence of SEQ ID NO: 55.

54. An isolated, purified antibody that specifically recognizes an epitope on a protein comprising an amino acid sequence of SEQ ID NO: 59.

55. An isolated, purified SIRE-1-encoded protein comprising an amino acid sequence of SEQ ID NO: 83.

56. An isolated, purified SIRE-1-encoded protein comprising an amino acid sequence of SEQ ID NO: 84.

57. An isolated, purified antibody that specifically recognizes an epitope on a protein comprising an amino acid sequence of SEQ ID NO: 83.

58. An isolated, purified antibody that specifically recognizes an epitope on a protein comprising an amino acid sequence of SEQ ID NO: 84.

\* \* \* \* \*

UNITED STATES PATENT AND TRADEMARK OFFICE
CERTIFICATE OF CORRECTION

PATENT NO. : 6,559,359 B1
DATED : May 6, 2003
INVENTOR(S) : Howard Laten

It is certified that error appears in the above-identified patent and that said Letters Patent is hereby corrected as shown below:

Column 106,
Line 31, replace "to claim 5, or into" with -- to claims 6,7,8,9,10,11,12,13,14,15, or 16 into --.

Column 107,
Line 8, replace "claim 25 claims 26" with -- claim 25 or claim 26 --.

Signed and Sealed this

Twentieth Day of January, 2004

JON W. DUDAS
*Acting Director of the United States Patent and Trademark Office*